United States Patent [19]
Eckner et al.

[11] Patent Number: 5,658,784
[45] Date of Patent: Aug. 19, 1997

[54] NUCLEIC ACID ENCODING TRANSCRIPTION FACTOR P300 AND USES OF P300

[75] Inventors: Richard Eckner, Boston; Mark Ewen; David Livingston, both of Brookline, all of Mass.

[73] Assignee: Dana-Farber Cancer Institute, Inc., Boston, Mass.

[21] Appl. No.: 227,536

[22] Filed: Apr. 14, 1994

[51] Int. Cl.$^6$ ........................................... C07H 21/04
[52] U.S. Cl. ................... 435/325; 435/252.3; 435/320.1; 435/366; 536/23.5; 536/24.31
[58] Field of Search .............................. 435/320.1, 240.2, 435/252.3; 536/23.5, 24.31

[56] References Cited

U.S. PATENT DOCUMENTS 5,262,321  11/1993  Livingston et al. ................. 435/240.2

OTHER PUBLICATIONS

Chrivia et al., "Phosphorylated CREB binds specifically to the nuclear protein CBP," *Nature* 365:855–859 (1993).
Hans van Dam et al. "Differential Effects of the Adenovirus E1A Oncogene . . . ", *Molecular and Cellular Biology* 10:5857–5864, Nov. 1990.
Velcich et al. "Adenovirus E1a Proteins Repress Transcription . . . ", *Cell* 40:705–716, Mar. 1985.
Yee et al., "Detection of Cellular Proteins Associated with Human . . . ", *Virology* 147:142–153, 1985.
Braun et al., "Inhibition of Muscle Differentiation by the Edenovirus E1a Protein . . . ", *Genes & Development* 6:888–902, 1992.
Wang et al., "E1A Induces Phosphorylation of the Retinoblastoma Protein . . . ", *Molecular and Cellular Biology* 11:4253–4265, Aug. 1991.
Yaciuk et al., "Analysis with Specific Polyclonal Antiserum Indicates . . . ", *Molecular and Cellular Biology* 11:5389–5397, Nov. 1991.
Stein et al., "Analysis of E1A–Mediated Growth Regulation Functions: . . . ", *Journal of Virology* 64:4421–4427, Sep. 1990.
Whyte et al., "Cellular Targets for Transformation by the Adenovirus E1A Proteins", *Cell* 56:67–75, Jan. 1989.
Caruso et al., "Regulation of MyoD Gene Transcription and Protein . . . ", Istituto Biologia Cellulare, CNR, Rome, Italy, Aug. 1992.
Moran et al., "Interactions between Cell Growth–Regulating Domains . . . ", *Molecular and Cellular Biology* 8:1756–1764, Apr. 1988.
Fisher et al., "Mutational Analysis of the Adenovirus E1a Gene: . . . ", *The Embo Journal* 6:2053–2060, 1987.
Zerler et al., "Different Functional Domains of the Adenovirus E1A Gene Are Involved in Regulation . . . ", *Molecular and Cellular Biology* 7:821–829, Feb. 1987.
Harlow et al., "Association of Adenovirus Early–Region 1A Proteins with Cellular Polypeptides", *Molecular and Cellular Biology* 6:1579–1589, May 1986.
Rigby, Peter W.J., "Three in One and One in Three: It all Depends on TBP", *Cell* 72:7–10, Jan. 15, 1993.
Abraham et al., "p300 and p300–associated Proteins, Are Components . . . ", *Oncogene* 8:1639–1647, 1993.
Borrelli et al., "Adenovirus–2 E1A Products Repress Enhancer–Induced . . . ", *Nature* 312:608–612, Dec. 1984.
Lloyd et al., "Transformation Suppressor Activity of a Jun Transscription Factor . . . ", *Nature* 352:635–638, Aug. 1991.
Rikitake et al., *Mol. Cell. Biol.* 12(6), 2826–2836 (1992).
Howe et al., *PNAS* 87, 5883–5887 (1990).
Adams et al., *Nature Genetics* 4, 256–267 (1993).
Eckner et al., *Genes Develop.* 8(8), 869–884 (1994).

*Primary Examiner*—Kenneth R. Horlick
*Attorney, Agent, or Firm*—Weingarten, Schurgin, Gagnebin & Hayes

[57] ABSTRACT

The invention features an isolated nucleic acid hybridizable with the complement of the coding strand nucleic acid sequence presented in SEQ ID NO:1, and encoding a protein that is necessary for adenovirus transformation of a mammalian cell. The encoded protein, p300, cooperates with adenovirus E1A (Early-region 1A) proteins to establish the transformed state.

26 Claims, 27 Drawing Sheets

```
CCTTGTTTGTGTGCTAGGCTGGGGGAGAGAGGGCGAGAGAGCGGGCGAGAGTGGGC      60
AAGCAGGACGCCGGGCTGAGTGCTAACTGCGGGACGCAGAGAGTGCGGAGGGGAGTCGGG  120
TCGGAGAGAGGCGGCAGGGCTGAGTGCTAACTGCGGGACGCAGAGAGTGCGGAGGGGAGTCGGG 180
CGACCCCCAGCCCCCTCCCGTCCGCACACAGTAAACCCGCGTCCAGCAGCGGGCCGGC   240
GTCGACGCTAGGGGGACCATTACATAAACCCGCCCCGTCTTCTCCCGCCGC          300
GGCGCCCGAACTGAGCCCGGGCGCTCCAGCACTGCGCCCGGCGTGGGGCGTAGC       360
AGCGGGCCGTATTATTATTTCGCGCCGCCGGAAAGGAAGGCGAAGGAGGGGAGCCCGGCGCGAGGA 420
GGGGCCGCCTGCGCCCGCCGGAGCGGGCCCTCCTCGGTGGGCTCCGCGTCGGCGCGG    480
GCGTGCGGGGCGCTGCTCGGCCCGGCCCTCTGGTTCCGGCCAGCTCCGCT           540
CCCGGCGTCCTTGCCGCTCGGGCGAGTTCTCTGCGGCCGATGTGAGGCGGCGCCAGCC   600
TGGCTCTCGGCTCGGGCGAGTTCTCTGCGGCCATTAGGGCCGGTGCGGCGGCGCGG     660
AGCGCGGCGGCAGGAGGAGGGGTTCGGAGGGCCAGGCGCAGCCCGGAGGGGCACCGG    720
GAGGAGGTGAGTGTCTCTTGTCGCCTCCTCTCCCCGCCGAGGAAGAGGTTGATGCGGCGAGC 780
TGGCGATGAGAAGGAGGACAGCGCCAGGAGGAAGAGGTTGATGCGGCGGAGC         840
TCCGAGAGACCTCGGCGGAATTCGCCGCAGCCACGGCCTCGGCGACTGCCGCCTCTAGA  900
GCCGCGAGTTCTCGGGCTTGGGCCAGCCCCTCGCACTTGCCCTTACCTTTGTCTCTTGTG 960
CCCTCCTCCCGGGCATCCCCTCTCCAGCCACTGCGACCCGGCGAAGAGAAAAAGGAACTTCCCCACCCC 1020
TCCGCATCCCTCTCCAGCCACTGCGACCCGGCGAAGAGAAAAAGGAACTTCCCCACCCC 1080
CTCGGGTGCCGTCGGAGCCCCCAGCCCACCCCTGGGTGCGGGGGACCCCGGGCCG     1140
```

*FIG. 4A*

```
AAGAAGAGATTCCTGAGGATTCTGGTTTCCTCGCTTGTATCTCCGAAAGAATTAAAAA         1200
                                                          M          1

TGGCCGAGAATGTGGTGGAACCGGGCCGCCTTCAGCCAAGCGGCCTAAACTCTCATCTC         1260
 A  E  N  V  V  E  P  G  P  P  S  A  K  R  P  K  L  S  S  P         21

CGGCCCTCTCGGCGTCCGCCAGCGATGGCCACAGATTTTGGCTCTCTATTTGACTTGGAGC      1320
 A  L  S  A  S  A  S  D  G  T  D  F  G  S  L  F  D  L  E  H        41

ACGACTTACCAGATGAATTAATCAACTCTACAGAATTGGGACTAACCAATGGTGGTGATA       1380
 D  L  P  D  E  L  I  N  S  T  E  L  G  L  T  N  G  G  D  I        61

TTAAATCAGCTTCAGACAAGTCTTGGCATGGTACAAGATGCAGCTTCTAAACATAAACAGC     1440
 N  Q  L  Q  T  S  L  G  M  V  Q  D  A  A  S  K  H  K  Q  L        81

TGTCAGAATTGCTGCGATCTGGTAGTTCCCCTAACCTCAATATGGGAGTTGGTGGCCCAG       1500
 S  E  L  L  R  S  G  S  S  P  N  L  N  M  G  V  G  G  P  G       101

GTCAAGTCATGGCCAGCCAGGCCCAACAGAGCAGTCCTGGATTAGGTTTGATAAATAGCA      1560
 Q  V  M  A  S  Q  A  Q  Q  S  S  P  G  L  G  L  I  N  S  M       121

TGGTCAAAAGCCCAATGACACAGGCAGGCTTGACTTCTCCCAACATGGGGATGGGCACTA      1620
 V  K  S  P  M  T  Q  A  G  L  T  S  P  N  M  G  M  G  T  S       141
```

*FIG. 4B*

```
GTGGACCAAATCAGGGTCCTACGCAGTCAATCAGTATGATGAACAGTCCAGTAAATCAGC    1680
 G  P  N  Q  G  P  T  Q  S  T  G  M  M  N  S  P  V  N  Q  P     161

CTGCCATGGGAATGAACACAGGACGAATGCGGGCATGAATCCTGGAATGTTGGCTGCAG     1740
 A  M  G  M  N  T  G  T  N  A  G  M  N  P  G  M  L  A  A  G     181

GCAATGGACAAGGGATAATGCCTAATCAAGTCATGAACGGTTCAATTGGAGCAGGCCGAG    1800
 N  G  Q  G  I  M  P  N  Q  V  M  N  G  S  I  G  A  G  R  G     201

GGCGACAGGATATGCAGTACCCAAATCCAGGCATGGGAAGTGCTGGCAACTTACTGACTG    1860
 R  Q  D  M  Q  Y  P  N  P  G  M  G  S  A  G  N  L  L  T  E     221

AGCCTCTTCAGCAGGGCTCTCCCCCAGATGGGAGGACAAACAGGATTGAGAGGCCCCAGC   1920
 P  L  Q  Q  G  S  P  Q  M  G  G  Q  T  G  L  R  G  P  Q  P     241

CTCTTAAGATGGGAATGATGAACAACCCCAATCCTTATGGTTCACCATATACTCAGAATC    1980
 L  K  M  G  M  M  N  N  P  N  P  Y  G  S  P  Y  T  Q  N  P     261

CTGGACAGCAGATTGGAGCCAGTGGCCTTGGTCTCCAGATTCAGACAAAAACTGTACTAT    2040
 G  Q  Q  I  G  A  S  G  L  G  L  Q  I  Q  T  K  T  V  L  S     281

CAAATAACTTATCTCCATTTGCTATGGACAAAAAGGCAGTTCCTGGTGGAGGAATGCCCA    2100
 N  N  L  S  P  F  A  M  D  K  K  A  V  P  G  G  G  M  P  N     301

ACATGGGTCAACAGCCCCGCAGTCCAGGTCCAGGTCTGGTGACTCCAGTTGCCC         2160
 M  G  Q  Q  P  A  P  Q  V  Q  Q  P  G  L  V  T  P  V  A  Q     321
```

*FIG. 4C*

```
AAGGGATGGGTTCTGGAGCACATACAGCTGATCCAGAGAAGCGCAAGCTCATCCAGCAGC    2220
 G  M  G  S  G  A  H  T  A  D  P  E  K  R  K  L  I  Q  Q  Q     341

AGCTTGTTCTCCTTTTGCATGCTCACAAGTGCCAGCGCCGGGAACAGGCCAATGGGAAG    2280
 L  V  L  L (H) A  H  K (C) Q  R  R  E  Q  A  N  G  E  V        361

TGAGGCAGTGCAACCTTCCCCACTGTCGCACAATGAAGAATGTCCTAAACCACATGACAC    2340
 R  Q (C) N  L  P  H (C) R  T  M  K  N  V  L  N  H  M  T  H     381

ACTGCCAGTCAGGCAAGTCTTGCCAAGACATGATTGTCCTGTGTCCCCCTCGACAAATCATTT 2400
 C  Q  S  G  K  S (C) Q  V  A  H (C) A  S  S  R  Q  I  S        401

CACACTGGAAGAATTGTACAAGACATGATTGTCCTGTGTCCCCCTCAAAAATGCTG       2460
 H  W  K  N (C) T  R  H  D (C) P  V  C  L  P  L  K  N  A  G     421

GTGATAAGAGAAATCAACAGCCAATTTTGACTGGAGCACCCGTTGGACTTGGAAATCCTA   2520
 D  K  R  N  Q  Q  P  I  L  T  G  A  P  V  G  L  G  N  P  S     441

GCTCTCTAGGGGTGGGTCAACAGCAGTCTGCCCCAACCTAAGCACTGTTAGTCAGATTGATC 2580
 S  L  G  V  G  Q  Q  S  A  P  N  L  S  T  V  S  Q  I  D  P     461

CCAGCTCCATAGAAAGAGCCTATGCAGCTCTTGGACTACCCTATCAAGTAAATCAGATGC  2640
 S  S  I  E  R  A  Y  A  A  L  G  L  P  Y  Q  V  N  Q  M  P     481

CGACACAACCCCAGGTGCAAGCAAAAGAACCAGCAGAATCAGCAGCCTGGGCAGTCTCCCC  2700
 T  Q  P  Q  V  Q  A  K  N  Q  Q  N  Q  Q  P  G  Q  S  P  Q     501
```

C/H rich (1)

FIG. 4D

```
AAGGCATGCGGCCCATGAGCAACATGAGTGCTAGTCCTATGGGAGTAAATGGAGGTGTAG    2760
 G  M  R  P  M  S  N  M  S  A  S  P  M  G  V  N  G  G  V  G      521

GAGTTCAAACGCCGAGTCTTCTTTCTGACTCAATGTTGCATTCAGCCATAAATTCTCAAA    2820
 V  Q  T  P  S  L  L  S  D  S  M  L  H  S  A  I  N  S  Q  N      541

ACCCAATGATGAGTGAAAATGCCAGTGTGCCCTCCCTGGGTCCTTATGCCAACAGCAGCTC    2880
 P  M  M  S  E  N  A  S  V  P  S  L  G  P  M  P  T  A  A  Q      561

AACCATCCACTACTGGAATTCGGAAAACAGTGGCACGAAGATATTACTCAGGATCTTCGAA    2940
 P  S  T  T  G  I  R  K  Q  W  H  E  D  I  T  Q  D  L  R  N      581

ATCATCTTGTTCACAAACTCGTCCAAGCCCATATTTCCTACGGCCGGATCCTCCTGCTTTAA  3000
 H  L  V  H  K  L  V  Q  A  I  F  P  T  P  D  D  P  A  A  L  K   601

AAGACAGACGGATGGAAAACCTAGTTGCATATGCTCGGAAAGTTGAAGGGGACATGTATG   3060
 D  R  R  M  E  N  L  V  A  Y  A  R  K  V  E  G  D  M  Y  E      621

AATCTGCAAACAATCGAGCGGAATACTACCACCTTCTAGCTGAGAAAATCTATAAGATCC   3120
 S  A  N  N  R  A  E  Y  Y  H  L  L  A  E  K  I  Y  K  I  Q      641

AGAAAGAACTAGAAGAAAAACGAAGGACCAGACTACAGAAGCAGAACATGCTACCAAATG   3180
 K  E  L  E  E  K  R  R  T  R  L  Q  K  Q  N  M  L  P  N  A      661

CTGCAGGCATGGTTCCAGTTTCCATGAATCCAGGGCCTAACATGGGACAGCCGCAACCAG   3240
 A  G  M  V  P  V  S  M  N  P  G  P  N  M  G  Q  P  Q  P  G      681
```

*FIG. 4E*

```
GAATGACTTCTAATGGCCCCTCTACCTGACCCAAGTATGATCCGTGGCAGTGTGCCAAACC    3300
 M  T  S  N  G  P  L  P  D  P  S  M  I  R  G  S  V  P  N  Q     701

AGATGATGCCTCGAATAACTCCACAATCTGGTTTGAATCAATTTGGCCAGATGAGCATGG    3360
 M  M  P  R  I  T  P  Q  S  G  L  N  Q  F  G  Q  M  S  M  A     721

CCCAGCCCCCTATTGTACCCCGGCAAACCCCTCCTCTTCAGCACCATGGACAGTTGGCTC    3420
 Q  P  P  I  V  P  R  Q  T  P  P  L  Q  H  H  G  Q  L  A  Q     741

AACCTGGAGCTCTCAACCCGCCTCGTATGGGCCTATGCAACAGCCTTCCAACC          3480
 P  G  A  L  N  P  P  M  G  Y  G  P  R  M  Q  Q  P  S  N  Q     761

AGGGCCAGTTCCTTCCTCAGACTCAGTTCCCATCACAGGGAATGAATGTAACAAATATCC    3540
 G  Q  F  L  P  Q  T  Q  F  P  S  Q  G  M  N  V  T  N  I  P     781

CTTTGGCTCCGTCCAGCGGTCAAGCTCCAGTGTCTCAAGCACAAATGTCTAGTTCTTCCT    3600
 L  A  P  S  S  G  Q  A  P  V  S  Q  A  Q  M  S  S  S  S  C     801

GCCCGGTGAACTCTCCTATAATGCCTCCAGGGAGCCACATTCACTGTCCCC            3660
 P  V  N  S  P  I  M  P  P  G  S  Q  G  S  H  I  H  C  P  Q     821

AGCTTCCTCAACCAGTCTTCATCAGAATTCACCCTGTACCTAGTCGTACCCCCA         3720
 L  P  Q  P  A  L  H  Q  N  S  P  S  P  V  P  S  R  T  P  T     841

CCCCTCACCATACTCCCCCAAGCACATAGGGGGCTCAGCAGCAGCAACAATTCCAG      3780
 P  H  H  T  P  P  S  I  G  A  Q  Q  P  P  A  T  T  I  P  A     861
```

*FIG. 4F*

```
CCCCTGTTCCTACACCACCAGCCATGCCACCTGGGCCACAGTCCCAGGCTCTACATCCCC    3840
  P  V  P  T  P  P  A  M  P  P  G  P  P  Q  S  Q  A  L  H  P  P     881

CTCCAAGGCAGACACCTACACCACCAACAACAACTTCCCCAACAAGTGCAGCCTTCAC      3900
  P  R  Q  T  P  T  P  P  T  T  Q  L  P  Q  Q  V  Q  P  S  L     901

TTCCTGCTGCACCTTCTGCTGACCTTGCTGACCCCCAGCAGCCTGCTCACAGCAGAGCACAG  3960
  P  A  A  P  S  A  D  Q  P  Q  Q  Q  P  R  S  Q  Q  S  T  A     921

CAGCGTCTGTGTTCCTACCCCAAACGCACCGTCCAACTTGAAGGACCAGGTATCAAATCCTCCACTTT  4020
  A  S  V  P  T  P  N  A  P  L  L  P  P  Q  P  A  T  P  L  S     941

CCCAGCCAGCTGTAAGCATTGCTGAGAAGCAGCCTTCCCAGGAAGTGAAGATGGAGGCCA    4080
  Q  P  A  V  S  I  E  G  Q  V  S  N  P  P  S  T  S  S  T  E     961

AAGTGAATTCTCAGGCCATTGCTGAGAAGCAGCCTTCCCAGGAAGTGAAGATGGAGGCCA    4140
  V  N  S  Q  A  I  A  E  K  Q  P  S  Q  E  V  K  M  E  A  K     981

AAATGGAAGTGGATCAACCAGAACCAGAGCCAGCCGGAGGATATTTCAGAGTCTA         4200
  M  E  V  D  Q  P  E  P  A  D  T  Q  P  E  D  I  S  E  S  K    1001

AAGTGGAAGACTGTAAAATGGAATCTACCGAAACAGAAGAGAGAAGCACTGAGTTAAAAA    4260
  V  E  D  C  K  M  E  S  T  E  T  E  E  R  S  T  E  L  K  T    1021

CTGAAATAAAAGAGGAGGAAGACCAAGCCAAGTACTTCAGCTACCCAGTCATCTCCGGCTC    4320
  E  I  K  E  E  D  Q  P  S  T  S  A  T  Q  S  S  P  A  P    1041
```

*FIG. 4G*

```
CAGGACAGTCAAAGAAAAAGATTTCAAACCAGAAGAACTACGACAGGCACTGATGCCAA    4380
 G  Q  S  K  K  K  I  F  K  P  E  E  L  R  Q  A  L  M  P  T    1061

CATTGGAGGCACTTTACCGTCAGGATCCAGAATCCCTTTCGTCAACCTGTGGACC          4440
 L  E  A  L  Y  R  Q  D [P  E  S  L  P  F  R  Q  P  V  D  P]    1081

CTCAGCTTTTAGGAATCCCTGATTACTTTGATATTGTGAAGAGCCCCATGGATCTTTCTA    4500
[Q  L  L  G  I  P  D  Y  F  D  I  V  K  S  P  M  D  L  S  T]   1101

CCATTAAGAGGAAGTTAGACACTGGACAGTATCAGGAGCCCTGGCAGTATGTCGATGATA    4560
[I  K  R  K  L  D  T  G  Q  Y  Q  E  P  W  Q  Y  V  D  D  I]   1121

TTTGGCTTATGTTCAATAATGCCTGGTTATATAACCGAAAACATCACGGGTATACAAAT    4620
[W  L  M  F  N  N  A  W  L  Y  N  R  K  T  S  R  V  Y  K  Y]   1141

ACTGCTCCAAGCTCTCTGAGGTCTTCTTTGAACAAGAAATTGACCCAGTGATGCAAAGCTTG    4680
 C  S  K  L  S  E  V  F  F  E  Q  E  I  D  P  V  M  Q  S  L  G    1161

GATACTGTTGTGGCAGAAAGTTGGAGCTCTTCTCCACAGACACTGTTGCTACGGCAAAC    4740
 Y [C] G  R  K  L  E  F  S  P  Q  T  L [C  C] Y  G  K  Q        1181

AGTTGTGCACAAATACCTCGTGATGCCACTTATTACAGTTACCAGAACAGGTATCATTTCT    4800
 L [C] T  I  P  R  D  A  T  Y  Y  S  Y  Q  N  R  Y [H] F [C]   1201

GTGAGAAGTGTTTCAATGAGATCCAAGGGGAGAGCGTTCTTGGGGATGACCCTTCCC    4860
 E  K [C] F  N  E  I  Q  G  E  S  V  L  G  D  D  P  S  Q      1221
```

C/H
rich ②

FIG. 4H

```
AGCCTCAAACTACAATAAAGAACAATTTTCCAAGAGAAAAATGACACACTGGATC         4920
 P  Q  T  T  I  N  K  E  Q  F  S  K  R  R  K  N  D  T  L  D  P   1241

CTGAACTGTTTGTTGAATGTACAGAGTGCGGAAGAAAGATGCATCAGATCTGTGTCCTTC    4980
 L  E  L  F  V  E  [C] T  E  [C] G  R  K  M  [H] Q  I  [C] V  L  [H]  1261

ACCAGAGATCATCTGGCCTGCTGATTCGTCTGTGATGGCTGTGTTAAAGAAAAGTGCAC     5040
 T  [H] E  I  I  W  P  A  G  F  V  [C] D  D  G  [C] L  K  K  S  A  R   1281

GAACTAGGAGAAGAAAATAAGTTTTCTGCTAAAAGGTTGCCATCTACCAGACTTGGCACCT   5100
 E  L  T  R  K  E  N  K  F  S  A  K  R  L  P  S  T  R  L  G  T  F   1301

TTCTAGAGAATCGTGTGAATGACTTTCTGAGGCGACAGAATCACCCTGAGTCAGGAGAGG    5160
 F  L  E  N  R  V  N  D  F  L  R  R  Q  [N] [H] P  E  S  G  E  V   1321

TCACTGTGTTAGAGTAGTTCATGCTTCTGACAAAACCGTGGAAGTAAAACCAGGCATGAAAG 5220
 S  T  V  R  V  V  [H] A  S  D  K  T  V  E  V  K  P  G  M  K  A   1341

CAAGGTTTGTGGACAGTGGAGAGATGGCAGAATCCTTTCCATACCGAACCAAAGCCCTCT   5280
 Q  R  F  V  D  S  G  E  M  A  E  S  F  P  Y  R  T  K  A  L  F   1361

TTGCCTTTGAAGAAATTGATGGTGTTGACCTGTGCTTCTTTGGCATGCATGTTCAAGAGT   5340
 L  A  F  E  E  I  D  G  V  D  L  [C] F  F  G  M  [H] V  Q  E  Y   1381

ATGGCTCTGACTGCCCTCCACCCAACCAGAGGAGTATACATATCTTACCTCGATAGTG    5400
 Y  G  S  D  [C] P  P  P  N  Q  R  R  V  Y  I  S  Y  L  D  S  V   1401
```

C/H rich ②

*FIG. 4I*

```
TTCATTTCTTCCGTCCTAAATGCTTGAGGACTGCAGTCTATCATGAAATCCTAATTGGAT    5460
 H  F  F  R  P  K  C  L  R  T  A  V  Y  H  E  I  L  I  G  Y    1421

ATTTAGAATATGTCAAGAAATTAGGTTACACAACAGGGCATATTTGGCATGTCCACCAA     5520
 L  E  Y  V  K  K  L  G  Y  T  T  G  [H] I  W  A  [C] P  P  S   1441

GTGAGGGAGATGATTATATCTTCCATTGCCATCCTCCTGACCAGAAGATACCCAAGCCCA    5580
 E  G  D  D  Y  I  F  [H][C] P  P  D  Q  K  I  P  K  P  K       1461

AGCCGACTGCAGGAATGGTACAAAAAATGCTTGACAAGGCTGTATCAGAGCGTATTGTCC    5640
 R  L  Q  E  W  Y  K  K  M  L  D  K  A  V  S  E  R  I  V  H     1481

ATGACTACAAGGATATATTTTAAACAAGCTACTGAAGATAGATTAACAAGTGCAAAGGAAT   5700
 D  Y  K  D  I  F  K  Q  A  T  E  D  R  L  T  S  A  K  E  L     1501

TGCCTTATTTCGAGGGTGATTTCTGGCCCAATGTTCTGGAAGAAAGCATTAAGGAACTGG    5760
 P  Y  F  E  G  D  F  W  P  N  V  L  E  E  S  I  K  E  L  E     1521

AACAGGAGGAAGAAGAGAGAAAACGAGAGGAAAAACACCAGCAATGAAAGCACAGATGTGA   5820
 Q  E  E  E  E  R  K  R  E  E  N  T  S  N  E  S  T  D  V  T     1541

CCAAGGGAGACAGCAAAATGCTAAAAAGAAGAATAATAAGAAAACCAGCAAAAATAAGA    5880
 K  G  D  S  K  N  A  K  K  K  N  N  K  K  T  S  K  N  K  S     1561

GCAGCCTGAGTAGGGCAACAAGAAGAAACCCGGGATGCCCAATGTATCTAACGACCTCT    5940
 S  L  S  R  G  N  K  K  K  P  G  M  P  N  V  S  N  D  L  S    1581
```

C/H rich ②

FIG. 4J

```
CACAGAAACTATATGCCACCATGGAGAAGCATAAAGAGGTCTTCTTTGTGATCCGCCTCA    6000
 Q  K  L  Y  A  T  M  E  K  H  K  E  V  F  F  V  I  R  L  I     1601
TTGCTGGCCCTGCTGCCAACTCCCTGCCTCCCATTGTTGATCCTCCTCATCCCT          6060
 A  G  P  A  A  N  S  L  P  P  I  V  D  P  D  P  L  I  P  C     1621
GCGATCTGATGGTCGGGATGCGTTTCTCACGCTGGCAAGGACAAGCACCTGGAGT         6120
 D  L  M  D  G  R  D  A  F  L  T  L  A  R  D  K [H] L  E  F     1641
TCTCTTCACTCCGAAGAGCCCAGTGGTCCACCATGTGCTGGTGGAGCTGCACACGC        6180
 S  S  L  R  R  A  Q  W  S  T  M [C] M  L  V  E  L [H] T  Q     1661
AGAGCCAGGACCGCTTTGTCTACACCTGCAATGAATGCAAGCACCATGTGGAGACACGCT   6240
 S  Q  D  R  F  V  Y  T [C] N  E [C] K [H][H] V  E  T  R  W     1681
GGCACTGTACTGTGTCTGTGAGGATTATGACTTGTGTATCACCTGCTATAACACTAAAAACC 6300
[H][C] T  V [C] E  D  Y  D  L [C] I  T [C] Y  N  T  K  N [H]    1701
ATGACAAAAATGGAGAAACTAGGCCTTGGCTTAGATGATGAGAGCAACAACCAGCAGG     6360
 D [H] K  M  E  K  L  G  L  G  L  D  D  E  S  N  N  Q  Q  A     1721
CTGCAGCCACCCAGAGCCCAGGGCGATTCTCGCCGAGTATCCAGGCTGCATCCAGT       6420
 A  A  T  Q  S  P  G  D  S  R  R  L  S  I  Q  R [C] I  Q  S     1741
CTCTGGTGCCATGCTTGCCAGTGTCGGAATGCCAATTGCTCACTGCCATCCTGCCAGAAGA 6480
 L  V [H] A [C] Q  R  N  A  N [C] S  L  P  S [C] Q  K  M       1761
```

C/H rich ③

*FIG. 4K*

C/H
rich ③

```
TGAAGCGGGTGTGTGCAGCATACCAAGGGTTGCAAACGGAAAACCAATGGCGGGGTGCCCA    6540
 K  R  V  V  Q  H  T  K  G  C  K  R  K  T  N  G  G  C  P  I      1781

TCTGCAAGCAGCTCATTGCCCTGCTGCTACCATGCCAAGCACTGCCAGGAGAACAAAT       6600
 C  K  Q  L  I  A  L  C  Y  H  A  K  H  Q  E  N  K  C            1801

GCCCGGTGCCGTTCTGCCTAAACATCAAGCAGAAGCTCCGGCAACAGCAGCTGCAGCACC     6660
 P  V  P  F  C  L  N  I  K  Q  K  L  R  Q  Q  Q  L  Q  H  R      1821

GACTACAGCAGGCCCAAATGCTTCGCAGGAGGATGGCCAGCATGCAGCGGACTGGTGTGG     6720
 L  Q  Q  A  Q  M  L  R  R  R  M  A  S  M  Q  R  T  G  V  V      1841

TTGGGCAGCAACAGGGCCTCCCCTCCCCCACTCCTGCCACTCCAACGACACCAACTGGCC    6780
 G  Q  Q  Q  G  L  P  S  P  T  P  A  T  P  T  T  P  T  G  Q      1861

AACAGCCAACCACCCCGCCAGGACTCAAGCTGCTGGCCCTGTGTCCCAGCCTACCCCTCCCA  6840
 Q  P  T  T  P  Q  T  P  Q  P  T  S  Q  P  Q  P  T  P  P  N      1881

ATAGCATGCCACCCTACTTGCCCAGGACTCAAGCTGCTGGCCCTGTGTCCCAGGGTAAGG    6900
 S  M  P  P  Y  L  P  R  T  Q  A  A  G  P  V  S  Q  G  K  A      1901

CAGCAGGCCAGGTGACCCCTCCAACCTCCTCAGACTGCTCAGCACCCCTTCCAGGGC       6960
 A  G  Q  V  T  P  P  T  P  P  Q  T  A  Q  P  P  L  P  G  P      1921

CCCCACCTACAGCAGTGCAAATGCAGATTCAGAGAGCAGGCGGGAGACGCAGGCC         7020
 P  P  T  A  V  E  M  A  M  Q  I  Q  R  A  A  E  T  Q  R  Q      1941
```

*FIG. 4L*

```
AGATGGCCCACGTGCAAATTTTTCAAAGGCCAATCCAACACCAGATGCCCCCGATGACTC    7080
 M  A  H  V  Q  I  F  Q  R  P  I  Q  H  Q  M  P  P  M  T  P     1961

CCATGGCCCCCATGGGTATGAACCCCACCTCCCATGACCCAGAGGTCCCAGTGGGCATTTGG    7140
 M  A  P  M  G  M  N  P  P  P  M  T  R  G  P  S  G  H  L  E     1981

AGCCAGGGGATGGGACCGACAGGATGCAGCAACAGCCACCCTGGAGCCAAGGAGGATTGC    7200
 P  G  M  G  P  T  G  M  Q  Q  Q  P  P  W  S  Q  G  G  L  P     2001

CTCAGCCCCAGCAACTACAGTCTGGGATGCCCAAGGCCAGCCATGATGTCAGTGGCCCAGC    7260
 Q  P  Q  Q  L  Q  S  G  M  P  R  P  A  M  M  S  V  A  Q  H     2021

ATGGTCAACCTTTGAACATGGCTCCACAACAGCCAGGATTGGGCCAGGTAGGTATCAGCCCAC    7320
 G  Q  P  L  N  M  A  P  Q  P  G  L  G  Q  V  G  I  S  P  L     2041

TCAAACCAGGCACTGTGTCTCAACAAGCCTTACAAAACCCTTTGCGGACTCTCAGGTCTC    7380
 K  P  G  T  V  S  Q  Q  A  L  Q  N  L  L  R  T  L  R  S  P     2061

CCAGCTCTCCCCTGCAGCAGCAGCAACAGGTGCTTAGTATCCTTCACGCCAACCCCCAGCTGT    7440
 S  S  P  L  Q  Q  Q  Q  V  L  S  I  L  H  A  N  P  Q  L  L     2081

TGGCTGCATTCATCAAGCAGCGGGCTGCCAAGTATGCCAACTCTAATCCACAACCCATCC    7500
 A  A  F  I  K  Q  R  A  A  K  Y  A  N  S  N  P  Q  P  I  P     2101

CTGGGCAGCCTGGCATGCCCCAGGGGCAGCCAGGGCTACAGCCACCTACAGCCATGCCAGGTC    7560
 G  Q  P  G  M  P  Q  G  Q  P  G  L  Q  P  P  T  M  P  G  Q     2121
```

*FIG. 4M*

```
AGCAGGGGGTCCACTCCAATCCAGCCATGCAGAACATGAATCCAATGCAGGCGGGCGTTC    7620
 Q  G  V  H  S  N  P  A  M  Q  N  M  N  P  M  Q  A  G  V  Q     2141

AGAGGGCTGGCCTGCCCCAGCAACTCCAGCAGCAACTCCAGCCACCCATGGGAGGA        7680
 R  A  G  L  P  Q  Q  Q  P  Q  Q  Q  L  Q  P  P  M  G  G  M     2161

TGAGCCCCCAGGCTCAGCAGATGAACATGAACCACAACCATGCCTTCACAATTCCGAG      7740
 S  P  Q  A  Q  Q  M  N  M  N  H  N  T  M  P  S  Q  F  R  D     2181

ACATCTTGAGACGACAGCAAATGATGCAACAGCAGCAACAGGGAGCAGGGCCAGGAA       7800
 I  L  R  R  Q  Q  M  M  Q  Q  Q  Q  Q  G  A  G  P  G  I        2201

TAGGCCCTGGAATGGCCAACCATAACCAGTTCCAAGGAGTTGGCTACCCAC             7860
 G  P  M  A  N  H  N  Q  F  Q  Q  P  Q  G  V  G  Y  P  P        2221

CACAGCCGCAGCAGCGGATGCAGCATCACATGCAACAGATGCAACAAGGAAATATGGGAC    7920
 Q  P  Q  Q  R  M  Q  H  H  M  Q  Q  M  Q  Q  G  N  M  G  Q     2241

AGATAGGCCAGCTTCCCCAGGCCCTTGGGCAGAGGCCAGGTGCCAGTCTACAGGCCTATC    7980
 I  G  Q  L  P  Q  A  L  G  A  E  A  G  A  S  L  Q  A  Y  Q     2261

AGCAGCGACTCCTTCAGCAACAGATGGGGTCCCCTGTTCAGCAACCCCATGAGCCCCC      8040
 Q  R  L  L  Q  Q  Q  M  G  S  P  V  Q  P  N  P  M  S  P  Q     2281

AGCAGCATATGCTCCCAAATCAGGCCCAGTCCCCACACTTACAAGGCCAGATCCCCTA      8100
 Q  H  M  L  P  N  Q  A  Q  S  P  H  L  Q  G  Q  Q  I  P  N     2301
```

*FIG.4N*

```
ATTCTCTCTCCAATCAAGTGGCTCTCCCAGCCTGTCCCTTCTCCACGGCCACAGTCCC      8160
 S  L  S  N  Q  V  R  S  P  Q  P  V  P  S  P  R  P  Q  S  Q     2321

AGCCCCCCACTCCAGTCCTTCCCAAGGATGCAGCCTTCTCCACACCACGTTT            8220
 P  P  H  S  S  P  S  P  R  M  Q  P  Q  P  S  P  H  H  V  S    2341

CCCCACAGACAAGTTCCCCACATCCTGGACTGGTAGCTGCCAGGCCAACCCCATGGAAC     8280
 P  Q  T  S  S  P  H  P  G  L  V  A  A  Q  A  N  P  M  E  Q    2361

AAGGGCATTTGCCAGCCCGGACCCAGAATTCAATGCTTTCTCAGCTTGCTAGCAATCCAG    8340
 G  H  F  A  S  P  D  D  Q  N  S  M  L  S  Q  L  A  S  N  P  G 2381

GCATGGCAAACCTCCATGGTGCAAGCGCCACGGACTCAGCACCGATAACTCAG           8400
 M  A  N  L  H  G  A  S  A  T  D  L  G  L  S  T  D  N  S  D    2401

ACTTGAATTCAAACCTCTCACAGAGTACACTAGACATAGAGACACCTTGTATTT          8460
 L  N  S  N  L  S  Q  S  T  L  D  I  H  *                       2414

GGGAGCAAAAAAATTATTTCTCTTAACAAGACTTTTTGTACTGAAAACAATTTTTTGA      8520

ATCTTTCGTAGCCTAAAGACAATTTCCTTGGAACACATAAGAACTGTGCAGTAGCCGT      8580

TTGTGGTTTAAAGCAAACATGCAAGATGAACCTGAGGGATGATAGAATACAAAGAATATA    8640

TTTTTGTTATGGGCTGGTTACCACCAGCCTTTCTTCCCCTTTGTGTGTGGTTCAAGTG      8700

TGCACTGGGAGGAGGCTGAGGCCTGAAGCCAAACAATATGCTCCTGCCTTGCACCTCC      8760

AATAGGTTTTATTATTTTTTTAAATTAATGAACATATGTAATATTAATGAACATATGTA    8820

ATATTAATAGTTATTATTTACTGGTGCAGATGGTTGACATTTTTCCTATTTTCCTCACT     8880

TTATGAAGAGTTAAACATTTCTAAACATATAAATATATATTAAAAGGGGTTAATGTTACTTTGAA 8940

ATTACATTCTATATATATATATATATATATAAATATATATTAAAATATATTAAATACCAGTTTTTTTC 9000

TCTGGGTGCAAAGATGTTCATTCTTTTAAAAAATGTTTAAAAAAAA      9046
```

FIG. 40

```
consensus           F   PV       DY  I  PMD             Y         D  L  N    YN p300      1070  PESLEF RQPVDPQLLGIPD YFDIVKS PM LSTIKRKLDTG QYQEPWQYVDD IWLMFN NAWLY NRK
CCG1(1)   1400  PNTYEF HTPVNAKVV--KD YKIITRP PM DLQTLRENVRKRI YPSREEFREHL ELIVK NSATY NGP
CCG1(2)   1523  PDSWEF HHPVNKKFV---PD YKVIVNP PM DLETIRKNISKHKY QSRESFLDDV NLILA NSVKY NGP
RING3(1)    47  QFAWEF RQPVDAVKLGLPD YHKIIKQ PM DMGTIKRRLENNYY WAASECMQDF NTMFT NCYIY NKP
RING3(2)   320  AYAWEF YKPVDASALGLHD YHDIIKH PM DLSTVKRKMENRD YRDAQEFAAD VRLMF SNCYKY NPP
hBRM      1418  QLSEVF IQLPSRKEL--PE YELIRK PV DFKKIKERIRNHKY RSLGDLEKD VMLLC HNAQTF NLE
PEREGRIN   648  DTGNIF SEPVPLSEV---PD YLDHIKK EM DFFTMKQNLEAYR YLNFDDFEED FNLIVS NCLKY NAK helix                  T       T  helix   T
```

FIG. 4P

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:

( A ) LENGTH: 9046 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( i x ) FEATURE:
( A ) NAME/KEY: CDS
( B ) LOCATION: 1200..8441

( x i ) SEQUENCE DESCRIPTION: SEQ ID NO:1:

```
CCTTGTTTGT GTGCTAGGCT GGGGGGGAGA GAGGGCGAGA GAGAGCGGGC GAGAGTGGGC      60
AAGCAGGACG CCGGGCTGAG TGCTAACTGC GGGACGCAGA GAGTGCGGAG GGGAGTCGGG     120
TCGGAGAGAG GCGGCAGGGG CCAGAACAGT GGCAGGGGGC CCGGGGCGCA CGGGCTGAGG     180
CGACCCCCAG CCCCCTCCCG TCCGCACACA CCCCCACCGC GGTCCAGCAG CCGGGCCGGC     240
GTCGACGCTA GGGGGACCA TTACATAACC CGCGCCCCGG CCGTCTTCTC CCGCCGCCGC      300
GGCGCCCGAA CTGAGCCCGG GGCGGGCGCT CCAGCACTGG CCGCCGGCGT GGGGCGTAGC     360
AGCGGCCGTA TTATTATTTC GCGGAAAGGA AGGCGAAGGA GGGGAGCGCC GGCGCGAGGA     420
GGGGCCGCCT GCGCCCGCCG CCGGAGCGGG GCCTCCTCGG TGGGCTCCGC GTCGGCGCGG     480
GCGTGCGGGC GGCGCTGCTC GGCCCGGCCC CCTCGGCCCT CTGGTCCGGC CAGCTCCGCT     540
CCCGGCGTCC TTGCCGCGCC TCCGCCGGCC GCCGCGCGAT GTGAGGCGGC GGCGCCAGCC     600
TGGCTCTCGG CTCGGGCGAG TTCTCTGCGG CCATTAGGGG CCGGTGCGGC GGCGGCGCGG     660
AGCGCGGCGG CAGGAGGAGG GTTCGGAGGG TGGGGGCGCA GGCCCGGGAG GGGGCACCGG     720
GAGGAGGTGA GTGTCTCTTG TCGCCTCCTC CTCTCCCCCC TTTTCGCCCC CGCCTCCTTG     780
TGGCGATGAG AAGGAGGAGG ACAGCGCCGA GGAGGAAGAG GTTGATGGCG GCGGCGGAGC     840
TCCGAGAGAC CTCGGCTGGG CAGGGGCCGG CCGTGGCGGG CCGGGGACTG CGCCTCTAGA     900
GCCGCGAGTT CTCGGGAATT CGCCGCAGCG GACCGGCCTC GGCGAATTTG TGCTCTTGTG     960
CCCTCCTCCG GGCTTGGGCC AGGCCGGCCC CTCGCACTTG CCCTTACCTT TTCTATCGAG    1020
TCCGCATCCC TCTCCAGCCA CTGCGACCCG GCGAAGAGAA AAAGGAACTT CCCCCACCCC    1080
CTCGGGTGCC GTCGGAGCCC CCAGCCCAC CCTGGGTGC GGCGCGGGA CCCCGGGCCG       1140
AAGAAGAGAT TCCTGAGGA TTCTGGTTTT CCTCGCTTGT ATCTCCGAAA GAATTAAAA    1199
```

```
ATG GCC GAG AAT GTG GTG GAA CCG GGG CCG CCT TCA GCC AAG CGG CCT    1247
Met Ala Glu Asn Val Val Glu Pro Gly Pro Pro Ser Ala Lys Arg Pro
 1               5                  10                  15

AAA CTC TCA TCT CCG GCC CTC TCG GCG TCC GCC AGC GAT GGC ACA GAT    1295
Lys Leu Ser Ser Pro Ala Leu Ser Ala Ser Ala Ser Asp Gly Thr Asp
                20                  25                  30

TTT GGC TCT CTA TTT GAC TTG GAG CAC GAC TTA CCA GAT GAA TTA ATC    1343
Phe Gly Ser Leu Phe Asp Leu Glu His Asp Leu Pro Asp Glu Leu Ile
            35                  40                  45

AAC TCT ACA GAA TTG GGA CTA ACC AAT GGT GGT GAT ATT AAT CAG CTT    1391
Asn Ser Thr Glu Leu Gly Leu Thr Asn Gly Gly Asp Ile Asn Gln Leu
        50                  55                  60

CAG ACA AGT CTT GGC ATG GTA CAA GAT GCA GCT TCT AAA CAT AAA CAG    1439
Gln Thr Ser Leu Gly Met Val Gln Asp Ala Ala Ser Lys His Lys Gln
 65                  70                  75                  80

CTG TCA GAA TTG CTG CGA TCT GGT AGT TCC CCT AAC CTC AAT ATG GGA    1487
```

```
Leu Ser Glu Leu Leu Arg Ser Gly Ser Ser Pro Asn Leu Asn Met Gly
            85                      90                      95

GTT GGT GGC CCA GGT CAA GTC ATG GCC AGC CAG GCC CAA CAG AGC AGT    1535
Val Gly Gly Pro Gly Gln Val Met Ala Ser Gln Ala Gln Gln Ser Ser
            100                     105                     110

CCT GGA TTA GGT TTG ATA AAT AGC ATG GTC AAA AGC CCA ATG ACA CAG    1583
Pro Gly Leu Gly Leu Ile Asn Ser Met Val Lys Ser Pro Met Thr Gln
            115                     120                     125

GCA GGC TTG ACT TCT CCC AAC ATG GGG ATG GGC ACT AGT GGA CCA AAT    1631
Ala Gly Leu Thr Ser Pro Asn Met Gly Met Gly Thr Ser Gly Pro Asn
    130                     135                     140

CAG GGT CCT ACG CAG TCA ACA GGT ATG ATG AAC AGT CCA GTA AAT CAG    1679
Gln Gly Pro Thr Gln Ser Thr Gly Met Met Asn Ser Pro Val Asn Gln
145                     150                     155                 160

CCT GCC ATG GGA ATG AAC ACA GGG ACG AAT GCG GGC ATG AAT CCT GGA    1727
Pro Ala Met Gly Met Asn Thr Gly Thr Asn Ala Gly Met Asn Pro Gly
                    165                     170                     175

ATG TTG GCT GCA GGC AAT GGA CAA GGG ATA ATG CCT AAT CAA GTC ATG    1775
Met Leu Ala Ala Gly Asn Gly Gln Gly Ile Met Pro Asn Gln Val Met
            180                     185                     190

AAC GGT TCA ATT GGA GCA GGC CGA GGG CGA CAG GAT ATG CAG TAC CCA    1823
Asn Gly Ser Ile Gly Ala Gly Arg Gly Arg Gln Asp Met Gln Tyr Pro
            195                     200                     205

AAC CCA GGC ATG GGA AGT GCT GGC AAC TTA CTG ACT GAG CCT CTT CAG    1871
Asn Pro Gly Met Gly Ser Ala Gly Asn Leu Leu Thr Glu Pro Leu Gln
    210                     215                     220

CAG GGC TCT CCC CAG ATG GGA GGA CAA ACA GGA TTG AGA GGC CCC CAG    1919
Gln Gly Ser Pro Gln Met Gly Gly Gln Thr Gly Leu Arg Gly Pro Gln
225                     230                     235                 240

CCT CTT AAG ATG GGA ATG ATG AAC AAC CCC AAT CCT TAT GGT TCA CCA    1967
Pro Leu Lys Met Gly Met Met Asn Asn Pro Asn Pro Tyr Gly Ser Pro
                245                     250                     255

TAT ACT CAG AAT CCT GGA CAG CAG ATT GGA GCC AGT GGC CTT GGT CTC    2015
Tyr Thr Gln Asn Pro Gly Gln Gln Ile Gly Ala Ser Gly Leu Gly Leu
            260                     265                     270

CAG ATT CAG ACA AAA ACT GTA CTA TCA AAT AAC TTA TCT CCA TTT GCT    2063
Gln Ile Gln Thr Lys Thr Val Leu Ser Asn Asn Leu Ser Pro Phe Ala
            275                     280                     285

ATG GAC AAA AAG GCA GTT CCT GGT GGA GGA ATG CCC AAC ATG GGT CAA    2111
Met Asp Lys Lys Ala Val Pro Gly Gly Gly Met Pro Asn Met Gly Gln
    290                     295                     300

CAG CCA GCC CCG CAG GTC CAG CAG CCA GGT CTG GTG ACT CCA GTT GCC    2159
Gln Pro Ala Pro Gln Val Gln Gln Pro Gly Leu Val Thr Pro Val Ala
305                     310                     315                 320

CAA GGG ATG GGT TCT GGA GCA CAT ACA GCT GAT CCA GAG AAG CGC AAG    2207
Gln Gly Met Gly Ser Gly Ala His Thr Ala Asp Pro Glu Lys Arg Lys
                325                     330                     335

CTC ATC CAG CAG CAG CTT GTT CTC CTT TTG CAT GCT CAC AAG TGC CAG    2255
Leu Ile Gln Gln Gln Leu Val Leu Leu Leu His Ala His Lys Cys Gln
            340                     345                     350

CGC CGG GAA CAG GCC AAT GGG GAA GTG AGG CAG TGC AAC CTT CCC CAC    2303
Arg Arg Glu Gln Ala Asn Gly Glu Val Arg Gln Cys Asn Leu Pro His
            355                     360                     365

TGT CGC ACA ATG AAG AAT GTC CTA AAC CAC ATG ACA CAC TGC CAG TCA    2351
Cys Arg Thr Met Lys Asn Val Leu Asn His Met Thr His Cys Gln Ser
    370                     375                     380

GGC AAG TCT TGC CAA GTG GCA CAC TGT GCA TCT TCT CGA CAA ATC ATT    2399
Gly Lys Ser Cys Gln Val Ala His Cys Ala Ser Ser Arg Gln Ile Ile
385                     390                     395                 400

TCA CAC TGG AAG AAT TGT ACA AGA CAT GAT TGT CCT GTG TGT CTC CCC    2447
```

| | | | | | | | | | | | | | | | | |
|---|---|---|---|---|---|---|---|---|---|---|---|---|---|---|---|---|
| Ser | His | Trp | Lys | Asn<br>405 | Cys | Thr | Arg | His<br>410 | Asp | Cys | Pro | Val | Cys<br>415 | Leu | Pro | |
| CTC | AAA | AAT | GCT | GGT | GAT | AAG | AGA | AAT | CAA | CAG | CCA | ATT | TTG | ACT | GGA | 2495 |
| Leu | Lys | Asn | Ala<br>420 | Gly | Asp | Lys | Arg | Asn<br>425 | Gln | Gln | Pro | Ile | Leu<br>430 | Thr | Gly | |
| GCA | CCC | GTT | GGA | CTT | GGA | AAT | CCT | AGC | TCT | CTA | GGG | GTG | GGT | CAA | CAG | 2543 |
| Ala | Pro | Val<br>435 | Gly | Leu | Gly | Asn | Pro<br>440 | Ser | Ser | Leu | Gly | Val<br>445 | Gly | Gln | Gln | |
| TCT | GCC | CCC | AAC | CTA | AGC | ACT | GTT | AGT | CAG | ATT | GAT | CCC | AGC | TCC | ATA | 2591 |
| Ser | Ala<br>450 | Pro | Asn | Leu | Ser | Thr<br>455 | Val | Ser | Gln | Ile | Asp<br>460 | Pro | Ser | Ser | Ile | |
| GAA | AGA | GCC | TAT | GCA | GCT | CTT | GGA | CTA | CCC | TAT | CAA | GTA | AAT | CAG | ATG | 2639 |
| Glu<br>465 | Arg | Ala | Tyr | Ala | Ala<br>470 | Leu | Gly | Leu | Pro | Tyr<br>475 | Gln | Val | Asn | Gln | Met<br>480 | |
| CCG | ACA | CAA | CCC | CAG | GTG | CAA | GCA | AAG | AAC | CAG | CAG | AAT | CAG | CAG | CCT | 2687 |
| Pro | Thr | Gln | Pro | Gln<br>485 | Val | Gln | Ala | Lys | Asn<br>490 | Gln | Gln | Asn | Gln | Gln<br>495 | Pro | |
| GGG | CAG | TCT | CCC | CAA | GGC | ATG | CGG | CCC | ATG | AGC | AAC | ATG | AGT | GCT | AGT | 2735 |
| Gly | Gln | Ser | Pro<br>500 | Gln | Gly | Met | Arg | Pro<br>505 | Met | Ser | Asn | Met | Ser<br>510 | Ala | Ser | |
| CCT | ATG | GGA | GTA | AAT | GGA | GGT | GTA | GGA | GTT | CAA | ACG | CCG | AGT | CTT | CTT | 2783 |
| Pro | Met | Gly<br>515 | Val | Asn | Gly | Gly | Val<br>520 | Gly | Val | Gln | Thr | Pro<br>525 | Ser | Leu | Leu | |
| TCT | GAC | TCA | ATG | TTG | CAT | TCA | GCC | ATA | AAT | TCT | CAA | AAC | CCA | ATG | ATG | 2831 |
| Ser | Asp<br>530 | Ser | Met | Leu | His | Ser<br>535 | Ala | Ile | Asn | Ser | Gln<br>540 | Asn | Pro | Met | Met | |
| AGT | GAA | AAT | GCC | AGT | GTG | CCC | TCC | CTG | GGT | CCT | ATG | CCA | ACA | GCA | GCT | 2879 |
| Ser<br>545 | Glu | Asn | Ala | Ser | Val<br>550 | Pro | Ser | Leu | Gly | Pro<br>555 | Met | Pro | Thr | Ala | Ala<br>560 | |
| CAA | CCA | TCC | ACT | ACT | GGA | ATT | CGG | AAA | CAG | TGG | CAC | GAA | GAT | ATT | ACT | 2927 |
| Gln | Pro | Ser | Thr | Thr<br>565 | Gly | Ile | Arg | Lys | Gln<br>570 | Trp | His | Glu | Asp | Ile<br>575 | Thr | |
| CAG | GAT | CTT | CGA | AAT | CAT | CTT | GTT | CAC | AAA | CTC | GTC | CAA | GCC | ATA | TTT | 2975 |
| Gln | Asp | Leu | Arg<br>580 | Asn | His | Leu | Val<br>585 | His | Lys | Leu | Val | Gln<br>590 | Ala | Ile | Phe | |
| CCT | ACG | CCG | GAT | CCT | GCT | GCT | TTA | AAA | GAC | AGA | CGG | ATG | GAA | AAC | CTA | 3023 |
| Pro | Thr | Pro<br>595 | Asp | Pro | Ala | Ala | Leu<br>600 | Lys | Asp | Arg | Arg | Met<br>605 | Glu | Asn | Leu | |
| GTT | GCA | TAT | GCT | CGG | AAA | GTT | GAA | GGG | GAC | ATG | TAT | GAA | TCT | GCA | AAC | 3071 |
| Val | Ala<br>610 | Tyr | Ala | Arg | Lys | Val<br>615 | Glu | Gly | Asp | Met | Tyr<br>620 | Glu | Ser | Ala | Asn | |
| AAT | CGA | GCG | GAA | TAC | TAC | CAC | CTT | CTA | GCT | GAG | AAA | ATC | TAT | AAG | ATC | 3119 |
| Asn<br>625 | Arg | Ala | Glu | Tyr | Tyr<br>630 | His | Leu | Leu | Ala | Glu<br>635 | Lys | Ile | Tyr | Lys | Ile<br>640 | |
| CAG | AAA | GAA | CTA | GAA | GAA | AAA | CGA | AGG | ACC | AGA | CTA | CAG | AAG | CAG | AAC | 3167 |
| Gln | Lys | Glu | Leu | Glu<br>645 | Glu | Lys | Arg | Arg | Thr<br>650 | Arg | Leu | Gln | Lys | Gln<br>655 | Asn | |
| ATG | CTA | CCA | AAT | GCT | GCA | GGC | ATG | GTT | CCA | GTT | TCC | ATG | AAT | CCA | GGG | 3215 |
| Met | Leu | Pro | Asn<br>660 | Ala | Ala | Gly | Met | Val<br>665 | Pro | Val | Ser | Met | Asn<br>670 | Pro | Gly | |
| CCT | AAC | ATG | GGA | CAG | CCG | CAA | CCA | GGA | ATG | ACT | TCT | AAT | GGC | CCT | CTA | 3263 |
| Pro | Asn | Met<br>675 | Gly | Gln | Pro | Gln<br>680 | Gly | Met | Thr | Ser | Asn<br>685 | Gly | Pro | Leu | | |
| CCT | GAC | CCA | AGT | ATG | ATC | CGT | GGC | AGT | GTG | CCA | AAC | CAG | ATG | ATG | CCT | 3311 |
| Pro | Asp<br>690 | Pro | Ser | Met | Ile | Arg<br>695 | Gly | Ser | Val | Pro | Asn<br>700 | Gln | Met | Met | Pro | |
| CGA | ATA | ACT | CCA | CAA | TCT | GGT | TTG | AAT | CAA | TTT | GGC | CAG | ATG | AGC | ATG | 3359 |
| Arg<br>705 | Ile | Thr | Pro | Gln | Ser<br>710 | Gly | Leu | Asn | Gln | Phe<br>715 | Gly | Gln | Met | Ser | Met<br>720 | |
| GCC | CAG | CCC | CCT | ATT | GTA | CCC | CGG | CAA | ACC | CCT | CCT | CTT | CAG | CAC | CAT | 3407 |

| | | | | | | | | | | | | | | | |
|---|---|---|---|---|---|---|---|---|---|---|---|---|---|---|---|
| Ala | Gln | Pro | Pro | Ile 725 | Val | Pro | Arg | Thr 730 | Pro | Pro | Leu | Gln | His 735 | His | |
| GGA | CAG | TTG | GCT | CAA | CCT | GGA | GCT | CTC | AAC | CCG | CCT | ATG | GGC | TAT | GGG | 3455 |
| Gly | Gln | Leu | Ala 740 | Gln | Pro | Gly | Ala | Leu 745 | Asn | Pro | Pro | Met | Gly 750 | Tyr | Gly |
| CCT | CGT | ATG | CAA | CAG | CCT | TCC | AAC | CAG | GGC | CAG | TTC | CTT | CCT | CAG | ACT | 3503 |
| Pro | Arg | Met 755 | Gln | Gln | Pro | Ser | Asn 760 | Gln | Gly | Gln | Phe | Leu 765 | Pro | Gln | Thr |
| CAG | TTC | CCA | TCA | CAG | GGA | ATG | AAT | GTA | ACA | AAT | ATC | CCT | TTG | GCT | CCG | 3551 |
| Gln | Phe 770 | Pro | Ser | Gln | Gly | Met 775 | Asn | Val | Thr | Asn | Ile 780 | Pro | Leu | Ala | Pro |
| TCC | AGC | GGT | CAA | GCT | CCA | GTG | TCT | CAA | GCA | CAA | ATG | TCT | AGT | TCT | TCC | 3599 |
| Ser 785 | Ser | Gly | Gln | Ala | Pro 790 | Val | Ser | Gln | Ala | Gln 795 | Met | Ser | Ser | Ser | Ser 800 |
| TGC | CCG | GTG | AAC | TCT | CCT | ATA | ATG | CCT | CCA | GGG | TCT | CAG | GGG | AGC | CAC | 3647 |
| Cys | Pro | Val | Asn | Ser 805 | Pro | Ile | Met | Pro | Pro 810 | Gly | Ser | Gln | Gly | Ser 815 | His |
| ATT | CAC | TGT | CCC | CAG | CTT | CCT | CAA | CCA | GCT | CTT | CAT | CAG | AAT | TCA | CCC | 3695 |
| Ile | His | Cys | Pro 820 | Gln | Leu | Pro | Gln | Pro 825 | Ala | Leu | His | Gln | Asn 830 | Ser | Pro |
| TCG | CCT | GTA | CCT | AGT | CGT | ACC | CCC | ACC | CCT | CAC | CAT | ACT | CCC | CCA | AGC | 3743 |
| Ser | Pro | Val 835 | Pro | Ser | Arg | Thr | Pro 840 | Thr | Pro | His | His | Thr 845 | Pro | Pro | Ser |
| ATA | GGG | GCT | CAG | CAG | CCA | CCA | GCA | ACA | ACA | ATT | CCA | GCC | CCT | GTT | CCT | 3791 |
| Ile | Gly | Ala 850 | Gln | Gln | Pro | Pro | Ala 855 | Thr | Thr | Ile | Pro | Ala 860 | Pro | Val | Pro |
| ACA | CCA | CCA | GCC | ATG | CCA | CCT | GGG | CCA | CAG | TCC | CAG | GCT | CTA | CAT | CCC | 3839 |
| Thr 865 | Pro | Pro | Ala | Met | Pro 870 | Pro | Gly | Pro | Gln | Ser 875 | Gln | Ala | Leu | His | Pro 880 |
| CCT | CCA | AGG | CAG | ACA | CCT | ACA | CCA | CCA | ACA | ACA | CAA | CTT | CCC | CAA | CAA | 3887 |
| Pro | Pro | Arg | Gln | Thr 885 | Pro | Thr | Pro | Pro | Thr 890 | Thr | Gln | Leu | Pro | Gln 895 | Gln |
| GTG | CAG | CCT | TCA | CTT | CCT | GCT | GCA | CCT | TCT | GCT | GAC | CAG | CCC | CAG | CAG | 3935 |
| Val | Gln | Pro | Ser 900 | Leu | Pro | Ala | Ala | Pro 905 | Ser | Ala | Asp | Gln | Pro 910 | Gln | Gln |
| CAG | CCT | CGC | TCA | CAG | CAG | AGC | ACA | GCA | GCG | TCT | GTT | CCT | ACC | CCA | AAC | 3983 |
| Gln | Pro | Arg 915 | Ser | Gln | Gln | Ser | Thr 920 | Ala | Ala | Ser | Val | Pro 925 | Thr | Pro | Asn |
| GCA | CCG | CTG | CTT | CCT | CCG | CAG | CCT | GCA | ACT | CCA | CTT | TCC | CAG | CCA | GCT | 4031 |
| Ala | Pro | Leu 930 | Leu | Pro | Pro | Gln | Pro 935 | Ala | Thr | Pro | Leu | Ser 940 | Gln | Pro | Ala |
| GTA | AGC | ATT | GAA | GGA | CAG | GTA | TCA | AAT | CCT | CCA | TCT | ACT | AGT | AGC | ACA | 4079 |
| Val 945 | Ser | Ile | Glu | Gly | Gln 950 | Val | Ser | Asn | Pro | Pro 955 | Ser | Thr | Ser | Ser | Thr 960 |
| GAA | GTG | AAT | TCT | CAG | GCC | ATT | GCT | GAG | AAG | CAG | CCT | TCC | CAG | GAA | GTG | 4127 |
| Glu | Val | Asn | Ser | Gln 965 | Ala | Ile | Ala | Glu | Lys 970 | Gln | Pro | Ser | Gln | Glu 975 | Val |
| AAG | ATG | GAG | GCC | AAA | ATG | GAA | GTG | GAT | CAA | CCA | GAA | CCA | GCA | GAT | ACG | 4175 |
| Lys | Met | Glu | Ala 980 | Lys | Met | Glu | Val | Asp 985 | Gln | Pro | Glu | Pro | Ala 990 | Asp | Thr |
| CAG | CCG | GAG | GAT | ATT | TCA | GAG | TCT | AAA | GTG | GAA | GAC | TGT | AAA | ATG | GAA | 4223 |
| Gln | Pro | Glu | Asp 995 | Ile | Ser | Glu | Ser | Lys 1000 | Val | Glu | Asp | Cys | Lys 1005 | Met | Glu |
| TCT | ACC | GAA | ACA | GAA | GAG | AGA | AGC | ACT | GAG | TTA | AAA | ACT | GAA | ATA | AAA | 4271 |
| Ser | Thr | Glu 1010 | Thr | Glu | Glu | Arg | Ser 1015 | Thr | Glu | Leu | Lys | Thr 1020 | Glu | Ile | Lys |
| GAG | GAG | GAA | GAC | CAG | CCA | AGT | ACT | TCA | GCT | ACC | CAG | TCA | TCT | CCG | GCT | 4319 |
| Glu 1025 | Glu | Glu | Asp | Gln | Pro 1030 | Ser | Thr | Ser | Ala | Thr 1035 | Gln | Ser | Ser | Pro | Ala 1040 |
| CCA | GGA | CAG | TCA | AAG | AAA | AAG | ATT | TTC | AAA | CCA | GAA | GAA | CTA | CGA | CAG | 4367 |

|  |  |
|---|---|
| Pro Gly Gln Ser Lys Lys Lys Ile Phe Lys Pro Glu Glu Leu Arg Gln<br>                1045                          1050                        1055 |  |
| GCA CTG ATG CCA ACA TTG GAG GCA CTT TAC CGT CAG GAT CCA GAA TCC<br>Ala Leu Met Pro Thr Leu Glu Ala Leu Tyr Arg Gln Asp Pro Glu Ser<br>            1060                       1065                     1070 | 4415 |
| CTT CCC TTT CGT CAA CCT GTG GAC CCT CAG CTT TTA GGA ATC CCT GAT<br>Leu Pro Phe Arg Gln Pro Val Asp Pro Gln Leu Leu Gly Ile Pro Asp<br>            1075                       1080                     1085 | 4463 |
| TAC TTT GAT ATT GTG AAG AGC CCC ATG GAT CTT TCT ACC ATT AAG AGG<br>Tyr Phe Asp Ile Val Lys Ser Pro Met Asp Leu Ser Thr Ile Lys Arg<br>            1090                       1095                     1100 | 4511 |
| AAG TTA GAC ACT GGA CAG TAT CAG GAG CCC TGG CAG TAT GTC GAT GAT<br>Lys Leu Asp Thr Gly Gln Tyr Gln Glu Pro Trp Gln Tyr Val Asp Asp<br>1105                    1110                       1115                     1120 | 4559 |
| ATT TGG CTT ATG TTC AAT AAT GCC TGG TTA TAT AAC CGG AAA ACA TCA<br>Ile Trp Leu Met Phe Asn Asn Ala Trp Leu Tyr Asn Arg Lys Thr Ser<br>                       1125                       1130                     1135 | 4607 |
| CGG GTA TAC AAA TAC TGC TCC AAG CTC TCT GAG GTC TTT GAA CAA GAA<br>Arg Val Tyr Lys Tyr Cys Ser Lys Leu Ser Glu Val Phe Glu Gln Glu<br>            1140                       1145                     1150 | 4655 |
| ATT GAC CCA GTG ATG CAA AGC CTT GGA TAC TGT TGT GGC AGA AAG TTG<br>Ile Asp Pro Val Met Gln Ser Leu Gly Tyr Cys Cys Gly Arg Lys Leu<br>            1155                       1160                     1165 | 4703 |
| GAG TTC TCT CCA CAG ACA CTG TGT TGC TAC GGC AAA CAG TTG TGC ACA<br>Glu Phe Ser Pro Gln Thr Leu Cys Cys Tyr Gly Lys Gln Leu Cys Thr<br>            1170                       1175                     1180 | 4751 |
| ATA CCT CGT GAT GCC ACT TAT TAC AGT TAC CAG AAC AGG TAT CAT TTC<br>Ile Pro Arg Asp Ala Thr Tyr Tyr Ser Tyr Gln Asn Arg Tyr His Phe<br>1185                    1190                       1195                     1200 | 4799 |
| TGT GAG AAG TGT TTC AAT GAG ATC CAA GGG GAG AGC GTT TCT TTG GGG<br>Cys Glu Lys Cys Phe Asn Glu Ile Gln Gly Glu Ser Val Ser Leu Gly<br>            1205                       1210                     1215 | 4847 |
| GAT GAC CCT TCC CAG CCT CAA ACT ACA ATA AAT AAA GAA CAA TTT TCC<br>Asp Asp Pro Ser Gln Pro Gln Thr Thr Ile Asn Lys Glu Gln Phe Ser<br>            1220                       1225                     1230 | 4895 |
| AAG AGA AAA AAT GAC ACA CTG GAT CCT GAA CTG TTT GTT GAA TGT ACA<br>Lys Arg Lys Asn Asp Thr Leu Asp Pro Glu Leu Phe Val Glu Cys Thr<br>            1235                       1240                     1245 | 4943 |
| GAG TGC GGA AGA AAG ATG CAT CAG ATC TGT GTC CTT CAC CAT GAG ATC<br>Glu Cys Gly Arg Lys Met His Gln Ile Cys Val Leu His His Glu Ile<br>            1250                       1255                     1260 | 4991 |
| ATC TGG CCT GCT GGA TTC GTC TGT GAT GGC TGT TTA AAG AAA AGT GCA<br>Ile Trp Pro Ala Gly Phe Val Cys Asp Gly Cys Leu Lys Lys Ser Ala<br>1265                    1270                       1275                     1280 | 5039 |
| CGA ACT AGG AAA GAA AAT AAG TTT TCT GCT AAA AGG TTG CCA TCT ACC<br>Arg Thr Arg Lys Glu Asn Lys Phe Ser Ala Lys Arg Leu Pro Ser Thr<br>                       1285                       1290                     1295 | 5087 |
| AGA CTT GGC ACC TTT CTA GAG AAT CGT GTG AAT GAC TTT CTG AGG CGA<br>Arg Leu Gly Thr Phe Leu Glu Asn Arg Val Asn Asp Phe Leu Arg Arg<br>            1300                       1305                     1310 | 5135 |
| CAG AAT CAC CCT GAG TCA GGA GAG GTC ACT GTT AGA GTA GTT CAT GCT<br>Gln Asn His Pro Glu Ser Gly Glu Val Thr Val Arg Val Val His Ala<br>            1315                       1320                     1325 | 5183 |
| TCT GAC AAA ACC GTG GAA GTA AAA CCA GGC ATG AAA GCA AGG TTT GTG<br>Ser Asp Lys Thr Val Glu Val Lys Pro Gly Met Lys Ala Arg Phe Val<br>            1330                       1335                     1340 | 5231 |
| GAC AGT GGA GAG ATG GCA GAA TCC TTT CCA TAC CGA ACC AAA GCC CTC<br>Asp Ser Gly Glu Met Ala Glu Ser Phe Pro Tyr Arg Thr Lys Ala Leu<br>1345                    1350                       1355                     1360 | 5279 |
| TTT GCC TTT GAA GAA ATT GAT GGT GTT GAC CTG TGC TTC TTT GGC ATG | 5327 |

```
Phe Ala Phe Glu Glu Ile Asp Gly Val Asp Leu Cys Phe Phe Gly Met
        1365                1370                1375

CAT GTT CAA GAG TAT GGC TCT GAC TGC CCT CCA CCC AAC CAG AGG AGA    5375
His Val Gln Glu Tyr Gly Ser Asp Cys Pro Pro Pro Asn Gln Arg Arg
        1380                1385                1390

GTA TAC ATA TCT TAC CTC GAT AGT GTT CAT TTC TTC CGT CCT AAA TGC    5423
Val Tyr Ile Ser Tyr Leu Asp Ser Val His Phe Phe Arg Pro Lys Cys
        1395                1400                1405

TTG AGG ACT GCA GTC TAT CAT GAA ATC CTA ATT GGA TAT TTA GAA TAT    5471
Leu Arg Thr Ala Val Tyr His Glu Ile Leu Ile Gly Tyr Leu Glu Tyr
        1410                1415                1420

GTC AAG AAA TTA GGT TAC ACA ACA GGG CAT ATT TGG GCA TGT CCA CCA    5519
Val Lys Lys Leu Gly Tyr Thr Thr Gly His Ile Trp Ala Cys Pro Pro
1425                1430                1435                1440

AGT GAG GGA GAT GAT TAT ATC TTC CAT TGC CAT CCT CCT GAC CAG AAG    5567
Ser Glu Gly Asp Asp Tyr Ile Phe His Cys His Pro Pro Asp Gln Lys
                1445                1450                1455

ATA CCC AAG CCC AAG CGA CTG CAG GAA TGG TAC AAA AAA ATG CTT GAC    5615
Ile Pro Lys Pro Lys Arg Leu Gln Glu Trp Tyr Lys Lys Met Leu Asp
        1460                1465                1470

AAG GCT GTA TCA GAG CGT ATT GTC CAT GAC TAC AAG GAT ATT TTT AAA    5663
Lys Ala Val Ser Glu Arg Ile Val His Asp Tyr Lys Asp Ile Phe Lys
        1475                1480                1485

CAA GCT ACT GAA GAT AGA TTA ACA AGT GCA AAG GAA TTG CCT TAT TTC    5711
Gln Ala Thr Glu Asp Arg Leu Thr Ser Ala Lys Glu Leu Pro Tyr Phe
        1490                1495                1500

GAG GGT GAT TTC TGG CCC AAT GTT CTG GAA GAA AGC ATT AAG GAA CTG    5759
Glu Gly Asp Phe Trp Pro Asn Val Leu Glu Glu Ser Ile Lys Glu Leu
1505                1510                1515                1520

GAA CAG GAG GAA GAA GAG AGA AAA CGA GAG GAA AAC ACC AGC AAT GAA    5807
Glu Gln Glu Glu Glu Glu Arg Lys Arg Glu Glu Asn Thr Ser Asn Glu
                1525                1530                1535

AGC ACA GAT GTG ACC AAG GGA GAC AGC AAA AAT GCT AAA AAG AAG AAT    5855
Ser Thr Asp Val Thr Lys Gly Asp Ser Lys Asn Ala Lys Lys Lys Asn
        1540                1545                1550

AAT AAG AAA ACC AGC AAA AAT AAG AGC AGC CTG AGT AGG GGC AAC AAG    5903
Asn Lys Lys Thr Ser Lys Asn Lys Ser Ser Leu Ser Arg Gly Asn Lys
        1555                1560                1565

AAG AAA CCC GGG ATG CCC AAT GTA TCT AAC GAC CTC TCA CAG AAA CTA    5951
Lys Lys Pro Gly Met Pro Asn Val Ser Asn Asp Leu Ser Gln Lys Leu
        1570                1575                1580

TAT GCC ACC ATG GAG AAG CAT AAA GAG GTC TTC TTT GTG ATC CGC CTC    5999
Tyr Ala Thr Met Glu Lys His Lys Glu Val Phe Phe Val Ile Arg Leu
1585                1590                1595                1600

ATT GCT GGC CCT GCT GCC AAC TCC CTG CCT CCC ATT GTT GAT CCT GAT    6047
Ile Ala Gly Pro Ala Ala Asn Ser Leu Pro Pro Ile Val Asp Pro Asp
                1605                1610                1615

CCT CTC ATC CCC TGC GAT CTG ATG GAT GGT CGG GAT GCG TTT CTC ACG    6095
Pro Leu Ile Pro Cys Asp Leu Met Asp Gly Arg Asp Ala Phe Leu Thr
        1620                1625                1630

CTG GCA AGG GAC AAG CAC CTG GAG TTC TCT TCA CTC CGA AGA GCC CAG    6143
Leu Ala Arg Asp Lys His Leu Glu Phe Ser Ser Leu Arg Arg Ala Gln
        1635                1640                1645

TGG TCC ACC ATG TGC ATG CTG GTG GAG CTG CAC ACG CAG AGC CAG GAC    6191
Trp Ser Thr Met Cys Met Leu Val Glu Leu His Thr Gln Ser Gln Asp
        1650                1655                1660

CGC TTT GTC TAC ACC TGC AAT GAA TGC AAG CAC CAT GTG GAG ACA CGC    6239
Arg Phe Val Tyr Thr Cys Asn Glu Cys Lys His His Val Glu Thr Arg
1665                1670                1675                1680

TGG CAC TGT ACT GTC TGT GAG GAT TAT GAC TTG TGT ATC ACC TGC TAT    6287
```

-continued

| | | | | | | | | | | | | | | | |
|---|---|---|---|---|---|---|---|---|---|---|---|---|---|---|---|
| Trp | His | Cys | Thr | Val | Cys | Glu | Asp | Tyr | Asp | Leu | Cys | Ile | Thr | Cys | Tyr |
| | | 1685 | | | | 1690 | | | | | 1695 | | | | |

```
AAC ACT AAA AAC CAT GAC CAC AAA ATG GAG AAA CTA GGC CTT GGC TTA      6335
Asn Thr Lys Asn His Asp His Lys Met Glu Lys Leu Gly Leu Gly Leu
        1700                1705                1710

GAT GAT GAG AGC AAC AAC CAG CAG GCT GCA GCC ACC CAG AGC CCA GGC      6383
Asp Asp Glu Ser Asn Asn Gln Gln Ala Ala Ala Thr Gln Ser Pro Gly
        1715                1720                1725

GAT TCT CGC CGC CTG AGT ATC CAG CGC TGC ATC CAG TCT CTG GTC CAT      6431
Asp Ser Arg Arg Leu Ser Ile Gln Arg Cys Ile Gln Ser Leu Val His
        1730                1735                1740

GCT TGC CAG TGT CGG AAT GCC AAT TGC TCA CTG CCA TCC TGC CAG AAG      6479
Ala Cys Gln Cys Arg Asn Ala Asn Cys Ser Leu Pro Ser Cys Gln Lys
1745                1750                1755                1760

ATG AAG CGG GTT GTG CAG CAT ACC AAG GGT TGC AAA CGG AAA ACC AAT      6527
Met Lys Arg Val Val Gln His Thr Lys Gly Cys Lys Arg Lys Thr Asn
        1765                1770                1775

GGC GGG TGC CCC ATC TGC AAG CAG CTC ATT GCC CTC TGC TGC TAC CAT      6575
Gly Gly Cys Pro Ile Cys Lys Gln Leu Ile Ala Leu Cys Cys Tyr His
        1780                1785                1790

GCC AAG CAC TGC CAG GAG AAC AAA TGC CCG GTG CCG TTC TGC CTA AAC      6623
Ala Lys His Cys Gln Glu Asn Lys Cys Pro Val Pro Phe Cys Leu Asn
        1795                1800                1805

ATC AAG CAG AAG CTC CGG CAG CAA CAG CTG CAG CAC CGA CTA CAG CAG      6671
Ile Lys Gln Lys Leu Arg Gln Gln Gln Leu Gln His Arg Leu Gln Gln
1810                1815                1820

GCC CAA ATG CTT CGC AGG AGG ATG GCC AGC ATG CAG CGG ACT GGT GTG      6719
Ala Gln Met Leu Arg Arg Arg Met Ala Ser Met Gln Arg Thr Gly Val
1825                1830                1835                1840

GTT GGG CAG CAA CAG GGC CTC CCT TCC CCC ACT CCT GCC ACT CCA ACG      6767
Val Gly Gln Gln Gln Gly Leu Pro Ser Pro Thr Pro Ala Thr Pro Thr
        1845                1850                1855

ACA CCA ACT GGC CAA CAG CCA ACC ACC CCG CAG ACG CCC CAG CCC ACT      6815
Thr Pro Thr Gly Gln Gln Pro Thr Thr Pro Gln Thr Pro Gln Pro Thr
        1860                1865                1870

TCT CAG CCT CAG CCT ACC CCT CCC AAT AGC ATG CCA CCC TAC TTG CCC      6863
Ser Gln Pro Gln Pro Thr Pro Pro Asn Ser Met Pro Pro Tyr Leu Pro
        1875                1880                1885

AGG ACT CAA GCT GCT GGC CCT GTG TCC CAG GGT AAG GCA GCA GGC CAG      6911
Arg Thr Gln Ala Ala Gly Pro Val Ser Gln Gly Lys Ala Ala Gly Gln
        1890                1895                1900

GTG ACC CCT CCA ACC CCT CCT CAG ACT GCT CAG CCA CCC CTT CCA GGG      6959
Val Thr Pro Pro Thr Pro Pro Gln Thr Ala Gln Pro Pro Leu Pro Gly
1905                1910                1915                1920

CCC CCA CCT ACA GCA GTG GAA ATG GCA ATG CAG ATT CAG AGA GCA GCG      7007
Pro Pro Pro Thr Ala Val Glu Met Ala Met Gln Ile Gln Arg Ala Ala
                1925                1930                1935

GAG ACG CAG CGC CAG ATG GCC CAC GTG CAA ATT TTT CAA AGG CCA ATC      7055
Glu Thr Gln Arg Gln Met Ala His Val Gln Ile Phe Gln Arg Pro Ile
        1940                1945                1950

CAA CAC CAG ATG CCC CCG ATG ACT CCC ATG GCC CCC ATG GGT ATG AAC      7103
Gln His Gln Met Pro Pro Met Thr Pro Met Ala Pro Met Gly Met Asn
        1955                1960                1965

CCA CCT CCC ATG ACC AGA GGT CCC AGT GGG CAT TTG GAG CCA GGG ATG      7151
Pro Pro Pro Met Thr Arg Gly Pro Ser Gly His Leu Glu Pro Gly Met
        1970                1975                1980

GGA CCG ACA GGG ATG CAG CAA CAG CCA CCC TGG AGC CAA GGA GGA TTG      7199
Gly Pro Thr Gly Met Gln Gln Gln Pro Pro Trp Ser Gln Gly Gly Leu
1985                1990                1995                2000

CCT CAG CCC CAG CAA CTA CAG TCT GGG ATG CCA AGG CCA GCC ATG ATG      7247
```

|  |  |
|---|---|
| Pro Gln Pro Gln Gln Leu Gln Ser Gly Met Pro Arg Pro Ala Met Met<br>                     2005                            2010                         2015 |  |
| TCA GTG GCC CAG CAT GGT CAA CCT TTG AAC ATG GCT CCA CAA CCA GGA<br>Ser Val Ala Gln His Gly Gln Pro Leu Asn Met Ala Pro Gln Pro Gly<br>         2020                         2025                        2030 | 7295 |
| TTG GGC CAG GTA GGT ATC AGC CCA CTC AAA CCA GGC ACT GTG TCT CAA<br>Leu Gly Gln Val Gly Ile Ser Pro Leu Lys Pro Gly Thr Val Ser Gln<br>         2035                       2040                      2045 | 7343 |
| CAA GCC TTA CAA AAC CTT TTG CGG ACT CTC AGG TCT CCC AGC TCT CCC<br>Gln Ala Leu Gln Asn Leu Leu Arg Thr Leu Arg Ser Pro Ser Ser Pro<br>2050                       2055                      2060 | 7391 |
| CTG CAG CAG CAA CAG GTG CTT AGT ATC CTT CAC GCC AAC CCC CAG CTG<br>Leu Gln Gln Gln Gln Val Leu Ser Ile Leu His Ala Asn Pro Gln Leu<br>2065                       2070                      2075                     2080 | 7439 |
| TTG GCT GCA TTC ATC AAG CAG CGG GCT GCC AAG TAT GCC AAC TCT AAT<br>Leu Ala Ala Phe Ile Lys Gln Arg Ala Ala Lys Tyr Ala Asn Ser Asn<br>         2085                       2090                      2095 | 7487 |
| CCA CAA CCC ATC CCT GGG CAG CCT GGC ATG CCC CAG GGG CAG CCA GGG<br>Pro Gln Pro Ile Pro Gly Gln Pro Gly Met Pro Gln Gly Gln Pro Gly<br>         2100                       2105                      2110 | 7535 |
| CTA CAG CCA CCT ACC ATG CCA GGT CAG CAG GGG GTC CAC TCC AAT CCA<br>Leu Gln Pro Pro Thr Met Pro Gly Gln Gln Gly Val His Ser Asn Pro<br>         2115                       2120                      2125 | 7583 |
| GCC ATG CAG AAC ATG AAT CCA ATG CAG GCG GGC GTT CAG AGG GCT GGC<br>Ala Met Gln Asn Met Asn Pro Met Gln Ala Gly Val Gln Arg Ala Gly<br>         2130                       2135                      2140 | 7631 |
| CTG CCC CAG CAG CAA CCA CAG CAG CAA CTC CAG CCA CCC ATG GGA GGG<br>Leu Pro Gln Gln Gln Pro Gln Gln Leu Gln Pro Pro Met Gly Gly<br>2145                       2150                      2155                     2160 | 7679 |
| ATG AGC CCC CAG GCT CAG CAG ATG AAC ATG AAC CAC AAC ACC ATG CCT<br>Met Ser Pro Gln Ala Gln Gln Met Asn Met Asn His Asn Thr Met Pro<br>                 2165                       2170                      2175 | 7727 |
| TCA CAA TTC CGA GAC ATC TTG AGA CGA CAG CAA ATG ATG CAA CAG CAG<br>Ser Gln Phe Arg Asp Ile Leu Arg Arg Gln Gln Met Met Gln Gln Gln<br>         2180                       2185                      2190 | 7775 |
| CAG CAA CAG GGA GCA GGG CCA GGA ATA GGC CCT GGA ATG GCC AAC CAT<br>Gln Gln Gln Gly Ala Gly Pro Gly Ile Gly Pro Gly Met Ala Asn His<br>         2195                       2200                      2205 | 7823 |
| AAC CAG TTC CAG CAA CCC CAA GGA GTT GGC TAC CCA CCA CAG CCG CAG<br>Asn Gln Phe Gln Gln Pro Gln Gly Val Gly Tyr Pro Pro Gln Pro Gln<br>         2210                       2215                      2220 | 7871 |
| CAG CGG ATG CAG CAT CAC ATG CAA CAG ATG CAA CAA GGA AAT ATG GGA<br>Gln Arg Met Gln His His Met Gln Gln Met Gln Gln Gly Asn Met Gly<br>2225                       2230                      2235                     2240 | 7919 |
| CAG ATA GGC CAG CTT CCC CAG GCC TTG GGA GCA GAG GCA GGT GCC AGT<br>Gln Ile Gly Gln Leu Pro Gln Ala Leu Gly Ala Glu Ala Gly Ala Ser<br>                 2245                       2250                      2255 | 7967 |
| CTA CAG GCC TAT CAG CAG CGA CTC CTT CAG CAA CAG ATG GGG TCC CCT<br>Leu Gln Ala Tyr Gln Gln Arg Leu Leu Gln Gln Gln Met Gly Ser Pro<br>                 2260                       2265                      2270 | 8015 |
| GTT CAG CCC AAC CCC ATG AGC CCC CAG CAG CAT ATG CTC CCA AAT CAG<br>Val Gln Pro Asn Pro Met Ser Pro Gln Gln His Met Leu Pro Asn Gln<br>         2275                       2280                      2285 | 8063 |
| GCC CAG TCC CCA CAC CTA CAA GGC CAG CAG ATC CCT AAT TCT CTC TCC<br>Ala Gln Ser Pro His Leu Gln Gly Gln Gln Ile Pro Asn Ser Leu Ser<br>2290                       2295                      2300 | 8111 |
| AAT CAA GTG CGC TCT CCC CAG CCT GTC CCT TCT CCA CGG CCA CAG TCC<br>Asn Gln Val Arg Ser Pro Gln Pro Val Pro Ser Pro Arg Pro Gln Ser<br>2305                       2310                      2315                     2320 | 8159 |
| CAG CCC CCC CAC TCC AGT CCT TCC CCA AGG ATG CAG CCT CAG CCT TCT | 8207 |

-continued

| | | | | | | | | | | | | | | | |
|---|---|---|---|---|---|---|---|---|---|---|---|---|---|---|---|
| Gln | Pro | Pro | His | Ser | Ser | Pro | Ser | Pro | Arg | Met | Gln | Pro | Gln | Pro | Ser |
| | | | | 2325 | | | | 2330 | | | | | 2335 | | |

```
CCA CAC CAC GTT TCC CCA CAG ACA AGT TCC CCA CAT CCT GGA CTG GTA          8255
Pro His His Val Ser Pro Gln Thr Ser Ser Pro His Pro Gly Leu Val
            2340            2345            2350

GCT GCC CAG GCC AAC CCC ATG GAA CAA GGG CAT TTT GCC AGC CCG GAC          8303
Ala Ala Gln Ala Asn Pro Met Glu Gln Gly His Phe Ala Ser Pro Asp
            2355            2360            2365

CAG AAT TCA ATG CTT TCT CAG CTT GCT AGC AAT CCA GGC ATG GCA AAC          8351
Gln Asn Ser Met Leu Ser Gln Leu Ala Ser Asn Pro Gly Met Ala Asn
            2370            2375            2380

CTC CAT GGT GCA AGC GCC ACG GAC CTG GGA CTC AGC ACC GAT AAC TCA          8399
Leu His Gly Ala Ser Ala Thr Asp Leu Gly Leu Ser Thr Asp Asn Ser
2385            2390            2395            2400

GAC TTG AAT TCA AAC CTC TCA CAG AGT ACA CTA GAC ATA CAC                  8441
Asp Leu Asn Ser Asn Leu Ser Gln Ser Thr Leu Asp Ile His
            2405            2410

TAGAGACACC TTGTATTTTG GGAGCAAAAA AATTATTTTC TCTTAACAAG ACTTTTTGTA        8501
CTGAAAACAA TTTTTTTGAA TCTTTCGTAG CCTAAAAGAC AATTTTCCTT GGAACACATA        8561
AGAACTGTGC AGTAGCCGTT TGTGGTTTAA AGCAAACATG CAAGATGAAC CTGAGGGATG        8621
ATAGAATACA AAGAATATAT TTTGTTATG GGCTGGTTAC CACCAGCCTT TCTTCCCCTT         8681
TGTGTGTGTG GTTCAAGTGT GCACTGGGAG GAGGCTGAGG CCTGTGAAGC CAAACAATAT       8741
GCTCCTGCCT TGCACCTCCA ATAGGTTTTA TTATTTTTT TAAATTAATG AACATATGTA        8801
ATATTAATGA ACATATGTAA TATTAATAGT TATTATTTAC TGGTGCAGAT GGTTGACATT       8861
TTTCCCTATT TTCCTCACTT TATGGAAGAG TTAAAACATT TCTAAACCAG AGGACAAAAG       8921
GGGTTAATGT TACTTTGAAA TTACATTCTA TATATATATA AATATATATA AATATATATT       8981
AAAATACCAG TTTTTTTTCT CTGGGTGCAA AGATGTTCAT TCTTTAAAA AATGTTTAAA        9041
AAAAA                                                                    9046
```

( 2 ) INFORMATION FOR SEQ ID NO:2:

( i ) SEQUENCE CHARACTERISTICS:
        ( A ) LENGTH: 2414 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Glu Asn Val Val Glu Pro Gly Pro Pro Ser Ala Lys Arg Pro
 1               5                  10                  15

Lys Leu Ser Ser Pro Ala Leu Ser Ala Ser Ala Ser Asp Gly Thr Asp
            20                  25                  30

Phe Gly Ser Leu Phe Asp Leu Glu His Asp Leu Pro Asp Glu Leu Ile
            35                  40                  45

Asn Ser Thr Glu Leu Gly Leu Thr Asn Gly Gly Asp Ile Asn Gln Leu
            50                  55                  60

Gln Thr Ser Leu Gly Met Val Gln Asp Ala Ala Ser Lys His Lys Gln
65                  70                  75                  80

Leu Ser Glu Leu Leu Arg Ser Gly Ser Ser Pro Asn Leu Asn Met Gly
            85                  90                  95

Val Gly Gly Pro Gly Gln Val Met Ala Ser Gln Ala Gln Gln Ser Ser
            100                 105                 110

Pro Gly Leu Gly Leu Ile Asn Ser Met Val Lys Ser Pro Met Thr Gln
            115                 120                 125
```

| | | | | | | | | | | | | | |
|---|---|---|---|---|---|---|---|---|---|---|---|---|---|
| Ala | Gly | Leu | Thr | Ser | Pro | Asn | Met | Gly | Met | Gly | Thr | Ser | Gly | Pro | Asn |
| | 130 | | | | | 135 | | | | 140 | | | |
| Gln | Gly | Pro | Thr | Gln | Ser | Thr | Gly | Met | Met | Asn | Ser | Pro | Val | Asn | Gln |
| 145 | | | | | 150 | | | | | 155 | | | | | 160 |
| Pro | Ala | Met | Gly | Met | Asn | Thr | Gly | Thr | Asn | Ala | Gly | Met | Asn | Pro | Gly |
| | | | | 165 | | | | | 170 | | | | | 175 | |
| Met | Leu | Ala | Ala | Gly | Asn | Gly | Gln | Gly | Ile | Met | Pro | Asn | Gln | Val | Met |
| | | | 180 | | | | | 185 | | | | | 190 | | |
| Asn | Gly | Ser | Ile | Gly | Ala | Gly | Arg | Gly | Arg | Gln | Asp | Met | Gln | Tyr | Pro |
| | | 195 | | | | | 200 | | | | | 205 | | | |
| Asn | Pro | Gly | Met | Gly | Ser | Ala | Gly | Asn | Leu | Leu | Thr | Glu | Pro | Leu | Gln |
| | 210 | | | | | 215 | | | | | 220 | | | | |
| Gln | Gly | Ser | Pro | Gln | Met | Gly | Gly | Gln | Thr | Gly | Leu | Arg | Gly | Pro | Gln |
| 225 | | | | | 230 | | | | | 235 | | | | | 240 |
| Pro | Leu | Lys | Met | Gly | Met | Met | Asn | Asn | Pro | Asn | Pro | Tyr | Gly | Ser | Pro |
| | | | | 245 | | | | | 250 | | | | | 255 | |
| Tyr | Thr | Gln | Asn | Pro | Gly | Gln | Gln | Ile | Gly | Ala | Ser | Gly | Leu | Gly | Leu |
| | | | 260 | | | | | 265 | | | | | 270 | | |
| Gln | Ile | Gln | Thr | Lys | Thr | Val | Leu | Ser | Asn | Asn | Leu | Ser | Pro | Phe | Ala |
| | | 275 | | | | | 280 | | | | | 285 | | | |
| Met | Asp | Lys | Lys | Ala | Val | Pro | Gly | Gly | Gly | Met | Pro | Asn | Met | Gly | Gln |
| | 290 | | | | | 295 | | | | | 300 | | | | |
| Gln | Pro | Ala | Pro | Gln | Val | Gln | Gln | Pro | Gly | Leu | Val | Thr | Pro | Val | Ala |
| 305 | | | | | 310 | | | | | 315 | | | | | 320 |
| Gln | Gly | Met | Gly | Ser | Gly | Ala | His | Thr | Ala | Asp | Pro | Glu | Lys | Arg | Lys |
| | | | | 325 | | | | | 330 | | | | | 335 | |
| Leu | Ile | Gln | Gln | Gln | Leu | Val | Leu | Leu | Leu | His | Ala | His | Lys | Cys | Gln |
| | | | 340 | | | | | 345 | | | | | 350 | | |
| Arg | Arg | Glu | Gln | Ala | Asn | Gly | Glu | Val | Arg | Gln | Cys | Asn | Leu | Pro | His |
| | | 355 | | | | | 360 | | | | | 365 | | | |
| Cys | Arg | Thr | Met | Lys | Asn | Val | Leu | Asn | His | Met | Thr | His | Cys | Gln | Ser |
| | 370 | | | | | 375 | | | | | 380 | | | | |
| Gly | Lys | Ser | Cys | Gln | Val | Ala | His | Cys | Ala | Ser | Ser | Arg | Gln | Ile | Ile |
| 385 | | | | | 390 | | | | | 395 | | | | | 400 |
| Ser | His | Trp | Lys | Asn | Cys | Thr | Arg | His | Asp | Cys | Pro | Val | Cys | Leu | Pro |
| | | | | 405 | | | | | 410 | | | | | 415 | |
| Leu | Lys | Asn | Ala | Gly | Asp | Lys | Arg | Asn | Gln | Gln | Pro | Ile | Leu | Thr | Gly |
| | | | 420 | | | | | 425 | | | | | 430 | | |
| Ala | Pro | Val | Gly | Leu | Gly | Asn | Pro | Ser | Ser | Leu | Gly | Val | Gly | Gln | Gln |
| | | 435 | | | | | 440 | | | | | 445 | | | |
| Ser | Ala | Pro | Asn | Leu | Ser | Thr | Val | Ser | Gln | Ile | Asp | Pro | Ser | Ser | Ile |
| | 450 | | | | | 455 | | | | | 460 | | | | |
| Glu | Arg | Ala | Tyr | Ala | Ala | Leu | Gly | Leu | Pro | Tyr | Gln | Val | Asn | Gln | Met |
| 465 | | | | | 470 | | | | | 475 | | | | | 480 |
| Pro | Thr | Gln | Pro | Gln | Val | Gln | Ala | Lys | Asn | Gln | Gln | Asn | Gln | Gln | Pro |
| | | | | 485 | | | | | 490 | | | | | 495 | |
| Gly | Gln | Ser | Pro | Gln | Gly | Met | Arg | Pro | Met | Ser | Asn | Met | Ser | Ala | Ser |
| | | | 500 | | | | | 505 | | | | | 510 | | |
| Pro | Met | Gly | Val | Asn | Gly | Gly | Val | Gly | Val | Gln | Thr | Pro | Ser | Leu | Leu |
| | | 515 | | | | | 520 | | | | | 525 | | | |
| Ser | Asp | Ser | Met | Leu | His | Ser | Ala | Ile | Asn | Ser | Gln | Asn | Pro | Met | Met |
| | 530 | | | | | 535 | | | | | 540 | | | | |
| Ser | Glu | Asn | Ala | Ser | Val | Pro | Ser | Leu | Gly | Pro | Met | Pro | Thr | Ala | Ala |

-continued

|     |     |     |     |     |     |     |     |     |     |     |     |     |     |     |     |
| --- | --- | --- | --- | --- | --- | --- | --- | --- | --- | --- | --- | --- | --- | --- | --- |
| 545 |     |     |     |     | 550 |     |     |     |     | 555 |     |     |     |     | 560 |
| Gln | Pro | Ser | Thr | Thr | Gly | Ile | Arg | Lys | Gln | Trp | His | Glu | Asp | Ile | Thr |
|     |     |     |     | 565 |     |     |     |     | 570 |     |     |     |     | 575 |     |
| Gln | Asp | Leu | Arg | Asn | His | Leu | Val | His | Lys | Leu | Val | Gln | Ala | Ile | Phe |
|     |     |     | 580 |     |     |     |     | 585 |     |     |     |     | 590 |     |     |
| Pro | Thr | Pro | Asp | Pro | Ala | Ala | Leu | Lys | Asp | Arg | Arg | Met | Glu | Asn | Leu |
|     |     | 595 |     |     |     |     | 600 |     |     |     |     | 605 |     |     |     |
| Val | Ala | Tyr | Ala | Arg | Lys | Val | Glu | Gly | Asp | Met | Tyr | Glu | Ser | Ala | Asn |
|     | 610 |     |     |     |     | 615 |     |     |     |     | 620 |     |     |     |     |
| Asn | Arg | Ala | Glu | Tyr | Tyr | His | Leu | Leu | Ala | Glu | Lys | Ile | Tyr | Lys | Ile |
| 625 |     |     |     |     | 630 |     |     |     |     | 635 |     |     |     |     | 640 |
| Gln | Lys | Glu | Leu | Glu | Glu | Lys | Arg | Arg | Thr | Arg | Leu | Gln | Lys | Gln | Asn |
|     |     |     |     | 645 |     |     |     |     | 650 |     |     |     |     | 655 |     |
| Met | Leu | Pro | Asn | Ala | Ala | Gly | Met | Val | Pro | Val | Ser | Met | Asn | Pro | Gly |
|     |     |     | 660 |     |     |     |     | 665 |     |     |     |     | 670 |     |     |
| Pro | Asn | Met | Gly | Gln | Pro | Gln | Pro | Gly | Met | Thr | Ser | Asn | Gly | Pro | Leu |
|     |     | 675 |     |     |     |     | 680 |     |     |     |     | 685 |     |     |     |
| Pro | Asp | Pro | Ser | Met | Ile | Arg | Gly | Ser | Val | Pro | Asn | Gln | Met | Met | Pro |
|     | 690 |     |     |     |     | 695 |     |     |     |     | 700 |     |     |     |     |
| Arg | Ile | Thr | Pro | Gln | Ser | Gly | Leu | Asn | Gln | Phe | Gly | Gln | Met | Ser | Met |
| 705 |     |     |     |     | 710 |     |     |     |     | 715 |     |     |     |     | 720 |
| Ala | Gln | Pro | Pro | Ile | Val | Pro | Arg | Gln | Thr | Pro | Pro | Leu | Gln | His | His |
|     |     |     |     | 725 |     |     |     |     | 730 |     |     |     |     | 735 |     |
| Gly | Gln | Leu | Ala | Gln | Pro | Gly | Ala | Leu | Asn | Pro | Pro | Met | Gly | Tyr | Gly |
|     |     |     | 740 |     |     |     |     | 745 |     |     |     |     | 750 |     |     |
| Pro | Arg | Met | Gln | Gln | Pro | Ser | Asn | Gln | Gly | Gln | Phe | Leu | Pro | Gln | Thr |
|     |     | 755 |     |     |     |     | 760 |     |     |     |     | 765 |     |     |     |
| Gln | Phe | Pro | Ser | Gln | Gly | Met | Asn | Val | Thr | Asn | Ile | Pro | Leu | Ala | Pro |
|     | 770 |     |     |     |     | 775 |     |     |     |     | 780 |     |     |     |     |
| Ser | Ser | Gly | Gln | Ala | Pro | Val | Ser | Gln | Ala | Gln | Met | Ser | Ser | Ser | Ser |
| 785 |     |     |     |     | 790 |     |     |     |     | 795 |     |     |     |     | 800 |
| Cys | Pro | Val | Asn | Ser | Pro | Ile | Met | Pro | Pro | Gly | Ser | Gln | Gly | Ser | His |
|     |     |     |     | 805 |     |     |     |     | 810 |     |     |     |     | 815 |     |
| Ile | His | Cys | Pro | Gln | Leu | Pro | Gln | Pro | Ala | Leu | His | Gln | Asn | Ser | Pro |
|     |     |     | 820 |     |     |     |     | 825 |     |     |     |     | 830 |     |     |
| Ser | Pro | Val | Pro | Ser | Arg | Thr | Pro | Thr | Pro | His | His | Thr | Pro | Pro | Ser |
|     |     | 835 |     |     |     |     | 840 |     |     |     |     | 845 |     |     |     |
| Ile | Gly | Ala | Gln | Gln | Pro | Pro | Ala | Thr | Thr | Ile | Pro | Ala | Pro | Val | Pro |
|     | 850 |     |     |     |     | 855 |     |     |     |     | 860 |     |     |     |     |
| Thr | Pro | Pro | Ala | Met | Pro | Pro | Gly | Pro | Gln | Ser | Gln | Ala | Leu | His | Pro |
| 865 |     |     |     |     | 870 |     |     |     |     | 875 |     |     |     |     | 880 |
| Pro | Pro | Arg | Gln | Thr | Pro | Thr | Pro | Pro | Thr | Thr | Gln | Leu | Pro | Gln | Gln |
|     |     |     |     | 885 |     |     |     |     | 890 |     |     |     |     | 895 |     |
| Val | Gln | Pro | Ser | Leu | Pro | Ala | Ala | Pro | Ser | Ala | Asp | Gln | Pro | Gln | Gln |
|     |     |     | 900 |     |     |     |     | 905 |     |     |     |     | 910 |     |     |
| Gln | Pro | Arg | Ser | Gln | Gln | Ser | Thr | Ala | Ala | Ser | Val | Pro | Thr | Pro | Asn |
|     |     | 915 |     |     |     |     | 920 |     |     |     |     | 925 |     |     |     |
| Ala | Pro | Leu | Leu | Pro | Pro | Gln | Pro | Ala | Thr | Pro | Leu | Ser | Gln | Pro | Ala |
|     | 930 |     |     |     |     | 935 |     |     |     |     | 940 |     |     |     |     |
| Val | Ser | Ile | Glu | Gly | Gln | Val | Ser | Asn | Pro | Pro | Ser | Thr | Ser | Ser | Thr |
| 945 |     |     |     |     | 950 |     |     |     |     | 955 |     |     |     |     | 960 |
| Glu | Val | Asn | Ser | Gln | Ala | Ile | Ala | Glu | Lys | Gln | Pro | Ser | Gln | Glu | Val |
|     |     |     |     | 965 |     |     |     |     | 970 |     |     |     |     | 975 |     |

```
Lys Met Glu Ala Lys Met Glu Val Asp Gln Pro Glu Pro Ala Asp Thr
            980                 985                 990
Gln Pro Glu Asp Ile Ser Glu Ser Lys Val Glu Asp Cys Lys Met Glu
        995                 1000                1005
Ser Thr Glu Thr Glu Glu Arg Ser Thr Glu Leu Lys Thr Glu Ile Lys
    1010                1015                1020
Glu Glu Glu Asp Gln Pro Ser Thr Ser Ala Thr Gln Ser Ser Pro Ala
1025                1030                1035                1040
Pro Gly Gln Ser Lys Lys Lys Ile Phe Lys Pro Glu Glu Leu Arg Gln
                1045                1050                1055
Ala Leu Met Pro Thr Leu Glu Ala Leu Tyr Arg Gln Asp Pro Glu Ser
            1060                1065                1070
Leu Pro Phe Arg Gln Pro Val Asp Pro Gln Leu Leu Gly Ile Pro Asp
        1075                1080                1085
Tyr Phe Asp Ile Val Lys Ser Pro Met Asp Leu Ser Thr Ile Lys Arg
    1090                1095                1100
Lys Leu Asp Thr Gly Gln Tyr Gln Glu Pro Trp Gln Tyr Val Asp Asp
1105                1110                1115                1120
Ile Trp Leu Met Phe Asn Asn Ala Trp Leu Tyr Asn Arg Lys Thr Ser
                1125                1130                1135
Arg Val Tyr Lys Tyr Cys Ser Lys Leu Ser Glu Val Phe Glu Gln Glu
            1140                1145                1150
Ile Asp Pro Val Met Gln Ser Leu Gly Tyr Cys Cys Gly Arg Lys Leu
        1155                1160                1165
Glu Phe Ser Pro Gln Thr Leu Cys Cys Tyr Gly Lys Gln Leu Cys Thr
    1170                1175                1180
Ile Pro Arg Asp Ala Thr Tyr Tyr Ser Tyr Gln Asn Arg Tyr His Phe
1185                1190                1195                1200
Cys Glu Lys Cys Phe Asn Glu Ile Gln Gly Glu Ser Val Ser Leu Gly
                1205                1210                1215
Asp Asp Pro Ser Gln Pro Gln Thr Thr Ile Asn Lys Glu Gln Phe Ser
            1220                1225                1230
Lys Arg Lys Asn Asp Thr Leu Asp Pro Glu Leu Phe Val Glu Cys Thr
        1235                1240                1245
Glu Cys Gly Arg Lys Met His Gln Ile Cys Val Leu His His Glu Ile
    1250                1255                1260
Ile Trp Pro Ala Gly Phe Val Cys Asp Gly Cys Leu Lys Lys Ser Ala
1265                1270                1275                1280
Arg Thr Arg Lys Glu Asn Lys Phe Ser Ala Lys Arg Leu Pro Ser Thr
                1285                1290                1295
Arg Leu Gly Thr Phe Leu Glu Asn Arg Val Asn Asp Phe Leu Arg Arg
            1300                1305                1310
Gln Asn His Pro Glu Ser Gly Glu Val Thr Val Arg Val Val His Ala
        1315                1320                1325
Ser Asp Lys Thr Val Glu Val Lys Pro Gly Met Lys Ala Arg Phe Val
    1330                1335                1340
Asp Ser Gly Glu Met Ala Glu Ser Phe Pro Tyr Arg Thr Lys Ala Leu
1345                1350                1355                1360
Phe Ala Phe Glu Glu Ile Asp Gly Val Asp Leu Cys Phe Phe Gly Met
                1365                1370                1375
His Val Gln Glu Tyr Gly Ser Asp Cys Pro Pro Pro Asn Gln Arg Arg
            1380                1385                1390
Val Tyr Ile Ser Tyr Leu Asp Ser Val His Phe Phe Arg Pro Lys Cys
        1395                1400                1405
```

Leu Arg Thr Ala Val Tyr His Glu Ile Leu Ile Gly Tyr Leu Glu Tyr
1410                1415                    1420

Val Lys Lys Leu Gly Tyr Thr Thr Gly His Ile Trp Ala Cys Pro Pro
1425                1430                1435                1440

Ser Glu Gly Asp Asp Tyr Ile Phe His Cys His Pro Pro Asp Gln Lys
                1445                1450                1455

Ile Pro Lys Pro Lys Arg Leu Gln Glu Trp Tyr Lys Lys Met Leu Asp
                1460                1465                1470

Lys Ala Val Ser Glu Arg Ile Val His Asp Tyr Lys Asp Ile Phe Lys
                1475                1480                1485

Gln Ala Thr Glu Asp Arg Leu Thr Ser Ala Lys Glu Leu Pro Tyr Phe
                1490                1495                1500

Glu Gly Asp Phe Trp Pro Asn Val Leu Glu Glu Ser Ile Lys Glu Leu
1505                1510                1515                1520

Glu Gln Glu Glu Glu Glu Arg Lys Arg Glu Glu Asn Thr Ser Asn Glu
                1525                1530                1535

Ser Thr Asp Val Thr Lys Gly Asp Ser Lys Asn Ala Lys Lys Lys Asn
                1540                1545                1550

Asn Lys Lys Thr Ser Lys Asn Lys Ser Ser Leu Ser Arg Gly Asn Lys
                1555                1560                1565

Lys Lys Pro Gly Met Pro Asn Val Ser Asn Asp Leu Ser Gln Lys Leu
                1570                1575                1580

Tyr Ala Thr Met Glu Lys His Lys Glu Val Phe Phe Val Ile Arg Leu
1585                1590                1595                1600

Ile Ala Gly Pro Ala Ala Asn Ser Leu Pro Pro Ile Val Asp Pro Asp
                1605                1610                1615

Pro Leu Ile Pro Cys Asp Leu Met Asp Gly Arg Asp Ala Phe Leu Thr
                1620                1625                1630

Leu Ala Arg Asp Lys His Leu Glu Phe Ser Ser Leu Arg Arg Ala Gln
                1635                1640                1645

Trp Ser Thr Met Cys Met Leu Val Glu Leu His Thr Gln Ser Gln Asp
                1650                1655                1660

Arg Phe Val Tyr Thr Cys Asn Glu Cys Lys His His Val Glu Thr Arg
1665                1670                1675                1680

Trp His Cys Thr Val Cys Glu Asp Tyr Asp Leu Cys Ile Thr Cys Tyr
                1685                1690                1695

Asn Thr Lys Asn His Asp His Lys Met Glu Lys Leu Gly Leu Gly Leu
                1700                1705                1710

Asp Asp Glu Ser Asn Asn Gln Gln Ala Ala Ala Thr Gln Ser Pro Gly
                1715                1720                1725

Asp Ser Arg Arg Leu Ser Ile Gln Arg Cys Ile Gln Ser Leu Val His
                1730                1735                1740

Ala Cys Gln Cys Arg Asn Ala Asn Cys Ser Leu Pro Ser Cys Gln Lys
1745                1750                1755                1760

Met Lys Arg Val Val Gln His Thr Lys Gly Cys Lys Arg Lys Thr Asn
                1765                1770                1775

Gly Gly Cys Pro Ile Cys Lys Gln Leu Ile Ala Leu Cys Cys Tyr His
                1780                1785                1790

Ala Lys His Cys Gln Glu Asn Lys Cys Pro Val Pro Phe Cys Leu Asn
                1795                1800                1805

Ile Lys Gln Lys Leu Arg Gln Gln Gln Leu Gln His Arg Leu Gln Gln
                1810                1815                1820

Ala Gln Met Leu Arg Arg Arg Met Ala Ser Met Gln Arg Thr Gly Val

|   | 1825 | | | 1830 | | | 1835 | | | 1840 |

Val Gly Gln Gln Gln Gly Leu Pro Ser Pro Thr Pro Ala Thr Pro Thr
                                1845                1850                1855

Thr Pro Thr Gly Gln Gln Pro Thr Thr Pro Gln Thr Pro Gln Pro Thr
                1860                1865                1870

Ser Gln Pro Gln Pro Thr Pro Pro Asn Ser Met Pro Pro Tyr Leu Pro
            1875                1880                1885

Arg Thr Gln Ala Ala Gly Pro Val Ser Gln Gly Lys Ala Ala Gly Gln
        1890                1895                1900

Val Thr Pro Pro Thr Pro Pro Gln Thr Ala Gln Pro Pro Leu Pro Gly
1905                1910                1915                1920

Pro Pro Pro Thr Ala Val Glu Met Ala Met Gln Ile Gln Arg Ala Ala
                1925                1930                1935

Glu Thr Gln Arg Gln Met Ala His Val Gln Ile Phe Gln Arg Pro Ile
                1940                1945                1950

Gln His Gln Met Pro Pro Met Thr Pro Met Ala Pro Met Gly Met Asn
            1955                1960                1965

Pro Pro Pro Met Thr Arg Gly Pro Ser Gly His Leu Glu Pro Gly Met
1970                1975                1980

Gly Pro Thr Gly Met Gln Gln Gln Pro Pro Trp Ser Gln Gly Gly Leu
1985                1990                1995                2000

Pro Gln Pro Gln Gln Leu Gln Ser Gly Met Pro Arg Pro Ala Met Met
                2005                2010                2015

Ser Val Ala Gln His Gly Gln Pro Leu Asn Met Ala Pro Gln Pro Gly
            2020                2025                2030

Leu Gly Gln Val Gly Ile Ser Pro Leu Lys Pro Gly Thr Val Ser Gln
        2035                2040                2045

Gln Ala Leu Gln Asn Leu Leu Arg Thr Leu Arg Ser Pro Ser Ser Pro
    2050                2055                2060

Leu Gln Gln Gln Gln Val Leu Ser Ile Leu His Ala Asn Pro Gln Leu
2065                2070                2075                2080

Leu Ala Ala Phe Ile Lys Gln Arg Ala Ala Lys Tyr Ala Asn Ser Asn
                2085                2090                2095

Pro Gln Pro Ile Pro Gly Gln Pro Gly Met Pro Gln Gly Gln Pro Gly
            2100                2105                2110

Leu Gln Pro Pro Thr Met Pro Gly Gln Gln Gly Val His Ser Asn Pro
        2115                2120                2125

Ala Met Gln Asn Met Asn Pro Met Gln Ala Gly Val Gln Arg Ala Gly
    2130                2135                2140

Leu Pro Gln Gln Gln Pro Gln Gln Leu Gln Pro Pro Met Gly Gly
2145                2150                2155                2160

Met Ser Pro Gln Ala Gln Gln Met Asn Met Asn His Asn Thr Met Pro
                2165                2170                2175

Ser Gln Phe Arg Asp Ile Leu Arg Arg Gln Gln Met Met Gln Gln Gln
            2180                2185                2190

Gln Gln Gln Gly Ala Gly Pro Gly Ile Gly Pro Gly Met Ala Asn His
        2195                2200                2205

Asn Gln Phe Gln Gln Pro Gln Gly Val Gly Tyr Pro Pro Gln Pro Gln
    2210                2215                2220

Gln Arg Met Gln His His Met Gln Gln Met Gln Gln Gly Asn Met Gly
2225                2230                2235                2240

Gln Ile Gly Gln Leu Pro Gln Ala Leu Gly Ala Glu Ala Gly Ala Ser
                2245                2250                2255

```
Leu Gln Ala Tyr Gln Gln Arg Leu Leu Gln Gln Gln Met Gly Ser Pro
            2260                2265                2270

Val Gln Pro Asn Pro Met Ser Pro Gln Gln His Met Leu Pro Asn Gln
        2275                2280                2285

Ala Gln Ser Pro His Leu Gln Gly Gln Gln Ile Pro Asn Ser Leu Ser
    2290                2295                2300

Asn Gln Val Arg Ser Pro Gln Pro Val Pro Ser Pro Arg Pro Gln Ser
2305                2310                2315                2320

Gln Pro Pro His Ser Ser Pro Ser Pro Arg Met Gln Pro Gln Pro Ser
                2325                2330                2335

Pro His His Val Ser Pro Gln Thr Ser Ser Pro His Pro Gly Leu Val
            2340                2345                2350

Ala Ala Gln Ala Asn Pro Met Glu Gln Gly His Phe Ala Ser Pro Asp
        2355                2360                2365

Gln Asn Ser Met Leu Ser Gln Leu Ala Ser Asn Pro Gly Met Ala Asn
    2370                2375                2380

Leu His Gly Ala Ser Ala Thr Asp Leu Gly Leu Ser Thr Asp Asn Ser
2385                2390                2395                2400

Asp Leu Asn Ser Asn Leu Ser Gln Ser Thr Leu Asp Ile His
                2405                2410
```

( 2 ) INFORMATION FOR SEQ ID NO:3:

( i ) SEQUENCE CHARACTERISTICS:
        ( A ) LENGTH: 65 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:3:

```
Pro Asn Thr Tyr Pro Phe His Thr Pro Val Asn Ala Lys Val Val Xaa
1               5                   10                  15

Xaa Lys Asp Tyr Tyr Lys Ile Ile Thr Arg Pro Met Asp Leu Gln Thr
            20                  25                  30

Leu Arg Glu Asn Val Arg Lys Arg Ile Tyr Pro Ser Arg Glu Glu Phe
        35                  40                  45

Arg Glu His Leu Glu Leu Ile Val Lys Asn Ser Ala Thr Tyr Asn Gly
    50                  55                  60

Pro
65
```

( 2 ) INFORMATION FOR SEQ ID NO:4:

( i ) SEQUENCE CHARACTERISTICS:
        ( A ) LENGTH: 65 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:4:

| Pro | Asp | Ser | Trp | Pro | Phe | His | His | Pro | Val | Asn | Lys | Lys | Phe | Val | Xaa |
| 1 | | | | 5 | | | | | 10 | | | | | 15 | |

| Xaa | Pro | Asp | Tyr | Tyr | Lys | Val | Ile | Val | Asn | Pro | Met | Asp | Leu | Glu | Thr |
| | | | 20 | | | | | 25 | | | | | 30 | | |

| Ile | Arg | Lys | Asn | Ile | Ser | Lys | His | Lys | Tyr | Gln | Ser | Arg | Glu | Ser | Phe |
| | | 35 | | | | | 40 | | | | | 45 | | | |

| Leu | Asp | Asp | Val | Asn | Leu | Ile | Leu | Ala | Asn | Ser | Val | Lys | Tyr | Asn | Gly |
| | 50 | | | | | 55 | | | | | 60 | | | | |

Pro

65

( 2 ) INFORMATION FOR SEQ ID NO:5:

( i ) SEQUENCE CHARACTERISTICS:
        ( A ) LENGTH: 65 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:5:

| Gln | Phe | Ala | Trp | Pro | Phe | Arg | Gln | Pro | Val | Asp | Ala | Val | Lys | Leu | Gly |
| 1 | | | | 5 | | | | | 10 | | | | | 15 | |

| Leu | Pro | Asp | Tyr | His | Lys | Ile | Ile | Lys | Gln | Pro | Met | Asp | Met | Gly | Thr |
| | | | 20 | | | | | 25 | | | | | 30 | | |

| Ile | Lys | Arg | Arg | Leu | Glu | Asn | Asn | Tyr | Tyr | Trp | Ala | Ala | Ser | Glu | Cys |
| | | 35 | | | | | 40 | | | | | 45 | | | |

| Met | Gln | Asp | Phe | Asn | Thr | Met | Phe | Thr | Asn | Cys | Tyr | Ile | Tyr | Asn | Lys |
| | 50 | | | | | 55 | | | | | 60 | | | | |

Pro

65

( 2 ) INFORMATION FOR SEQ ID NO:6:

( i ) SEQUENCE CHARACTERISTICS:
        ( A ) LENGTH: 65 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:6:

| Ala | Tyr | Ala | Trp | Pro | Phe | Tyr | Lys | Pro | Val | Asp | Ala | Ser | Ala | Leu | Gly |
| 1 | | | | 5 | | | | | 10 | | | | | 15 | |

| Leu | His | Asp | Tyr | His | Asp | Ile | Ile | Lys | His | Pro | Met | Asp | Leu | Ser | Thr |
| | | | 20 | | | | | 25 | | | | | 30 | | |

| Val | Lys | Arg | Lys | Met | Glu | Asn | Arg | Asp | Tyr | Arg | Asp | Ala | Gln | Glu | Phe |
| | | 35 | | | | | 40 | | | | | 45 | | | |

| Ala | Ala | Asp | Val | Arg | Leu | Met | Phe | Ser | Asn | Cys | Tyr | Lys | Tyr | Asn | Pro |

( 2 ) INFORMATION FOR SEQ ID NO:7:

( i ) SEQUENCE CHARACTERISTICS:
        ( A ) LENGTH: 65 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:7:

```
Gln  Leu  Ser  Glu  Val  Phe  Ile  Gln  Leu  Pro  Ser  Arg  Lys  Glu  Leu  Xaa
 1                   5                        10                       15

Xaa  Pro  Glu  Tyr  Tyr  Glu  Leu  Ile  Arg  Lys  Pro  Val  Asp  Phe  Lys  Lys
               20                        25                       30

Ile  Lys  Glu  Arg  Ile  Arg  Asn  His  Lys  Tyr  Arg  Ser  Leu  Gly  Asp  Leu
          35                        40                       45

Glu  Lys  Asp  Val  Met  Leu  Leu  Cys  His  Asn  Ala  Gln  Thr  Phe  Asn  Leu
     50                        55                       60

Glu
65
```

( 2 ) INFORMATION FOR SEQ ID NO:8:

( i ) SEQUENCE CHARACTERISTICS:
        ( A ) LENGTH: 65 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:8:

```
Asp  Thr  Gly  Asn  Ile  Phe  Ser  Glu  Pro  Val  Pro  Leu  Ser  Glu  Val  Xaa
 1                   5                        10                       15

Xaa  Pro  Asp  Tyr  Leu  Asp  His  Ile  Lys  Lys  Pro  Met  Asp  Phe  Phe  Thr
               20                        25                       30

Met  Lys  Gln  Asn  Leu  Glu  Ala  Tyr  Arg  Tyr  Leu  Asn  Phe  Asp  Asp  Phe
          35                        40                       45

Glu  Glu  Asp  Phe  Asn  Leu  Ile  Val  Ser  Asn  Cys  Leu  Lys  Tyr  Asn  Ala
     50                        55                       60

Lys
65
```

( 2 ) INFORMATION FOR SEQ ID NO:9:

( i ) SEQUENCE CHARACTERISTICS:
        ( A ) LENGTH: 55 base pairs
        ( B ) TYPE: nucleic acid ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

CTAGCCCCGG GATGGCCTAC CCATACGACG TGCCTGACTA CGCCTCCCTC GGATA    55

( 2 ) INFORMATION FOR SEQ ID NO:10:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:10:

CCTGGATCCA CCATGGCATA CCCATACGAC GTGCCTGACT ACGCCTCCGC CGAGAATGTG    60

GTG    63

( 2 ) INFORMATION FOR SEQ ID NO:11:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

GTAGGACCCT GATTTGGTC    19

( 2 ) INFORMATION FOR SEQ ID NO:12:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:12:

GGCCGCAAGC TTCACCATGG CATACCCATA CGACGTGCCT GACTACGCCT CCGGAA    56

( 2 ) INFORMATION FOR SEQ ID NO:13:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:13:

CGCGTGATCA GCCACCATGG CCCCACCT 2 8

NUCLEIC ACID ENCODING TRANSCRIPTION FACTOR P300 AND USES OF P300

The invention relates to transcription factors in general and in particular to transcription factors that cooperate with adenovirus E1A protein to establish the transformed state.

The invention was made in the course of work supported in part by U.S. Government funds, and therefore the Government has certain rights in the invention.

BACKGROUND OF THE INVENTION

The protein p300, named for its 300 kd molecular weight, was first identified by Yee et al., 1985, Virology 147:142–153. p300, p107, and p130 are three of possibly numerous other human cellular proteins that associate with adenovirus E1A protein in immunoprecipitation experiments (Harlow et al., 1986, Molecular and Cellular Biol. 6:1597). The association of p300 with E1A appears to be necessary although insufficient for establishment of the transformed state by adenovirus (i.e., the ability of adenovirus to stimulate a normal, quiescent cell into a malignant one). Since its identification, the interaction of p300 with E1A has been widely studied; its molecular cloning, however, has been elusive due to its exceedingly large size.

Because of its involvement in adenovirus transformation, p300 is considered, like the RBp protein associated with the retinoblastoma susceptibility gene (which also binds the E1A protein), to be a negative regulator of cell growth that is at least partially inactivated by the E1A protein.

Besides stimulating the S-phase entry of quiescent cells, the region of E1A interacting with p300 is also responsible for repressing a number of transcriptional enhancers and promoters. The first identified targets for E1A repression were the viral enhancers of the SV40 and polyoma virus and the enhancer controlling the transcription of the E1A gene itself. In addition to this group of viral enhancers, a second class of enhancers and promoters driving transcription of tissue specific cellular genes associated with the terminal differentiation state of a cell were found to be repressed by E1A.

p300 and p300-associated proteins have been reported to be components of TATA-binding protein complexes (Abraham et al., 1993, Oncogene 8:1639). It has been observed that E1A mutants defective for p300 binding are also defective for an E1A-induced function that represses enhancer-mediated tissue-specific gene expression. This observation underlines the suggestion in the art that p300 may play a role in enhancer-stimulated expression of tissue-specific genes. A p300 consensus DNA-binding sequence has been proposed which shows some similarity to certain E1A-targeted enhancer elements (Abraham et al., 1993, supra).

SUMMARY OF THE INVENTION

The invention is based on the discovery of the nucleic acid sequence encoding p300, and characterization of the encoded protein.

The invention thus features an isolated nucleic acid hybridizable with the complement of the coding strand nucleic acid sequence presented in SEQ ID NO:1, and encoding a protein that is necessary for adenovirus transformation of a mammalian cell.

The nucleotide sequence of the full length human p300 cDNA clone and its predicted amino acid sequence are provided in FIG. 4 and in SEQ ID NOS: 1 and 2, respectively.

The invention also features vectors comprising the isolated nucleic acid encoding p300, and a host cell transfected with a vector. Preferred vectors include baculovirus-based vectors; preferred host cells include mammalian cells.

The invention also features nucleotide sequences encoding fragments and deletions of p300, and the encoded polypeptides. These deletions of the p300 nucleotide sequence include deletion of nucleotides encoding amino acids constituting the portion of p300 that interacts with E1A (i.e., the E1A binding region of p300). Thus, the invention encompasses a p300 deletion mutant that lacks the E1A binding region.

As used herein, the "E1A binding region" of p300 is the region of the amino acid sequence presented in SEQ ID NO:2 encompassing amino acids residues 1572 and 1818.

In another embodiment, methods are provided for overcoming the repressive effect of an E1A oncoprotein on a promoter that is operationally linked to a transcriptional enhancer. These methods involve incubating an undifferentiated cell having repressed enhancer activity with a mutated p300 protein, or a cell engineered to express such a protein, under conditions sufficient to allow for derepression of the enhancer. The mutated p300 protein will possess an altered E1A binding domain, but will retain E1A binding activity.

The invention also encompasses nucleic acid probes comprising 15 nucleotides, preferably 20–30, more preferably 50–80 nucleotides, and most preferably 100–300 nucleotides that hybridize with a region of the nucleic acid of claim 1.

As used herein, the term "hybridization" refers to conventional DNA/DNA hybridization conditions. For example, for a probe of 15–30 nucleotides, hybridization conditions include 10× SSC, 5× Denhardts, 0.1% SDS, at 35–50 degrees for 15 hours; for a probe of 100–300 nucleotides, "stringent" hybridization conditions are preferred and refer to hybridization in 6× SSC, 5× Denhardts, 0.1% SDS at 65 degrees for 15 hours.

The invention also provides methods for detecting non-wild-type p300 genes using hybridization probes based upon the full length cDNA sequence of p300 or a fragment thereof, in which detection of mutations in the p300 gene are indicative of tumorigenesis.

The isolated nucleotide sequences can also be used to make recombinant forms or fragments of the p300 protein, which in turn can be used to make monoclonal antibodies to a host of epitopes on the p300 molecule, particularly antibodies specific for the carboxy terminus of the molecule. These antibodies are useful for detecting mutant forms of p300, or for detecting wild-type p300 without disrupting interaction of native p300 with cellular and viral proteins.

Thus, the invention also features a monoclonal antibody that binds to an epitope of the carboxy-terminal region of p300 between amino acid residues 1572 and 2371, inclusive, as defined in SEQ ID NO:2 (FIG. 4).

Preferably, the epitope is a region of p300 as presented in Table 1.

The invention also includes methods for diagnosing a cancerous or precancerous tissue in a subject, comprising detecting the presence of a non-wild-type p300-encoding gene in a tissue sample from the subject.

The invention also encompasses a kit for diagnosis of a cancerous or precancerous condition in a subject, including an isolated nucleic acid defining full-length p300 or a portion thereof useful as a probe as defined above.

The invention also includes methods for diagnosing a cancerous or precancerous tissue in a subject, comprising detecting the presence of a non-wild-type p300 protein in a tissue sample from the subject.

The invention also encompasses a cancerous or precancerous condition in a subject, comprising the monoclonal antibody specific for p300.

The invention also includes methods of screening for a compound that inhibits or enhances p300-dependent transcription, comprising (a) providing an expression assay comprising p300 protein and a p300-dependent genetic regulatory element operationally associated with a reporter gene, wherein in the presence of p300 protein the reporter gene is expressed at a base level; and (b) incubating in the expression assay a candidate compound for a time and in a concentration sufficient to inhibit or enhance reporter gene expression to a level that is below or above the base level, respectively; wherein the reporter gene expression below the base level is indicative of an inhibitory effect of the compound, and the reporter gene expression above the base level is indicative of an enhancing effect of the compound.

Preferably, the regulatory element comprises the c-jun promoter; the expression assay comprises ras-transformed mammalian cells cotransfected with an expressible p300 gene and the c-jun promoter operationally associated with the reporter gene.

Preferably, one candidate compound is a mutant p300 protein containing an amino acid alteration resulting in constitutive repression of the c-jun promoter, wherein upon incubating the cells with mutant p300 protein, the level of expression of the reporter cells is below the basal level.

The invention also includes methods of screening for a mutant p300 protein that retains E1A binding activity but inhibits E1A repression of an enhancer, comprising: (a) providing an expression system comprising a transcriptional enhancer susceptible to repression by E1A oncoprotein and operationally associated with a promoter and reporter gene, and E1A oncoprotein, wherein reporter gene is expressed at a base level; and (b) incubating a candidate mutant p300 protein in the expression system for a time and under conditions sufficient to allow for expression of the reporter gene above the base level.

Preferably, the candidate mutant p300 protein is provided to the expression system via DNA encoding the mutant p300 protein.

Further features will become more fully apparent in the following description of the embodiments of this invention and from the appended claims.

BRIEF DESCRIPTION OF THE DRAWINGS

In the drawings:

FIGS. 4A–4O show the nucleotide sequence of the p300 SEQ ID NO:1 cDNA and its predicted amino acid sequence SEQ ID NO:2. The three cysteine/hystidine-rich regions are marked "C/H rich" on the left. In the first region, the residues of the two putative zinc finger motifs involved in coordinating zinc are circled and the other cys and his residues are underlined. In the second and third C/H rich region, the cys and his residues are highlighted with squares. The bromodomain in the middle of p300 is boxed, and the nuclear location signal at the N-terminus (see FIG. 8) is marked with a line above and below it. The GenBank accession number for the p300 sequence is U01877.

FIG. 4P presents sequence alignments of human bromodomain proteins. The bromodomains of the five human bromodomain-containing proteins were aligned. CCG1 (TAF 250) and RING3 each contain two bromodomains given in SEQ ID NOS:3 and 4 and SEQ ID NOS:5 and 6 respectively. hBRM see SEW ID NO:7 is a human homolog of the Drosophila brahma protein. The consensus sequence is given at the top: only amino acid residues that are conserved in all seven bromodomains, or that are present in at least six of the seven human bromodomains are listed. In addition, residues that are conserved in all seven domains are marked in the alignment with a box. The three tryptophan residues in the p300 bromodomain that are spaced as a heptad repeat are underlined. The position of the region predicted to form two alpha helices followed by reverse turns is indicated below. Database accession numbers for sequences: CCG1-D90359; RING3-X62083; hBRM-X72889; PEREGRIN-M91585 see SEQ. ID. NO:8.

FIG. 7, lane 7).

DETAILED DESCRIPTION OF THE INVENTION

Figure 1A:
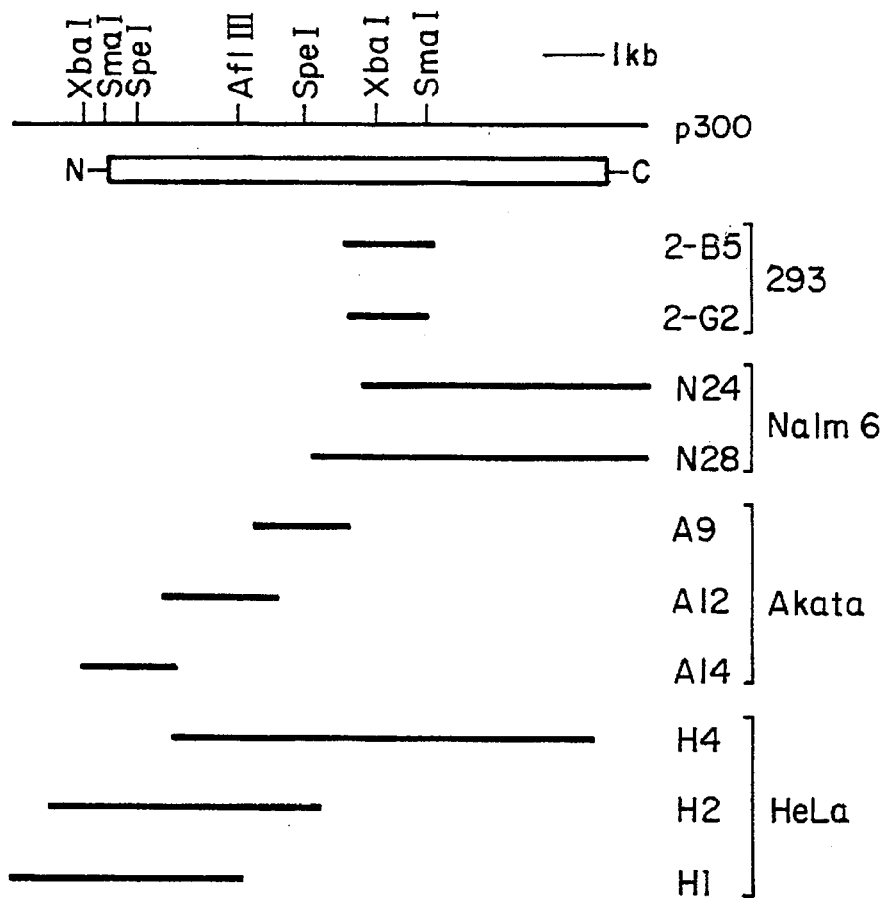
FIG. 1A is a schematic representation of isolated p300 cDNA fragments. The assembled p300 cDNA with key restriction sites and the position of the open reading frame is shown at the top of the figure. Below, the most relevant of the obtained cDNA fragments are depicted in the order in which they were isolated (from top to bottom). The library from which the fragments were derived is indicated on the right. The Akata cDNA library was screened three times, the other three libraries were each probed once. The HeLa library is described by Xiao et al., 1991, Cell 65: 551–568.

The invention is based upon isolation and determination of the nucleotide sequence of the gene encoding the human protein p300, and to functional analyses of the recombinant p300 protein. These analyses reveal that p300 is involved in gene regulation at the transcriptional level. The invention also is based on the detection of mutant p300 genes and proteins as indicators of the neoplastic state.

The growth controlling functions of the adenovirus E1A oncoprotein depend on its ability to interact with a set of cellular proteins. Among these are the retinoblastoma protein, p107, p130 and p300. p300 was first documented in the literature in 1985. Numerous attempts have been made to clone the gene encoding p300 according to conventional cloning methods, yet none of these attempts was successful. For example, a conventional cloning strategy based on the use of degenerate oligonucleotides based on amino acid microsequence information from tryptic peptide digests of the p300 protein has not been feasible largely due to the enormous size of the protein. That is, trypsin digestion of p300 generates numerous peptides having similar HPLC elution profiles. Another conventional cloning strategy involves expression screening of cells containing cDNA expressing p300 using polyclonal antiserum. This approach requires confirmation of the identity of the protein product encoded by the cloned cDNAs, e.g., via peptide mapping of in vitro translated protein. However, again due to the exceedingly large size of the p300 protein, it is not possible to obtain enough in vitro translated, full-length p300 protein to generate peptide maps. Moreover, in vitro translated p300 appears to lack certain post-translational modifications that may affect generation of peptides.

In view of the repeated failures of prior attempts to clone the p300 gene, we developed a novel cloning strategy which ultimately proved to be successful for obtaining the gene. Our strategy was based on obtaining a true peptide map of correctly modified p300. This was achieved by expressing HA-tagged p300 in mammalian cells, thereby allowing endogenous p300 to be distinguishable from the tagged protein. We then used the HA-tagged protein for peptide mapping experiments. We have thus provided cDNA encoding full-length human p300 a SEQ ID NO:1 nd mapped the chromosomal location of the gene to chromosome 22q13.

The predicted amino acid sequence of p300 SEQ ID NO:2 reveals three cysteine- and histidine-rich regions of which the most C-terminal one interacts specifically with E1A. In its center, p300 contains a bromodomain, a hallmark of certain transcriptional coactivators. We have examined the ability of p300 to overcome the repressive effect of E1A on the SV40 enhancer. We show that p300 molecules lacking an intact E1A binding site can bypass E1A repression and restore to a significant extent the activity of the SV40 enhancer, even in the presence of high levels of E1A protein. These results imply that p300 may function as a transcriptional adaptor protein for certain complex transcriptional regulatory elements.

The invention is based on the molecular cloning, structural analysis, and characterization of p300. Our results show that p300 has the structural and functional properties of a transcriptional adaptor molecule that appears to be required for the activity of certain enhancers.

EXAMPLE I

Molecular Cloning and Sequencing of p300 Gene.

Microgram quantities of p300 were isolated from 293 cells by applying the anti-E1A immunopurification procedure previously used to purify p107, another E1A associated protein (Ewen et al., 1991, Cell 66:1155–1164). All cells were grown at 37° C. in a humidified, 10% $CO_2$-containing atmosphere in Dulbecco's modified essential medium (DMEM) containing 10% fetal calf serum (Hyclone). E1A associated proteins were purified by passing 293 cell extract over columns containing immobilized, anti-E1A monoclonal antibody M73, as described previously. Three different mice were successfully immunized with gel band purified p300, and the resulting polyclonal antisera specifically recognized p300, as determined by peptide mapping experiments. In order to be able to screen a cDNA expression library, the antisera (at a 1:1000 dilution) had to be extensively preadsorbed against nitrocellulose filters containing non-recombinant phage plaques to remove antibodies reacting nonspecifically with E. coli proteins. One of the three antisera was used to screen 1.2 million plaques from a 293 cell cDNA library (Ewen et al., 1991, supra) according to standard procedures (Ausubel et al., 1987, Current Protocols in Molecular Biology, John Wiley & Sons, New York). Two positive phage clones were obtained. Plaques of both clones also reacted strongly with the two other antisera, while a non-recombinant control phage gave no signal. The two phages contained overlapping inserts (2-B5 and 2-G2 in FIG. 1A). Sequential screening of four different cDNA libraries resulted in the recovery of cDNAs which together spanned about 9 kb (see FIG. 1A). Insert 2-B5 was then used to screen a Nalm 6 lambdaZap cDNA library The 5' end of the longest isolated clone (N28) was employed to screen an Akata cell lambda-gtil cDNA library which resulted in the isolation of clone A9 (among others). The Akata library was rescreened with this clone, and the insert containing the longest extension of the available p300 cDNA (insert A12) was labelled to reprobe the Akata library and to screen a HeLa lambdaZap cDNA library (Xiao et al., 1991, Cell 65:551–568). This resulted in the isolation of cDNA inserts covering the 5' end of p300. Hybridization and washing conditions of the filters used for screening libraries and probing Northern blots were as described (Church and Gilbert, 1984, Proc Natl. Acad. Sci. U.S.A. 81:1991–1995).

Figure 1B:
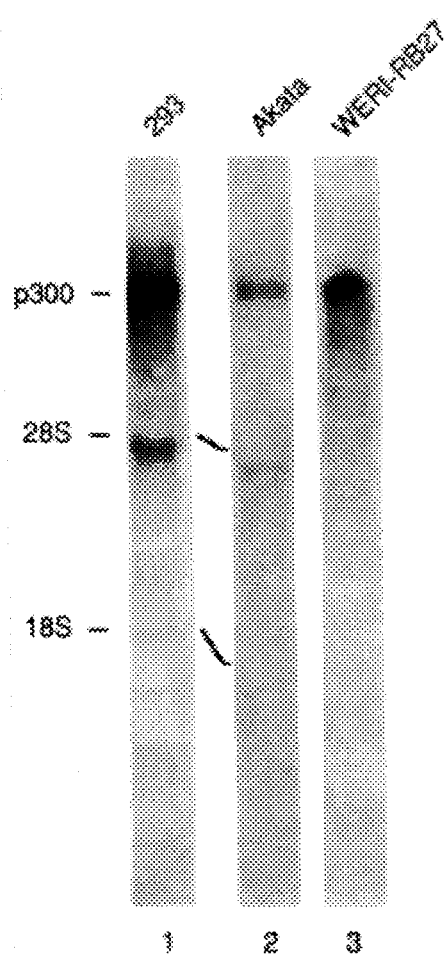
FIG. 1B is a Northern blot using RNA from three different human cell lines. Cytoplasmic RNA from 293 cells (embryonic kidney cells transformed by the early region of adenovirus) was probed with the 2-B5 insert (lane 1). Cytoplasmic RNA from Akata cells (a Burkitt-lymphoma cell line) and poly(A)-selected RNA from WERI-RB27 (a retinoblastoma derived cell line) were each hybridized with the A12 cDNA fragment (lanes 2 and 3). Hybridization and washing of the blots were performed under high stringency conditions. The positions of the 18S and 28S ribosomal RNAs are indicated on the left.

We have performed Northern analyses under high stringency conditions with all of the cDNA fragments depicted in FIG. 1A and found that they all hybridize to a transcript of ~9kb in size. In keeping with the ubiquitous expression of the p300 protein (Yaciuk and Moran, 1991, Mol. Cell. Biol. 11:5389–5397), we detected the 9 kb mRNA in all eight cell lines examined. RNA derived from the following cell lines was examined on Northern blots: Akata, 293, WERI-RB27, HeLa, SV80, U-2 OS, Nalm-6 and Saos2. FIG. 1B shows an example of such a Northern blot with cytoplasmic RNA from 293 and Akata cells (lanes 1 and 2) and poly(A) selected WERI-RB27 RNA (lane 3). We frequently observed a signal just below the 28S rRNA. This signal was absent when polyadenylated RNA from WERI-RB27 cells was analyzed (lane 3), but was present when total RNA from the same cell line was probed (data not shown). Thus, it likely represents a nonspecific hybridization signal caused by 28S rRNA.

Figure 2:
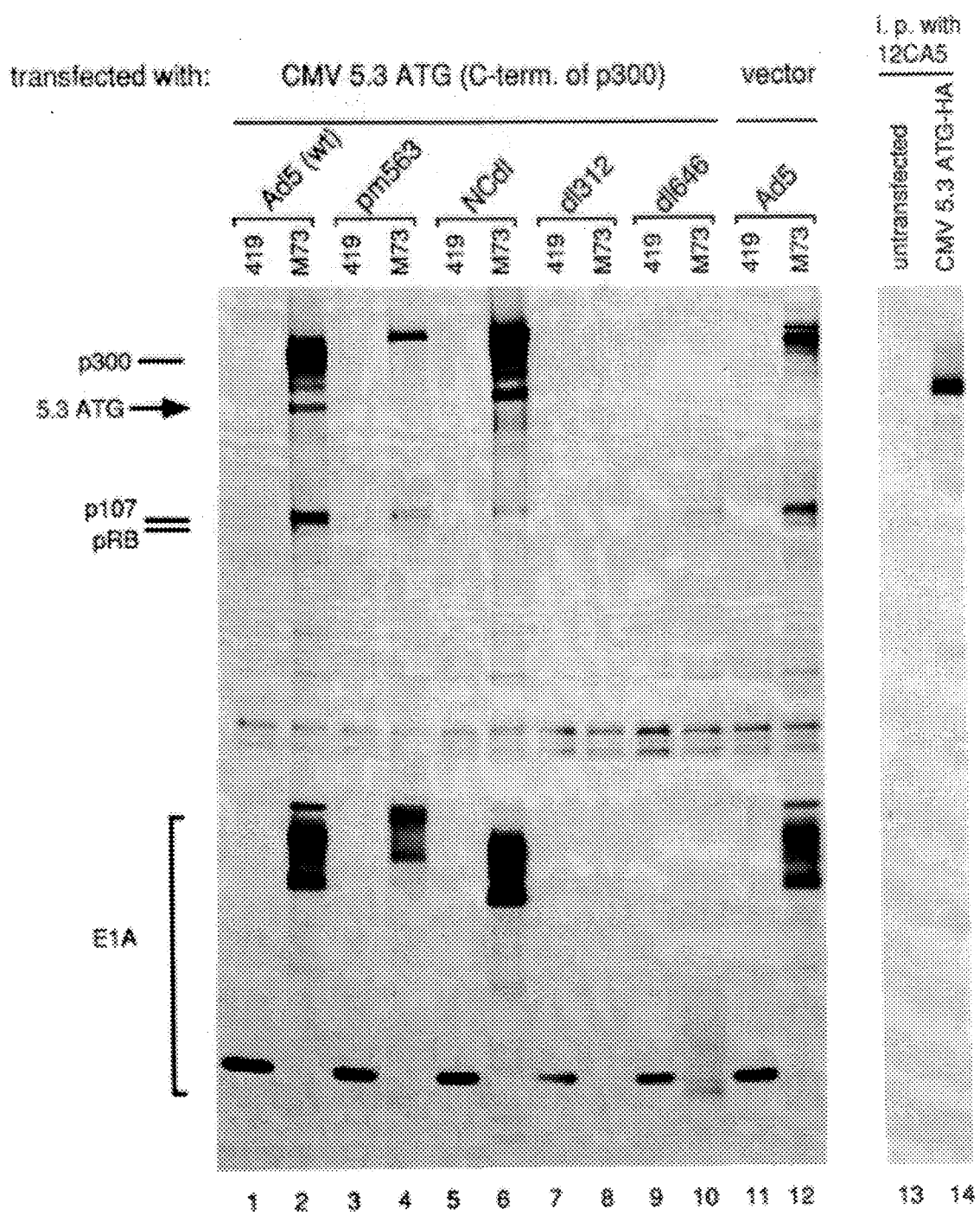
FIG. 2 shows results of an analysis of the in vivo E1A binding characteristics of a C-terminal 200 kD fragment of p300. U-2 OS cells were transiently transfected with the CMV 5.3 ATG plasmid directing the expression of a 200 kD carboxy terminal fragment of p300. One day after transfection, cells analyzed in lanes 1–10 were trypsinized, pooled and reseeded on 5×10 cm dishes, in order to equalize for transfection efficiencies. Cells were then infected with the adenovirus species indicated at the top. 10 hours later, they were labelled with $^{35}$S-methionine. A lysate of each dish was split in half and immunoprecipitated with Pab 419 (control) or the anti-E1A monoclonal antibody, M73. Ad5 encodes wild-type E1A proteins; pm563 encodes E1A proteins with a point mutation in amino acid 2; NCd1 encodes E1A proteins lacking amino acids 86–120 (these residues lie between CR1 and CR2). The dl312 virus is deleted for the E1A gene, and dl646 encodes E1A proteins missing amino acids 30–85. Lanes 11 and 12 show the immunoprecipitation pattern of cells transfected with the expression vector lacking an insert, followed by infection with wt Ad5. In lanes 13 and 14, lysates of untransfected U-2 OS cells and of U-2 OS cells transfected with a hemagglutinin-epitope tagged version of the 5.3 ATG plasmid, respectively, were incubated with the anti-HA antibody, 12CA5. The positions of E1A and its associated proteins are noted on the left.

Preliminary experiments indicated that the proteins synthesized by the N24 and N28 cDNA inserts bound E1A. To investigate whether this region of the presumed p300 cDNA could interact with E1A in vivo, in a manner similar to endogenous p300, we transfected U-2 OS cells with a plasmid designated CMV 5.3 ATG. This plasmid contains a consensus ATG translation initiation codon followed by the C-terminal 5.3 kb of the p300 cDNA. It encodes a 200 kD protein (visible in FIG. 2, lane 14 as a hemagglutinin-epitope tagged version) which can be well separated from endogenous p300 in SDS-polyacrylamide gels. The U-2 OS cell line is derived from an osteosarcoma, expresses a wild-type retinoblastoma protein (Huang et al., 1988, Science 242:1563–1566), and was chosen because it can be well transfected. One day after transfection, the cells were infected with a series of adenoviruses harbouring wild-type or mutant E1A genes. 10 hours later, the cells were labelled with $^{35}$S-methionine, lysed and the extract of each dish was immunoprecipitated with the anti-E1A monoclonal antibody M73 (Harlow et al., 1985, J. Virol. 55:533–546), or with the monoclonal antibody Pab 419, which served as a control. FIG. 2 illustrates the result that whenever the endogenous p300 was coprecipitated, the 200 kD protein encoded by the 5.3 ATG construct was also present in the immunoprecipitate. This is the case for wild-type E1A (lane 2) and for the E1A mutation NCdl, carrying a deletion between CR1 and CR2 (lane 6). By contrast, E1A proteins with either a point mutation in amino acid 2 (pm563, lane 4) or bearing a deletion of CR 1 (d1646, lane 10) failed to associate with either endogenous p300 and the exogenous 200 kD protein. The high molecular weight protein in lane 4 is the E1A associated p400 protein described earlier (Howe and Bayley, 1992, A. Virol. 186:15–24). No E1A associated proteins were detected when U-2 OS cells were infected with the dl312 virus which does not synthesize E1A owing to a large deletion in the early region of this virus (FIG. 2, lane 8). Similarly, no protein in the size range of 200 kD was coprecipitated from lysates of cells transfected with the expression vector lacking an insert (lane 12). This experiment demonstrates that the transfected cDNA encodes a protein exhibiting the same genetics of E1A binding as the endogenous p300 protein.

The sequence of the assembled p300 cDNA and the predicted open reading frame are shown in FIG. 4A. The p300 cDNA sequence was established by sequencing overlapping cDNA inserts on both strands. One part of the p300 cDNA fragments was sequenced by the dideoxy chain termination method using the Sequenase kit 2.0 (U.S. Biochemical Corporation). The other part was sequenced on an Applied Biosystems automated sequencer using a primer walking approach.

The p300 mRNA contains a remarkably long 5' untranslated region (1.2 kb). The 5' terminal 1 kb are rich in CpG dinucleotides, indicative of the 5' ends of many constitutively transcribed housekeeping genes (Bird, 1986, Nature 321:209–213). The p300 mRNA shares this feature with the pRB and p107 messengers. The translation initiation codon of p300 is preceded by an in frame stop codon located 45 nucleotides further upstream. The sequence context of the initiator AUG matches well with the consensus sequence flanking translational start codons (Kozak, 1991, J. Cell. Biol. 115:887–903). The open reading frame of the cDNA encompasses 2414 amino acids and predicts a protein with a molecular weight of 264.236 kd.

Data base searches with the p300 protein sequence revealed that p300 has in its central region a bromodomain (see FIG. 4B). This 65 amino acid domain of unknown function is conserved from yeast to man (Haynes et al., 1992, Nucl. Acids Res. 20:2603; Tamkun et al., 1992, Cell 68:561–572) and has been found in several proteins implicated as global activators of transcription. Included in this group of polypeptides are the human (Sekiguchi et al., 1991, Mol. Cell. Biol. 11:3317–3325; Hisitake et al., 1993, Nature 362:179–181; Ruppert et al., 1993, Nature 362:175–179) and Drosophila (Kokubo et al., 1993, Genes & Der. 7:1033–1046; Weinzierl et al., 1993, Nature 362:511–517) 250 kD TATA binding protein associated factors (TAF$_{II}$250/CCG1), each of which contains two bromodomains. As noted by Haynes et al. (1992, supra), the second part of the bromodomain is likely to form two short amphipathic alpha helices followed by reverse turns (see FIG. 4B). In keeping with the amphipathic character of this region, the second helix of the p300 bromodomain contains on the hydrophobic side of its surface a heptad repeat of 3 tryptophan residues (FIG. 4B).

Further analysis of the p300 amino acid sequence revealed the presence of three cysteine and histidine rich domains (FIG. 4A). The most N-terminal one of these domains can be aligned as two zinc fingers: in each of the two putative fingers, two pairs of cysteines are spaced by a 12 amino acid linker reminiscent of the structure of zinc fingers. However, the two fingers of p300 do not display a number of residues well conserved among various subgroups of zinc finger proteins and, therefore, do not completely conform to the classical zinc finger consensus sequence. Moreover, there are additional cysteines and histidines residues present between the pairs of cysteines highlighted in FIG. 4A. Conceivably, they also participate in the coordination of zinc ions. The other two cysteine/histidine rich regions of p300 are localized in the C-terminal half of the protein (FIG. 4A). In both of these regions, the arrangement of these two amino acids does not reveal any similarity to other known cys/his-rich motifs, e.g. the LIM domain (Li et al., 1991, Proc. Natl. Acad. Sci. U.S.A. 88:9210–9213) or the RING-motif (Freemont et al., 1991, Cell 64:483–484). Overall, p300 is rich in prolines, glutamines and serines which together constitute more than 30% of all amino acid residues of the protein. The abundance of prolines, distributed throughout the protein, makes it unlikely that p300 exhibits many extended alpha-helical regions.

EXAMPLE II

Expression of Full-length p300 Protein in Mammalian Cells

Figures 5A, 5B, 5C:
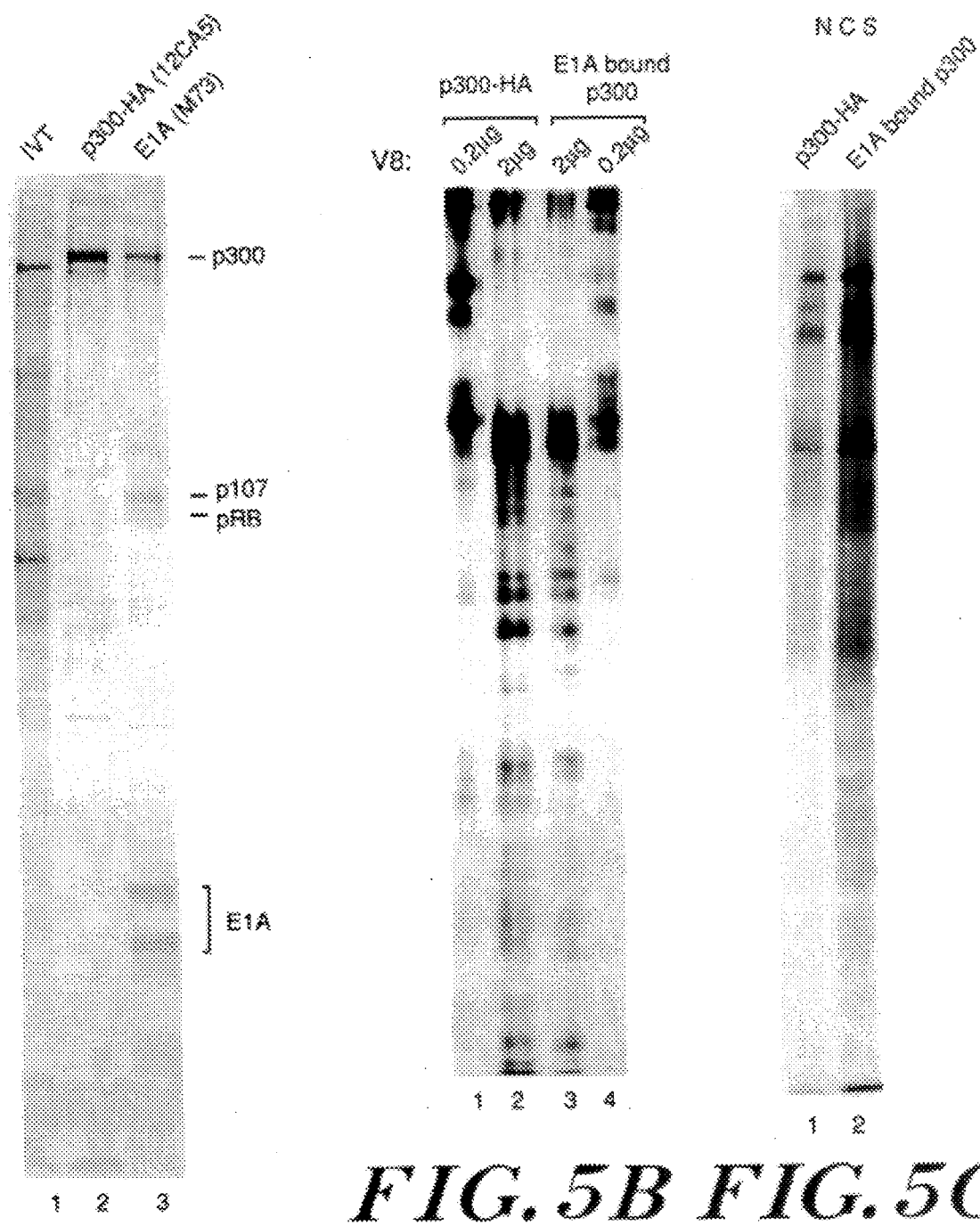
FIG. 5A is a comparison of the cloned p300 protein with the E1A bound 300 kD protein. The migration of full length, $^{35}$S-labelled p300 generated by in vitro translation (lane 1) is compared with the migration of HA (hemagglutinin)-tagged, full length p300 immunoprecipitated with the 12CA5 antibody from lysates of transfected, $^{35}$S-methionine labelled U-2 OS cells (lane 2) and with the mobility of the E1A bound 300 kD protein immunoprecipitated from 293 cells with the anti-E1A monoclonal antibody M73 (lane 3). The faint bands visible in lane 2 below p300 represent most likely background bands, since they can also be seen with lysates from untransfected cells (see e.g.
FIG. 5B presents SDS protein-gel purified, $^{35}$S labelled p300 proteins derived from U-2 OS cells transiently transfected with HA-tagged, cloned p300 (p300-HA) and from 293 cells (E1A bound p300) were partially digested with S. aureus V8 protease, employing the procedure of Cleveland et al., 1977, J. Biol. Chem. 252: 1102–1106. The amount of V8 protease used is indicated on top.
FIG. 5C is an N-chlorosuccinimide (NCS) cleavage map of p300-HA and E1A bound p300. NCS cleavage was carried out as described in Draetta, 1987, Cell 50: 319–325.

To determine whether the assembled p300 cDNA clone was functional, we produced, by transient transfection, full-length hemagglutinin-epitope (HA)-tagged p300 in U-2 OS cells. As illustrated in FIG. 5A, the exogenous, HA-tagged p300 comigrated in an SDS-polyacrylamide gel with the E1A associated 300 kD protein (compare lanes 2 and 3). In vitro translated p300 (lane 1) displayed a slightly faster mobility than in vivo synthesized p300, suggesting that it lacks certain posttranslational modifications.

We next subjected $^{35}$S labelled HA-tagged p300, derived from transfected U-2 OS cells, and authentic, E1A bound, endogenous 300 kD protein to comparative peptide mapping experiments with S. aureus V8 protease. The patterns of the two proteins obtained by partial digestion with this enzyme were generally similar (FIG. 5B). There were some minor differences between the HA-tagged, cloned p300 and the E1A bound 300 kD protein. To rule out a cloning artefact, we reassembled a full length p300 cDNA using a set of cDNA fragments completely different from that used for the construction of the first p300 cDNA (see Methods). This newly assembled p300 clone encoded a protein again showing the same small deviations seen before from the proteolytic pattern of E1A bound, endogenous p300 (data not shown). This result argues against a cloning artefact, and suggests that the small differences are due to other influences, e.g. overproduction of the protein (see below) or the presence of a hemagglutinin tag.

In order to probe the structural similarity of the cloned p300 and the E1A associated 300 kD protein by a second approach, we used the chemical agent N-chlorosuccinimide (NCS) which cleaves proteins after tryptophan residues. FIG. 5C illustrates that also this method resulted in virtually identical cleavage patterns among the cloned and endogenous proteins.

Figure 6A:
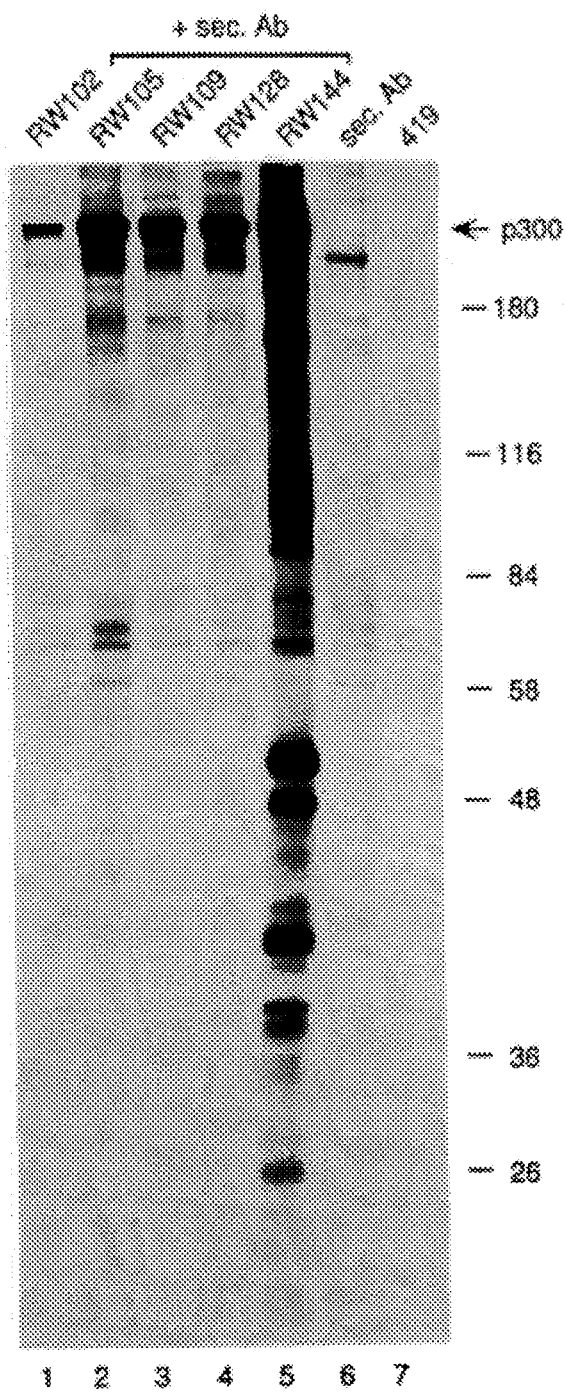
FIG. 6A presents immunoprecipitations of p300 using monoclonal antibodies directed against p300. Lysates from $^{35}$S-methionine labelled U-2 OS cells were immunoprecipitated with five different anti-p300 monoclonal antibodies (lanes 1–5) or with a rabbit anti-mouse IgG secondary antibody (lane 6), or with the monoclonal antibody Pab 419 which is directed against SV40 T antigen and which served as a control (lane 7). Four of the five anti-p300 monoclonal antibodies were of the IgG1 isotype and required the use of a secondary antibody in order to collect immunocomplexes efficiently with protein A-sepharose (lanes 2–5). The many bands seen with antibody RW144 likely represent proteins that contain cross-reactive epitopes, because some of these proteins can be detected on a Western blot probed with the same antibody.
Figure 6B:
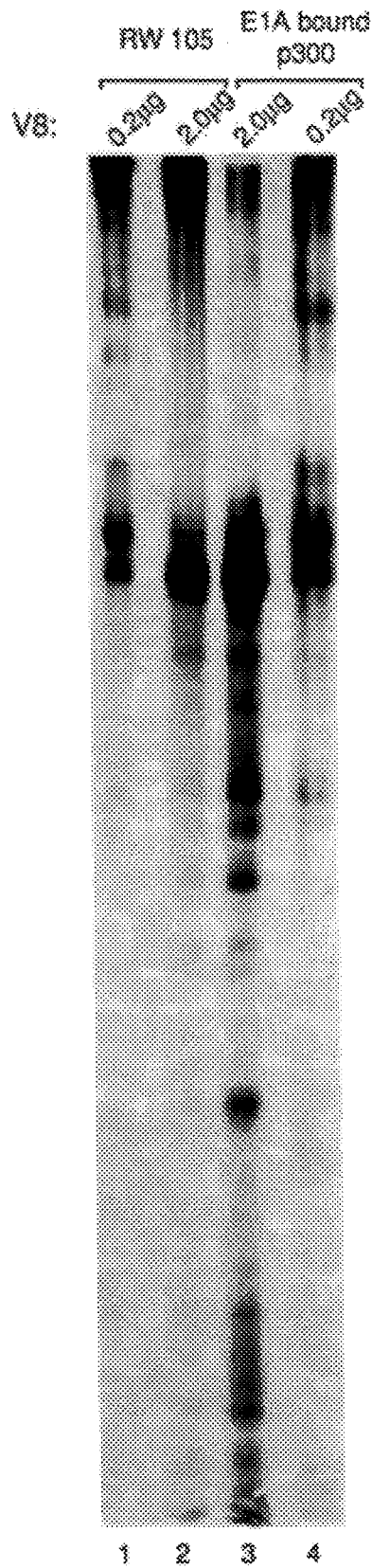
FIG. 6B is a peptide map comparing p300 from U-2 OS cells brought down with monoclonal antibody RW105 against E1A bound p300 from 293 cells. The amount of S. aureus V8 protease used is indicated on the top.

Finally, a series of five monoclonal antibodies raised against *E. coli* produced p300 protein provided another piece of evidence for the authenticity of the cloned p300 cDNAs. These antibodies recognize different epitopes in the C-terminus of p300, based on the pattern of in vitro translation products recognized by immunoprecipitation with each (data not shown) and based on epitope mapping studies summarized in Table 2, which shows the epitopes recognized on p300 by the five monoclonal anti-p300 antibodies. The major product immunoprecipitated by these monoclonal antibodies from $^{35}$S labelled U-2 OS cell lysates was a 300 kD protein (FIG. 6A) that displayed, in each case, a proteolytic peptide mapping pattern identical to that of the E1A associated 300 kD protein (FIG. 6B shows the V8 protease map for RW105). In addition, when the monoclonal antibodies directed against p300 were used with lysates prepared from the E1A transformed 293 cell line, some of the antibodies coprecipitated E1A (data not shown).

Taken together, the above presented results permit us to conclude that the isolated cDNAs encode the E1A-associated 300 kD protein.

Methods for preparation of full-length p300 cDNA and analysis of transfected cells were as follows. The human osteosarcoma cell line U-2 OS was transfected by the Hepes-CaPO$_4$ method (Ausubel et al., 1987, supra). The precipitates were left for 12 hours on the cells. Cells were then washed twice with PBS and processed 36 hours later for either immunoprecipitation or luciferase experiments. For adenovirus infections, the respective viruses were added to U-2 OS cells in 3 ml of DMEM without serum at an moi of 10 and incubated for 1 hour. Subsequently, DMEM containing 10% fetal calf serum was added, and cells were labelled with $^{35}$S-methionine 10 hours later.

Cells were labelled for 4 hours using 0.5 mCi $^{35}$S-methionine per 10 cm dish in DMEM containing 5% dialyzed fetal calf serum. Typically, a 10 cm dish was lysed for 20 min at 4° C. in 1 ml of EBC (50 mM Tris-HCl pH 8.0, 170 mM NaCl, 0.5% NP-40, 50 mM NaF) containing 10 µg/ml of protease inhibitors aprotinin, leupeptin and PMSF. The lysate was then centrifuged at 14,000×g for 10 min to pellet debris. Following preclearing for 30 min with 50 µl of a 1:1 slurry of protein A-sepharose in 4% BSA, the supernatant was incubated on a rocker for 1 hr with 100 µl of the respective monoclonal antibody. Immunocomplexes were collected by adding 25 µl of protein A-sepharose beads and further rocking for 30 min. Finally, the beads were washed five times with NETN (10 mM Tris-HCl pH 8.0, 250 mM NaCl, 5 mM EDTA, and 0.5% NP-40). For analysis of immunoprecipitated proteins, the beads were boiled in 1× SDS-sample buffer (2% SDS, 10% glycerol, 62 mM Tris pH 6.8 and 1% β-mercaptoethanol) and loaded onto SDS-polyacrylamide gels.

Two full length p300 cDNAs were assembled in pBluescript (Promega) from two different sets of partial cDNA inserts in order to minimize chances of cloning artifacts. The first p300 cDNA (pBluescript p300-1) was constructed from inserts N28, A9 and H2 (see FIG. 1A), using suitable internal restriction sites to ligate the three fragments together. The second version of full length p300 (pBluescript p300-2) was assembled using cDNA fragments N24, H4 and H1. Comparative peptide mapping experiments confirmed that both clones were identical. To distinguish between endogenous p300 and introduced, full length, p300 a hemagglutinin epitope tag was attached to either the C-terminus or the N-terminus of p300. The C-terminal HA-tag was generated by ligating the oligonucleotide 5'-CTAGCCCCGGGATGGCCTACCCATACGACGTG-CCTGACTACGCCTCCCTCGGATA-3' SEQ ID NO:9 and its complementary strand between the Nhe I site near the C-terminus of p300 and the Hind III site in the polylinker of pBluescript. This manipulation removes the last 36 amino acid residues of p300 and replaces them by 16 residues comprising the HA-tag. The N-terminal HA-tag was fused to the p300 cDNA by using the oligo 5'-CCTGGATCCACCATGGCATACCCATACGACGTGCC TGACTACGCCTCCGCCGAGAATGTGGTG-3' SEQ ID NO:10 as the upstream primer and 5'-GTAGGACCCTGATTTGGTC-3' SEQ ID NO:11 as the downstream primer in a PCR reaction. The 420 bp PCR product was digested with BamH I and Spe I and ligated to the Spe I site near the N-terminus of p300. This manipulation led to the addition of an in frame HA-tag to the second amino acid residue of p300. The mutant Δ-N-p300 was generated by ligating the oligonucleotide 5'-GGCCGCAAGCTTCACCATGGCATACCCATACGAC GTGCCTGACTACGCCTCCGGAA-3' SEQ ID NO:12 and its complementary strand to the Spe I site near the N-terminus of p300. The 5.3 ATG construct was created by ligating the oligonucleotide 5'-CGCGTGATCAGCCACCATGGCCCCACCT-3' SEQ ID NO:13 and its complementary strand to the Bgl I site at position 3808 of the p300 cDNA sequence. The sequence of the above described four constructs was checked by sequencing. In order to express the four constructs in mammalian cells, they were transferred as Not I-Hind III fragments from pBluescript to the mammalian expression vector CMVβ in which the CMV promoter/enhancer drives the expression of an inserted cDNA. In this vector, the second intron and the polyadenylation signal from the rabbit β-globin gene provide the signals for efficient RNA processing.

EXAMPLE III

Determination of the E1A binding site on p300 Protein and Binding Site Mutant p300 Proteins We next sought to map the E1A interaction site on p300. To this end, a series of in vitro translation templates with progressive 5' or 3' deletions was prepared. The templates were derived from the C-terminal half of p300 shown before (FIG. 2) to contain the binding site for E1A. They are depicted schematically in FIG. 7D.

Figure 7A:
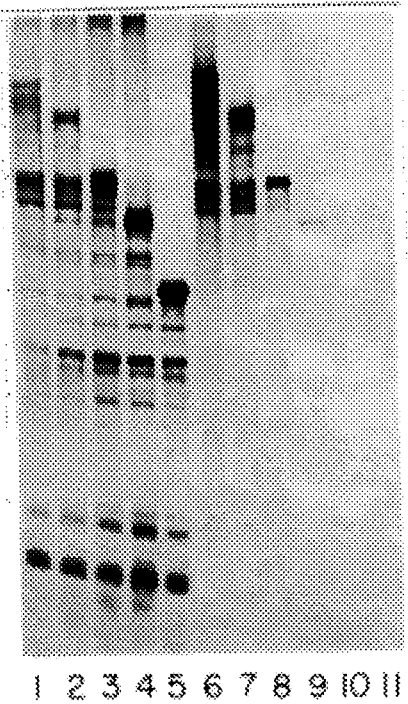
FIG. 7A presents the determination of the E1A binding site on p300. A series of DNA templates for in vitro transcription/translation with progressive 5' deletions was prepared by fusing in frame ATG translation initiation codons to restriction enzyme sites (indicated at the top) located in the C-terminal part of the p300 cDNA. In this way, templates with progressive 5' deletions were generated. All templates were linearized with Asp 718 which cuts in the polylinker downstream of the p300 cDNA. 10 ul of $^{35}$S labelled in vitro translation products from these templates (lanes 1–5 shows 1 ul of each of the translates) were mixed with cold extract of ~4×10$^6$ 293 cells (as a source for E1A) followed by immunoprecipitation with the anti-E1A monoclonal antibody, M73 (lanes 6–10). In lane 11, as a control, the translation products directed by the 5.3 ATG template were mixed with 293 cell lysate and then immunoprecipitated with Pab 419.
Figure 7B:
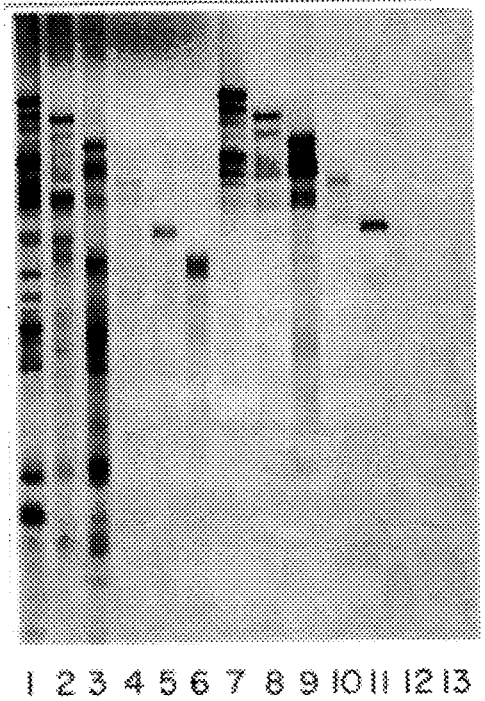
FIG. 7B presents additional data for determination of the E1A binding site on p300. The Bgl II ATG template was cleaved with the restriction enzymes denoted at the top, in order to generate p300 protein fragments with progressive C-terminal deletions. E1A binding assays were performed as described in FIG. 6A. Lanes 1–6 show the input of the translates, and lanes 7–12 shows the translation products recovered after mixing with cold 293 extract and immunoprecipitation with M73. In lane 13, translation products from the Bgl II ATG template linearized with Asp 718 were mixed with 293 extract and immunoprecipitated with Pab 419 (control).
Figure 7C:
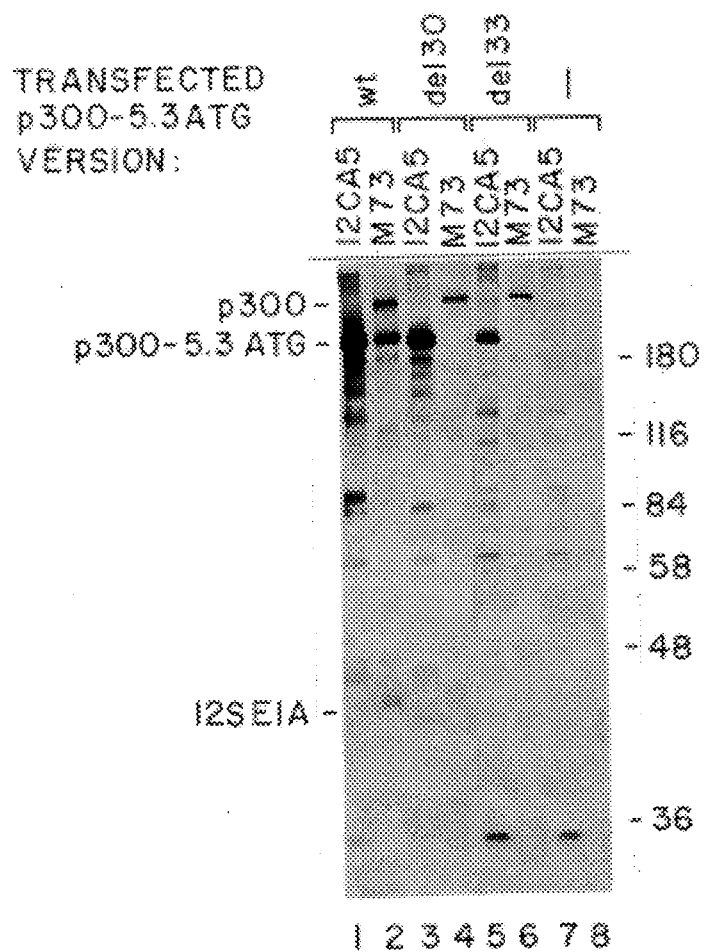
FIG. 7C presents additional data for determination of the E1A binding site on p300. Two internal deletion mutants removing part of the E1A binding region of p300 (termed del30 and del33) 6 were generated in the context of the 5.3 ATG plasmid, which encodes a 200 kD C-terminal fragment of p300. Hemagglutinin tagged versions of the wild-type 5.3 ATG plasmid and of the two deletion mutants were transfected into U-2 OS cells together with an expression vector coding for the 12S E1A product. Cells were labelled with $^{35}$S-methionine, extracted, and one half of the lysate of each dish was immunoprecipitated with 12CA5 (anti-HA monoclonal antibody). The other half was immunoprecipitated with M73. In lanes 7 and 8, lysates from untransfected U-2 OS cells were immunoprecipitated with 12CA5 and M73, respectively.
Figure 7D:
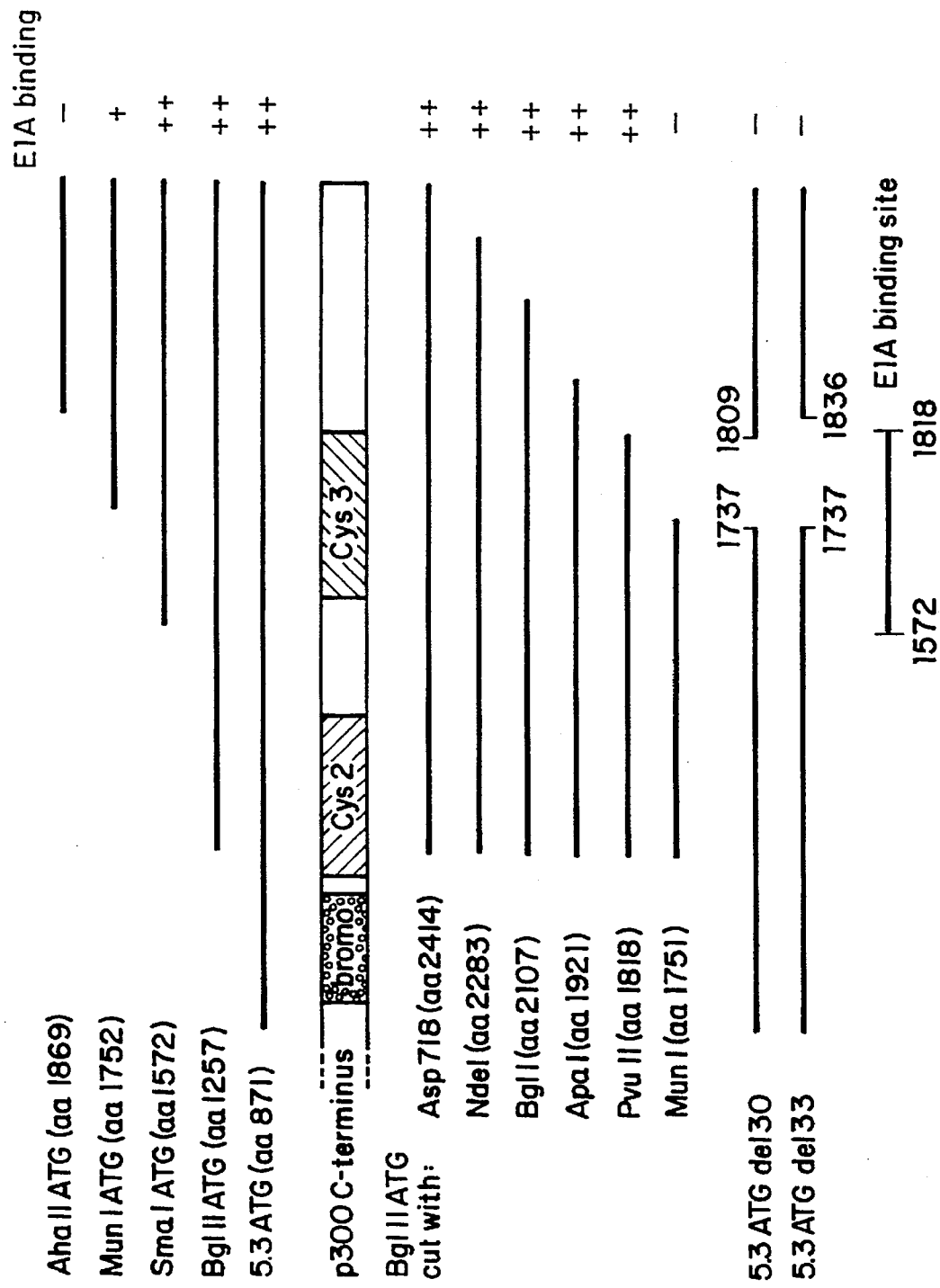
FIG. 7D is a schematic representation of the deletion mutants used in panels A–C. The E1A binding properties of each of them is summarized on the right.

The templates for in vitro transcription/translation were constructed by fusing oligonucleotides containing an eukaryotic consensus translation initiation signal to the restriction sites indicated in FIG. 7D.

The two internal deletions in the E1A binding region of p300 (del 30 and del 33) were generated by resecting Eco 47 III cut pBluescript p300-1 DNA with Bal 31 followed by digestion with Hind III to release the C-terminal part of the p300 cDNA. This fragment was then ligated to pBluescript p300-1 cleaved with Eco 47 III and Hind III to create plasmids containing full length p300 with unidirectional Bal 31 deletions. Deletion endpoints were determined by sequencing. For the experiment in FIG. 7C, the two internal deletions were introduced into the 5.3 ATG context by transferring a Bgl II-Hind III fragment spanning the deletions from the full length construct into the 5.3 ATG plasmid cleaved with the same two restriction enzymes. Both constructs were expressed in mammalian cells from the CMVβ expression vehicle.

$^{35}$S labelled products from in vitro translation reactions were mixed with cold cell lysates derived from the E1A expressing cell line 293. The ability of the translation products to associate with E1A was assayed by immunoprecipitation with the anti-E1A antibody M73. Analysis of the 5' deletion series indicated that proteins beginning at the Mun I site can still interact with E1A (FIG. 7A, lane 9), though with decreased efficiency compared to longer proteins (compare lanes 6–8 with lane 9). This conclusion takes into account the lower specific activity of the shorter translation products as compared to the longer ones (owing to the presence of fewer methionine residues). Once sequences up to the Aha II site were removed, translation products no longer bound E1A (FIG. 7A, lane 10). Interpreting these results conservatively, the 5' border of the p300 region required for efficient interaction with E1A appears to be located between the Sma I and Mun I sites. Analysis of the 3' border of the E1A binding site placed it at the Pvu II site (FIG. 7B). Translation products ending at the Mun I site were unable to bind E1A (lane 12, FIG. 7B). The p300 sequences defined by this approach overlap the third cys/his-rich region located between amino acids 1572 and 1818 (see FIG. 7D).

To probe the relevance of the in vitro determined E1A binding site in vivo, we prepared two mutants bearing internal deletions which remove the second half of the above noted cys/his-rich region. They were inserted into the 5.3 ATG backbone used before for studying the genetics of the interaction between E1A and cloned p300 (FIG. 2) and were termed 5.3 ATG del30 and del33 (see FIG. 7D for schematic drawing). U-2 OS cells were transiently transfected with an expression vector for the 12S E1A product along with the wild-type and either one of the internal deletion mutants. All three proteins were produced as HA-tagged 200 kD derivatives. Lysates from $^{35}$S labelled transfected cells were split in half and immunoprecipitated, in parallel, with the anti-HA antibody 12CA5 and with the anti-E1A antibody M73, respectively. The 12CA5 immunoprecipitation was performed to monitor the expression levels of the three different p300 variants. FIG. 7C shows that all three p300 versions were present at comparable levels (lanes 1, 3, 5). However, only the wild-type 200 kD protein bound to E1A (lane 2). At the same time, endogenous p300 coprecipitated efficiently with E1A (see lanes 2, 4 and 6), demonstrating that the failure to detect E1A bound to the two internal deletion mutants was not due to immunoprecipitation difficulties. The result from this experiment supports the notion that the third cys/his-rich region (amino acids 1572–1818) represents the binding site for E1A on p300. It remains to be seen whether this segment of p300 by itself is sufficient to interact with wild-type and mutant E1A proteins in the same way as does full length p300.

EXAMPLE IV

Figure 8A:
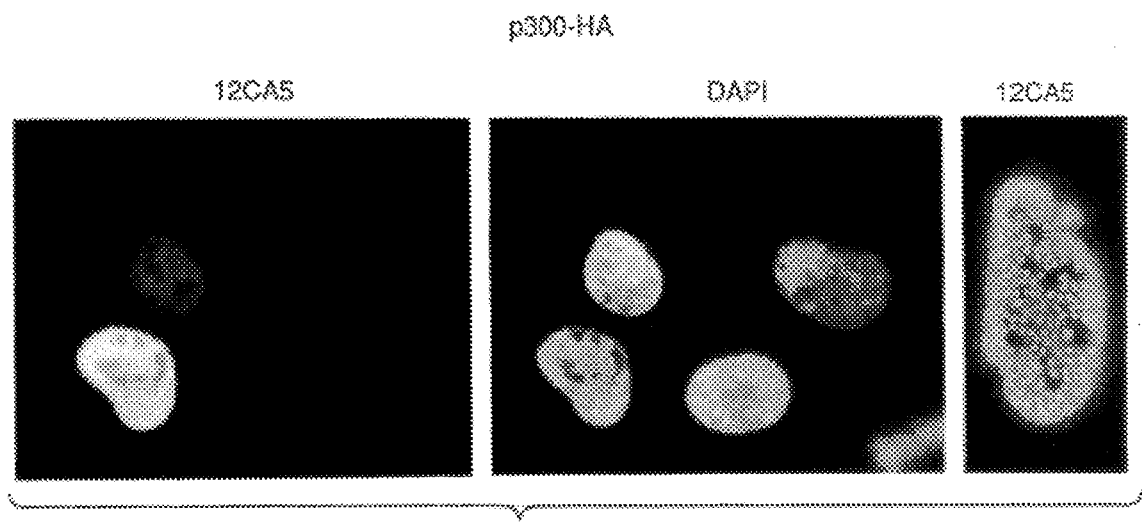
FIG. 8A presents an immunofluorescence analysis of the subcellular location of full length and truncated p300 molecules. U-2 OS cells transiently transfected with a vector encoding HA-tagged full length p300 were fixed and stained with 12CA5 anti-HA antibody followed by rhodamine conjugated rabbit anti-mouse secondary antibody (left). The same section as on the left is shown in the middle after DAPI staining. The panel at the right shows an enlarged picture of a nucleus from transfected U-2 OS cells to visualize the speckles that became apparent after overproduction of p300.

Nuclear Localization of p300 Protein.

p300 is a nuclear protein (Yaciuk et al., 1991, supra). As expected, full length, HA-tagged p300 was exclusively nuclear, as shown by immunofluorescence in FIG. 8A. U-2 OS cells were seeded on coverslips and transfected with expression vectors encoding HA-tagged p300 versions. They were fixed in 3% paraformaldehyde/2% sucrose in PBS for 10min at room temperature. Subsequently, cells were washed twice with PBS, followed by permeabilization in ice cold Triton X-100 buffer (50 mM NaCl,3 mM MgCl$_2$, 200 mM sucrose, 10 mM Hepes pH 7.4 and 0.5% Triton X-100) for 5 min. Antibody incubations (with anti-HA tag monoclonal antibody 12CA5) were for 30 min at 37° C., followed by three washes in PBS, 5 min each. Secondary antibodies were rhodamine-conjugated goat anti-mouse IgG (Boehringer Mannheim). After another three 5 min washes in PBS, slides were incubated for two min in a DAPI solution (0.5 µg/ml DAPI in PBS) in order to stain DNA, rinsed twice with PBS and mounted. Microscopy was carried out using a Nikon Microphot SA microscope equipped with a PlanApo 60× oil immersion objective.

Figure 8B:
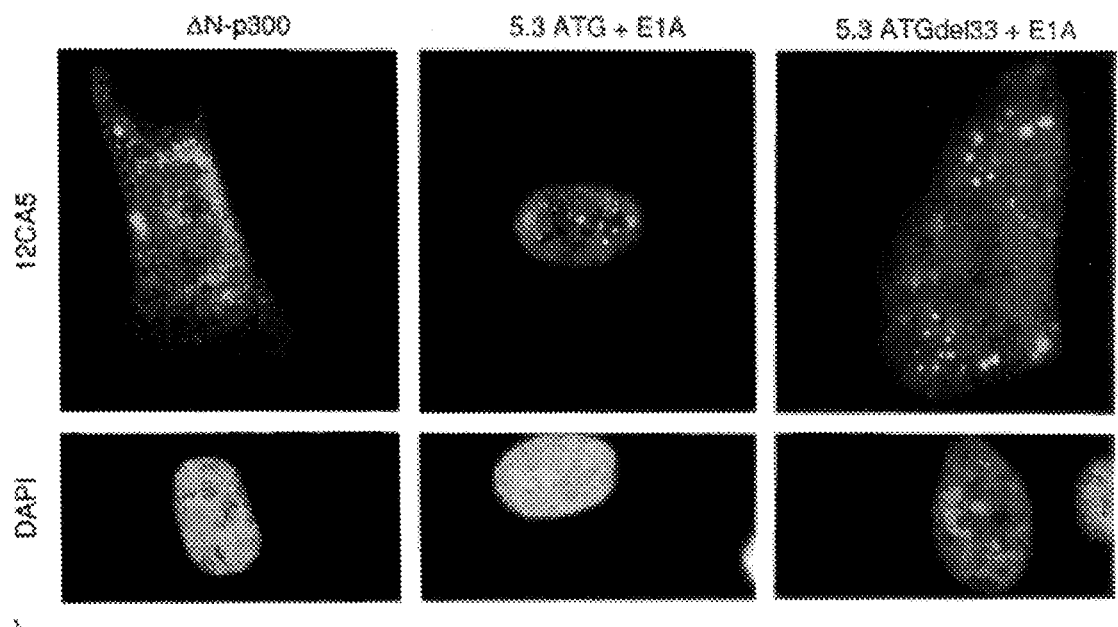
FIG. 8B shows additional immunofluorescence analysis of the subcellular location of p300. The top row shows the intracellular distribution in U-2 OS cells of the HA-tagged p300 version indicated above each of the three panels. The primary and secondary antibodies were as described in FIG. 8A. Note that for the cytoplasmic p300 derivatives, speckles are now visible in the cytoplasm. The bottom row shows the DAPI staining patterns of the cells displayed above.

A p300 protein missing 140 amino acids at the N-terminus (termed Δ-N-p300) was predominantly, albeit not exclusively, cytoplasmic (FIG. 8B, left panel), as was the 200 kD C-terminal fragment encoded by the 5.3 ATG chimera (data not shown). Interestingly, in the presence of E1A, all p300 derivatives capable of associating with it, including those which were otherwise cytoplasmic, were again exclusively nuclear (e.g. the 5.3 ATG chimera in FIG. 8B, middle). The rescue of the nuclear transport defect of N-terminally truncated p300 molecules was dependent on their ability to interact with E1A. This is illustrated by the mutant 5.3. ATGdel33, which cannot bind E1A (see FIG. 7C) and, hence, can no longer be transported to the nucleus by E1A (FIG. 8B, right panel). Since E1A mutants unable to interact with p300 also failed to transport N-terminally truncated versions of p300 to the nucleus efficiently (data not shown), cytoplasmic p300 versions are likely transported to the nucleus as E1A complexes via an E1A dependent piggy back mechanism. Analysis of the first 140 amino acids of p300 suggested that residues 11–17 represent an N-terminal nuclear location signal (see FIG. 4A). This sequence represents the only cluster of basic amino acids in this region and fits the consensus sequence for one subtype of nuclear location signals (Dingwall and Laskey, 1991, Trends Biochem. Sci. 16:478–481). It is likely that p300 harbors a second nuclear targeting signal, because some of the Δ-N-p300 molecules were still able to reach the nucleus.

Prominent anti-p300 reactive speckles were visible in transfected cells in the nucleus or distributed throughout the cell, depending on the localization of the relevant p300 species. We suspect that these speckles represent aggregates of p300 which perhaps arise because of the high cysteine content of p300 coupled with its overproduction. This difficulty with transfected p300 could also help to explain why the peptide maps from transfected p300 exhibited small deviations from the pattern observed with endogenous 300 kD protein. In this model, p300 aggregation after overproduction could inhibit its posttranslational modification such that the pattern resulting from limited proteolysis is slightly different from that observed with the correctly modified endogenous protein.

EXAMPLE V

Rescue of Enhancer Repression by Mutant p300 Protein.

p300 protein was used to rescue the activity of the SV40 enhancer when it was specifically repressed by E1A. Previous studies had shown that E1A can specifically repress the SV40 enhancer, but not its promoter (Borelli et al., 1984, supra; Velcich and Ziff, 1985, supra). A luciferase reporter gene driven by the SV40 enhancer/promoter was transfected into U-2 OS cells together with either an expression vector for 12S E1A, or a combination of vectors encoding full length p300 and 12S E1A. In all cases, luciferase activity was normalized to the β-galactosidase activity of a cotransfected lacZ gene. Different amounts of E1A expression vector were used in order to elucidate the range of E1A concentrations within which p300 overcame E1A imposed enhancer repression. The activity of the SV40-luciferase reporter plasmid in the absence of any E1A was given arbitrarily a value of 100.

The plasmid pGL2-control (Promega) was used as a reporter construct. It contains the luciferase gene driven by the SV40 promoter and the SV40 enhancer which is inserted downstream of the luciferase gene. 5 µg of pGL2-control and 1 µg of pCMVlacZ were transfected with varying amounts of CMV12SE1A and 8 µg of pBluescript or 8 µg of the indicated p300 expression vector, respectively. It was important not to use too much of the p300 expression vector, because less restoration of SV40 enhancer activity was obtained when higher amounts of this expression plasmid were utilized, probably due to increased p300 aggregate formation. The final DNA concentration in the transfection mixture was between 15 and 20 µg, depending on the amount of E1A expression plasmid included. Cell lysis, β-galactosidase and luciferase assays were carried out as described (Ausubel et al., 1987, supra). In each experiment, one sixth of the cells of a transfected dish were lysed directly in SDS-sample buffer, and the E1A levels were monitored by Western blotting. The anti-E1A monoclonal antibody M73 was utilized as primary antibody. The secondary antibody was a goat anti-mouse antibody conjugated to alkaline phosphatase (Boehringer Mannheim).

Figure 9A:
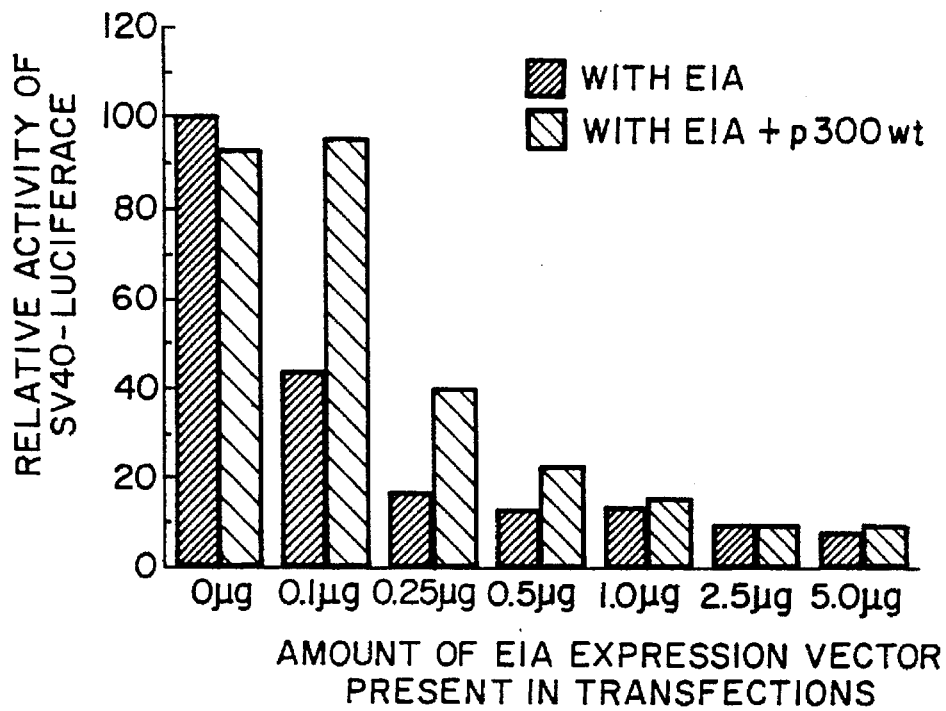
FIG. 9A is an analysis of the role of p300 in the transactivation potential of the SV40 enhancer. A luciferase reporter plasmid driven by the SV40 enhancer/promoter (5 μg), a plasmid encoding β-galactosidase (1 μg, internal standard), and increasing amounts of an expression vector for 12S E1A (see numbers below each pair of bars) were transfected into U-2 OS cells either in combination with 8 μg of pBluescript carrier DNA (black bars) or in combination with 8 μg of an expression vector encoding full length p300 (bars with horizontal lines). All luciferase values were normalized to each other based on the respective β-galactosidase activity. The luciferase activity obtained with the reporter alone was set to 100, and all other activities were expressed relative to this sample. The data in this figure represent the average of four independent experiments.
Figure 9C:
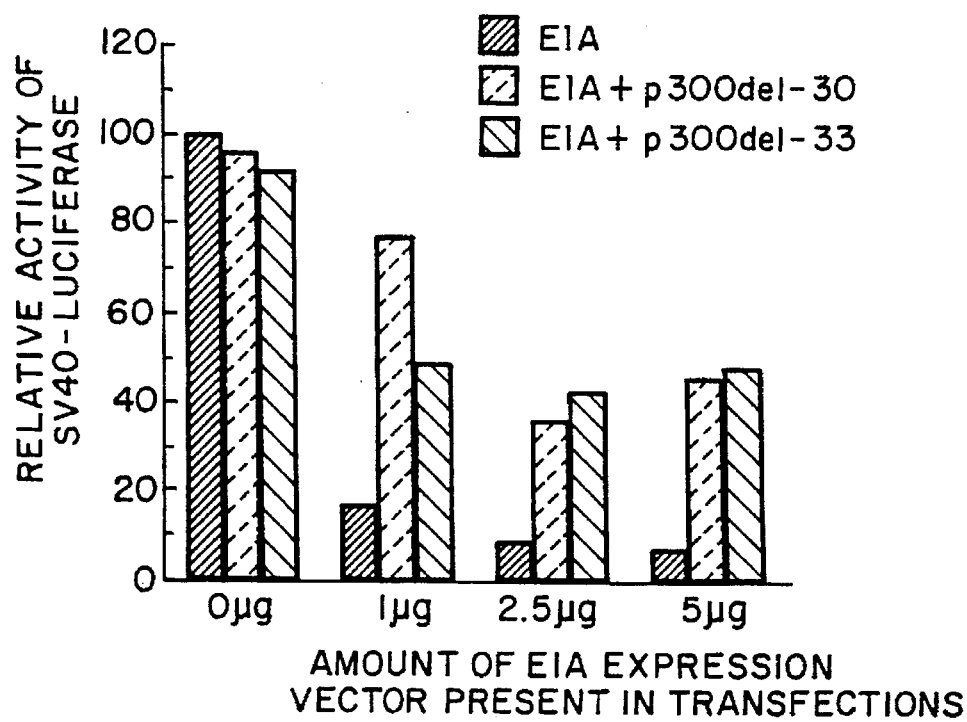
FIG. 9C shows lucerifase levels in U-2 OS cells transfected as described in FIG. 9A, except that instead of the expression vector for wild-type p300, the same vector encoding either deletion mutant p300del30 (stippled bars) or deletion mutant p300del33 (lined bars) was used. The bars in this figure represent the average luciferase activity from five independent experiments.
Figure 9B:
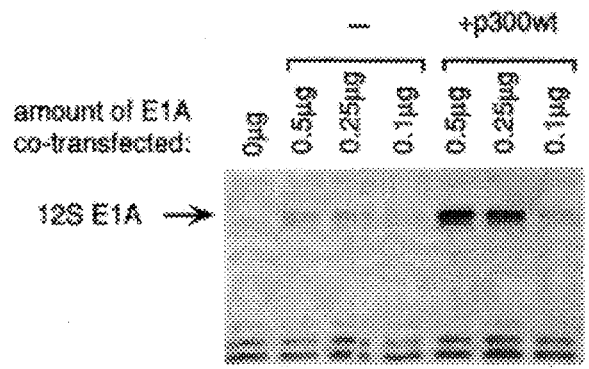
FIG. 9B is a Western blot showing expression levels of E1A in the transfection experiments carried out in FIG. 9A. One sixth of the cells from the 10 cm dishes transfected for the experiment described in FIG. 9 were subjected to Western blotting. The membrane was probed with the anti-E1A monoclonal antibody, M73. The amount of E1A expression plasmid present in the transfection mixture is indicated on the top.

The results of the enhancer rescue assays showed that, at low concentrations of E1A-encoding DNA (0.1 and 0.25 µg), suboptimal SV40 enhancer repression was observed, and cotransfected p300 overcame the repressive effect of E1A by about a factor of 2 (FIG. 9A). Western blots carried out in parallel indicated that E1A protein levels were consistently 2–3 fold elevated in cells where p300 was also present, as compared to cells which were transfected with only the reporter plasmid and E1A (FIG. 9B). Thus, the mild relief of E1A-mediated SV40 enhancer repression by transfected p300 does not occur by reducing the levels of E1A. However, it may be that the positive effect of p300 on the SV40 enhancer is linked to the functional sequestration (and inactivation) of E1A bound to p300 in aggregates such as described in FIG. 8. This sequestration of E1A might be sufficient to account for the reactivation of the enhancer. Similarly, the elevated levels of E1A in the presence of p300 could be attributed to a stabilization of the normally short lived E1A molecules in p300-E1A aggregates due to shielding from proteolysis. At high concentrations of E1A expression vector (2.5 and 5 µg), the enhancer was completely repressed, and cotransfected p300 was unable to stimulate transcription, indicating that E1A was in excess over p300 under these circumstances.

Figure 9D:
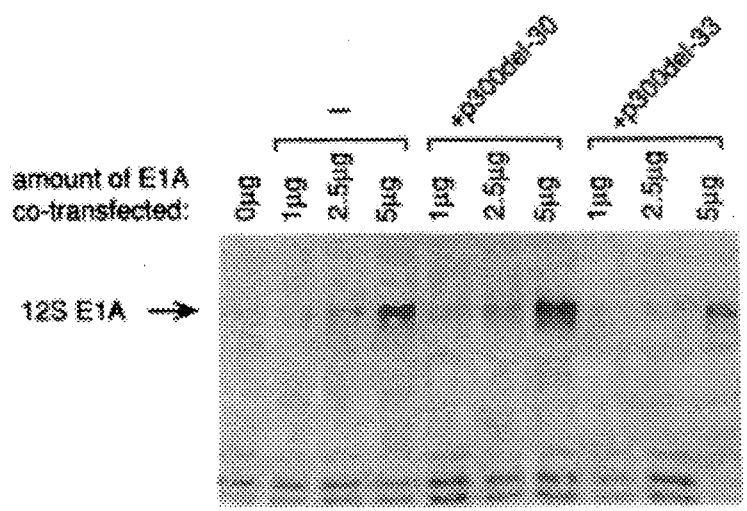
FIG. 9D is a Western blot visualizing the expression levels of the E1A protein in the transfection experiments performed in FIG. 9C.

To circumvent the possible inactivation of E1A, we switched to p300 molecules unable to associate with E1A. For this purpose, the del30 and del33 deletion mutations were introduced into full length p300. The rationale behind this approach was to sequester the pool of endogenous p300 in E1A complexes and to see whether the exogenous p300, defective for binding E1A, can substitute for the endogenous p300 and restore SV40 enhancer activity. As shown in FIG. 9C, both p300del30 and p300del33 efficiently relieved E1A-imposed SV40 enhancer repression, even at the very high concentrations of E1A used in these experiments. On average, about half of the original enhancer activity could be restored. Western blots carried out in parallel confirmed that E1A levels were comparable within these assays, whether or not the p300 internal deletion mutants were present (FIG. 9D). We conclude that p300 can bypass E1A-imposed repression and reactivate the SV40 enhancer, strongly arguing that p300 itself is directly involved in modulating the activity of the SV40 enhancer.

EXAMPLE VI

Methods of Detecting Mutant p300 Gene and/or Protein.

The invention provides for early diagnosis of neoplasm, i.e., tumorigenicity, in a tissue sample by detection of an absence of wild-type p300 protein or gene, or by detection of the presence of non-wild-type p300 protein or gene, in a tissue sample, using techniques well-known in the art. Detection of a mutant p300 gene or protein may be accomplished according to a number of techniques, as follows.

For example, for detection of wild-type or non-wild-type p300 protein, proteins contained in a tissue sample suspected of being or known to be neoplastic are analyzed by Western blot analysis using any one of the monoclonal antibodies disclosed herein. The protein identified in the tissue sample by Western blot analysis will be determined to be wild-type or mutant based on (1) their ability to be detected with one or more of the antibodies disclosed herein, and/or (2) their mobility in the blot relative to the mobility of wild-type p300. Failure to detect a protein that comigrates with wild-type p300 will be indicative of mutant p300; that is, mutant p300 may lack the epitope for which the antibody is specific, and thus the mutant protein will not be detected by that antibody, or mutant p300 may contain a deletion, substitution or insertion mutation, of one or more amino acids, that causes the mutant protein to migrate aberrantly in the Western gel relative to wild-type p300.

The mutant gene or protein may be characterized by isolating and sequencing the p300 allele present in the tumor tissue. For example, the polymerase chain reaction (PCR) may be used to amplify DNA corresponding to the mutant p300 gene. Mutant genes may also be characterized by generating cDNA corresponding to mRIqA from the tumor tissue, and isolating p300 encoding cDNA using a probe based on the p300 nucleotide sequence provided herein.

A mutant p300 gene may also be detected using mismatch detection. A labeled riboprobe (sense or antisense) complementary to the wild-type p300 gene is annealed to either mRNA or DNA isolated from tumor tissue, and then cleaved with a nuclease, e.g., RNase, that cleaves the hybrids only at sites of mismatch. The cleaved annealed hybrids are then subject to electrophoresis under non-denaturing conditions. Mismatches are detected as bands on the gel that are smaller than full-length duplex p300.

Where specific mutations of p300 are known, such mutations may be detected using allele-specific p300 probes, i.e., that contain corresponding specific p300 mutation(s). The presence of a specific mutation is confirmed by hybridization of the allele-specific probe with DNA from a tumor tissue. The tumor tissue DNA may be PCR-amplified for the hybridization reaction p300 gene mutations may also be detected using restriction fragment length polymorphism (RFLP) analysis. A deletion of all or part of the p300 gene may be detected by the absence of gene expression products, i.e., mRNA or protein, or the inability of p300 to bind to E1A or a monoclonal antibody specific for p300, as described herein.

Determination of the mutant gene nucleotide sequence and comparison to the wild-type sequence provided herein will allow identification of genetic mutations in the p300 gene.

EXAMPLE VII

Generation of p300 Gene and Protein Mutants p300 mutant proteins will be useful as immunogens for generating monoclonal antibodies that selectively bind a mutant protein, but do not recognize wild-type p300 protein. p300 mutant genes will be useful as probes for determining allele-specific genetic mutations, e.g., in analysis of a neoplastic tissue, or as genes useful in gene therapy to alter or prevent transformation to a neoplastic state. Such mutants may be p300 proteins that are uncoupled from the cellular signal transduction pathways, i.e., that may trigger constitutive activation of genes associated with the terminal differentiation state or prevent activation of key genes, e.g., the c-jun promoter.

Deletions and point mutations of p300 can be generated, e.g., via PCR mutagenesis using the appropriate primers or by site directed mutagenesis, as described in Kunkel, T. A. 1985, Rapid and efficient site-specific mutagenesis without phenotypic selection. Proc. Natl. Acad. Sci 82, 488–492, hereby incorporated by reference.

In addition to the p300 mutations and deletions described elsewhere herein, the following p300 mutations or deletions may be made in the DNA encoding p300 and the resultant mutated protein tested according to the invention and as described herein. Deletions within the following four regions of p300 may result in transdominant p300 molecules that interfere with the activity the endogenous p300 protein. These regions include: (1) the first cys/his rich region (amino acids 346–415, inclusive); (2) the bromodomain (amino acids 1070–1134, inclusive); (3) the second cys/his rich region (amino acids 1162–1452, inclusive); and (4) the third cys/his rich region, i.e., the E1A binding domain (amino acids 1638–1807, inclusive).

Other regions of p300 that may be mutated and tested according to the invention include the phosphorylation sites of the protein, as presented in Table 1. Whether or not a certain site is indeed phosphorylated in vivo can be determined by phosphopeptide and phosphoamino acid analysis.

p300 mutants that are especially useful according to the invention are those that constitutively activate differentiation and tissue-specific genes, or those that constitutively repress the c-jun promoter, as described below. These types of mutants would effectively uncouple p300 from the cellular signal transduction and/or cell cycle machinery. Constructs expressing such altered p300 molecules may be useful in gene therapy to treat tumors. Delivery of the gene to a target site may be accomplished via any one of a variety of gene delivery systems available in the art. Thus, the construct, when delivered appropriately, would target tumor tissue to avoid toxic side-effects of the mutant p300 in normal cells. Cell-targeting systems are also known in the art. Mutants of p300 may contain amino acid substitutions, deletions, or truncations of the molecule. Amino acid alterations of p300 may results in, e.g., failure to correctly phosphorylate the protein, as described in Table 1 below.

Table 1 describes representative sites in the p300 protein that are candidate sites for site-directed mutagenesis. cAMP dependent kinase sites contain two basic amino acids followed by a generic single residue (any amino acid), followed by a serine or threonine residue. Protein kinase C sites contain a consensus site comprised of a serine or threonine residue, followed by a generic single residue (any amino acid), followed by a basic amino acid. A cell cycle kinase (CDK) or mitogen-activated protein kinase (MAP) site contains a serine or threonine residue followed by a proline residue.

TABLE 1

1. cAMP dependent kinase sites
    -aa 647 - 650:KRRT
    -aa 1554 - 1557:KKTS
    -aa 1731 - 1734:RRLS
    -aa 1772 - 1775:KRKT
2. Protein kinase C sites
    -aa 12 - 14:SAK
    -aa 371 - 373:TMK
    -aa 384 - 385:SGR
    -aa 395 - 397:SSR
    -aa 1044 - 1046:SKK
    -aa 1101 - 1103:TIK
    -aa 1135 - 1137:TSR
    -aa 1232 - 1234:SKR
    -aa 1279 - 1281:SAR
    -aa 1282 - 1284:TRK
    -aa 1289 - 1291:SAK
    -aa 1295 - 1297:STR
    -aa 1322 - 1324:TVR
    -aa 1329 - 1331:SDK
    -aa 1476 - 1478:SER
    -aa 1497 - 1499:SAK
    -aa 1516 - 1518:SIK
    -aa 1556 - 1558:TSK
    -aa 1581 - 1583:SQK
    -aa 1643 - 1645:SLR
    -aa 1730 - 1732:SRR
    -aa 1938 - 1940:TQR
    -aa 2057 - 2058:TLR
    -aa 2315 - 2317:SPR
    -aa 2328 - 2330:SPR
3. CDK or MAP kinase sites

EXAMPLE VIII

Methods of Screening for Inhibitors or Enhancers of p300-dependent Transcriptional Activation.

The invention encompasses methods of screening for compounds that inhibit or enhance p300-dependent transcription.

The rational underlying a screening method for a p300 enhancer/activator or inhibitor is as follows. p300 appears to function as a transcriptional adapter for tissue specific genes, e.g., for neurons, muscle, fat cells, B-lymphocytes, keratinocytes, etc. During differentiation of cells, p300 may be modified to become a promoter activator for promoters that drive expression of genes associated with terminal differentiation of a cell. Tumor cells are usually arrested in a relatively undifferentiated state; thus, genes associated with terminal differentiation never become activated. p300 may become inhibited or fail to become activated in the undifferentiated state. Compounds that activate/enhance p300 would then be useful for helping to trigger terminal differentiation.

Examples of candidate enhancers of p300 include but are not limited to kinase inhibitors, e.g., staurosporine, a protein kinase C inhibitor (Cal. Biochem., San Diego, Calif.), and butaryate, a cAMP-dependent kinase inhibitor (Sigma Corp.). An enhancer of p300 would be useful for compensating for a defective p300 protein or gene, and thus for rescuing a p300-defective cell from an undifferentiated or transformed state, or for generally increasing the apparent ability of p300 to establish a differentiated state. An inhibitor of p300 would be useful for, e.g., preventing c-jun gene activation.

One screening method may include a p300-transcriptional activation system in which p300 is fused to a DNA binding domain that is operationally associated with a reporter gene, e.g., secreted alkaline phosphatase. A p300/DNA binding domain fusion may be necessary because p300 protein does not appear to interact directly with DNA. Two examples of DNA binding domains useful according to this aspect of the invention are the yeast transcription factor ga14 domain and bovine papilloma virus E2 domain.

An alternative transcriptional activation system may include a tissue-specific promoter operationally associated with a reporter gene, wherein the gene encoding p300 is co-transfected with the tissue-specific promoter/reporter gene construct into mammalian cells. In both transcriptional activation systems, compounds that increase the read-out of the reporter gene are indicated as activators/enhancers of p300 activity.

The screening methods also include an expression system involves the ras oncogene signalling pathway and the c-jun gene. c-jun is a key target gene in the ras oncogene signalling pathway. Ras is activated by mutations in about 40% of human tumors. Lloyd et al., 1991, Nature 352;635 report that inactivation of c-jun leads to reversal of the neoplastic state of ras-transformed cells. There is evidence that p300 represses the c-jun promoter. The presence of E1A in a cell induces the c-jun promoter. This induction depends upon an intact p300 binding site on E1A. (see Van Dam et al., 1990, Mol. & Cell. Biol. 10:5857). In addition, it has been observed that c-jun is transiently induced upon serum stimulation in normal cells, but is constitutively active in many transformed cells. Thus, a screening method of the invention may involve inactivation of c-jun by p300. Candidate compounds may then be screened for their ability to interfere with inactivation of p300 in the Ras signalling pathway.

A screening method would thus include a mammalian expression system in which wild-type p300 is present and activates a p300-dependent genetic regulatory element, such as the c-jun promoter, that is operationally associated with a reporter gene (e.g., alkaline phosphatase). Therefore, where no inhibitor or enhancer of p300 is present, the reporter gene is expressed at a basel level. For example, the expression system may comprise ras-transformed mammalian cells cotransfected with p300-encoding DNA and the c-jun promoter operationally associated with the reporter gene. As used herein, "base" level does not refer to an actual in vivo level of gene expression, but rather to a level of gene expression in the absence of a compound (enhancer or inhibitor of p300) in the ex vivo assay.

Screening of candidate inhibitors or enhancers of p300 is carried out by providing to the expression system a candidate compound for a time and in a concentration sufficient to inhibit or enhance reporter gene expression to a level that is below or above the basal level, respectively. Expression of the reporter gene below the base level is then indicative of an inhibitory effect of the candidate compound. Similarly, expression of the reporter gene above the basal level is indicative of an enhancing effect of the candidate compound.

EXAMPLE IX

Role of p300 in Tumor Suppression

The observation that p300 maps to a segment of 22q13 suggests a possible role for p300 in tumor suppression. p300 may be encoded by a tumor suppressor gene based on the precedent of another E1A associated protein, the retinoblastoma protein. Therefore, it was of interest to map its chromosomal location to determine whether it maps near a cytogenetic location known or suspected to harbour a tumor suppressor gene. The 4.5 kb N28 cDNA fragment (see FIG. 1A) was used for fluorescence in situ hybridization (FISH) to metaphase chromosome preparations from normal human lymphocytes. Methods for chromosome mapping of the p300 gene were essentially as described elsewhere (Lawrence et al., 1988, Cell 52:51–61; Johnson et al., 1991, Methods in Cell Biology, Vol 35:73–99, San Diego), and will be only briefly outlined here. A human cDNA probe for p300 (N28) was labelled by nick-translation with digoxygenin dUTP (BRL) and detected after hybridization with fluorescein anti-digoxygenin antibody. Elongated metaphase and prometaphase chromosomes were prepared by standard procedures from normal peripheral blood lymphocytes treated with methotrexate for 18 hours, bromodeoxyuridine (BrdU) for 6 hours to enhance banding, and finally a ten minute colcemid treatment. Samples were hybridized with 5 μg/ml labelled probe in 50% formamide, 2×SSC at 37° C. For hybridization with two probes simultaneously, the Chr. 21 marker probe was labelled with biotin and visualized with rhodamine-avidin. Samples were visualized on a Zeiss Axioplan microscope and images captured using a CCD camera connected to a silicon graphics workstation.

Figure 3:
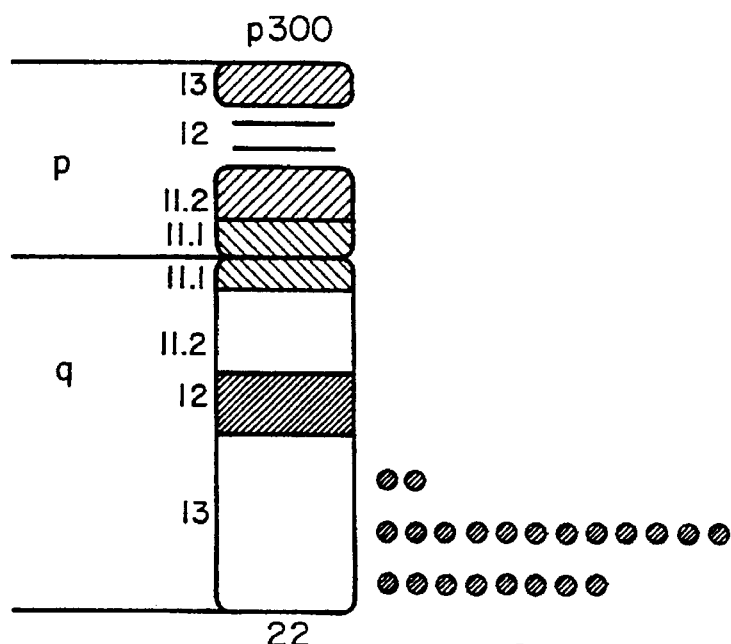
FIG. 3 shows the chromosomal location of the p300 gene. An ideogram is shown, revealing the location of p300 gene signals on chromosome 22, as scored based on BrdU enhanced DAPI banding patterns of 22 different images. Although band q13.2 was not visible in these preparations, the localization of the gene to the distal half of the 22q13 band supports its finer localization to positions 22q13.2-q13.3.

The chromosome mapping results showed that approximately 90% of cells showed label, with label at a single chromosomal site on a homologous pair of E group chromosomes. DAPI staining of chromosomes initially indicated that this was human chromosome 22, and the distinction from chromosome 21 was confirmed by simultaneous two-color hybridization of a second sequence known to map on chromosome 21, which clearly mapped to a different chromosome than the p300 gene. As summarized in FIG. 3, DAPI banding analysis of BrdU incorporated chromosomes in over 20 metaphase spreads showed that the p300 gene consistently localized in band 22q13, predominantly in the distal half of that chromosome band corresponding to 22q13.2-q13.3.

The role of p300 in tumor suppression is supported by the proximate location of p300 to the recently identified neurofibromatosis 2 gene (Rouleau et al., 1993, Nature 363:515–521; Trofatter et al., 1993, Cell 72:791–800). The neurofibromatosis 2 gene is localized proximal to p300 at 22q12. Furthermore, deletions including the band 13 region of chromosome 22 have been correlated with certain types of colon cancer (Okamoto et al., 1988, Nature 331:273–277) and gliomas (Jenkins et al., 1989, Cancer Genet. Cytogenet. 39:253–279). In addition, chromosomal breakpoints in the band 13 region of chromosome 22 have been found in acute nonlymphocytic leukemia (ANLL) type M2.

These observations suggest that p300 may play a role in the evolution of one or more neoplastic disorders. Loss or mutation of p300 may be a relatively frequent event in certain human tumors.

Detection of a p300 gene or protein deletion or mutation may aid physicians in diagnosing potential or early tumor formation, and in confirming the identity of certain late-stage tumors. Thus, mutation or loss of the p300 gene or protein may be detected in tumor tissue or body fluids, such as serum, saliva, and urine. Diagnostic methods may be designed which use p300 protein or gene detection and employing one or more of these body samples to detect carcinogenesis at a variety of stages. Early detection of tumors as well as evaluation of the progress of a treatment may be assessed using such diagnostic methods.

EXAMPLE X

Production of Monoclonal Antibody Specific for Epitope of p300 Protein.

A monoclonal antibody specific for a given epitope of p300 may be prepared according to standard procedures for generation of monoclonal antibodies, using a p300 protein fragment encompassing that epitope as an immunogen. The resultant monoclonal antibodies are then characterized according to their binding specificities. Monoclonal antibodies specific for epitopes within the carboxy terminus of p300 are particularly useful according to the invention, and are constructed as follows. As used herein, the carboxy terminus of the p300 polypeptide is defined as the carboxy terminal amino acids 1572–2371, inclusive, and preferably the carboxy terminal amino acids 1819–2371, inclusive. Thus, an epitope within the carboxy terminus of p300 will be contained within the region encompassing these residues.

A GST-p300 fusion protein encompassing amino acids 1572–2371 of p300 was injected intraperitoneally into Balb/c mice. Spleen cells of positive animals were fused to NS-I cells according to standard procedures (Harlow and Lane, 1988, Antibodies: A Laboratory Manual, Cold Spring Harbor, N.Y.). Supernatants from the resulting hybridoma colonies were screened for their ability to immunoprecipitate $^{35}$S labelled in vitro translation products derived from the Bgl II ATG template. The epitopes recognized by the monoclonal anti-p300 antibodies were mapped according to conventional epitope mapping procedures, using a series of in vitro translation products encoded by templates carrying progressive 5' and 3' deletions. Results of the mapping experiments are presented in Table 2.

TABLE 2

| monoclonal antibody | subclass | epitope (amino acids) |
|---|---|---|
| RW102 | IgG3 | 2023–2107 |
| RW105 | IgG1 | 1921–2023 |
| RW109 | IgG1 | 1868–1921 |
| RW128 | IgG1 | 2107–2283 |
| RW144 | IgG1 | 1921–2023 |

Antibodies specific for an epitope of the carboxy terminus of p300 is particularly useful in identifying and characterizing p300, e.g., in immunoassays such as immunoprecipitations and immunofluorescence. p300 carboxy terminal-binding antibodies have considerable advantage over antibodies that bind elsewhere in the p300 molecule because certain cellular and viral proteins bind p300 distal from the carboxy terminus. Thus, p300 carboxy terminal-binding antibodies may be used in the identification and characterization of p300 binding proteins without interfering with the binding of these proteins to the p300 molecule.

Monoclonal antibodies specific for epitopes of other selected regions of the p300 protein may be generated using the above strategy and the complete amino acid sequence of the p300 protein, provided herein for the first time. For example, monoclonal antibodies specific for epitopes lying within any of the regions of p300 described herein, e.g., see Tables 1 and 2, may be generated using a p300 protein fragment containing that region as an immunogen, as described above for the carboxy terminal region of the protein. For example, additional antibodies having the specificity of the RW102 monoclonal antibody described herein may be generated using an immunizing peptide comprising amino acids 2023–2107 of p300; an antibody having the specificity of the RW105 antibody using an immunizing peptide comprising amino acids 1921–2023, etc. For purposes of the invention, it is not necessary that the carboxy terminal-binding antibody have the identical specificity as the five carboxy terminal-binding monoclonal antibodies described herein, but simply that the monoclonal antibody possess recognition properties with respect to the p300 carboxy terminal region that is used as the immunogen. Such monoclonal antibodies are useful for detecting mutations within a given region of p300; i.e., failure of the antibody to detect p300 in a tissue sample indicates an alteration in the cognate epitope and thus a mutation in that region of the protein.

MECHANISM OF ACTION

Our experiments provide direct evidence that p300 is an activator of enhancer-dependent transcription. Silencing of the SV40 enhancer by E1A can be reversed by p300 molecules lacking part of their E1A binding domain. In effect, these p300 versions render the SV40 enhancer partially resistant (or immune) to the inhibitory effect of E1A, even at very high intracellular concentrations. In the absence of E1A, the SV40 enhancer is fully active, and exogenous p300 is unable to further stimulate its activity. This suggests that p300 is not a limiting factor for enhancer function under normal circumstances. Our results also suggest that the E1A binding domain of p300 is dispensable for its transcriptional activation function, at least in the context of the SV40 enhancer. This is remarkable because deletions in the E1A binding domain of the RB-family of proteins (the pocket) completely abrogate the activity of this group of proteins (Shew et al., 1990, Cell Growth Diff. 1:17–25; Zhu et al., 1993, Genes & Der. 7:1111–1125).

The protein sequence of p300 predicts a bromodomain, located in the center of p300, as well as three distinct regions rich in cysteines and histidines. Since many of the proteins containing a bromodomain are implicated as transcriptional adaptors or coactivators, it is likely that p300 functions as a coactivator. In support of such a function was the ability of p300 to partially reactivate the SV40 enhancer when it was silenced by E1A.

What is known about the role of the bromodomain in activation of transcription? Experiments carried out with a subclass of bromodomain proteins containing adjacent to this domain a region of homology to helicases and DNA-dependent ATPases, namely yeast SNF2 (Laurent et al., 1991, Proc. Natl. Acad. Sci. U.S.A. 88:2687–2691) and one of its human homologs, hbrm (Muchardt and Yaniv, 1993, Embo. J. 12:4279–4290), indicate that the bromodomain of these two proteins is dispensable for transcriptional activation. In both proteins, this function appears to depend on an intact helicase function which is thought to assist transcription factors in displacing nucleosomes. Another subclass of proteins with bromodomains, represented for example by the yeast protein GCN5 (Georgakopoulos and Thireos, 1992, Embo. J. 11:4145–4152) and the human TBP-associated factor TAF$_{II}$250/CCG1, do not contain a helicase-like domain. In the case of GCN5, genetic data indicates that this protein enhances the transactivation function of the transcription factor GCN4. Several lines of experimental evidence point to a key role of TAF$_{II}$250 in transcriptional activation. It performs a central function in the molecular assembly of TFIID (Weinzierl et al., 1993, supra), and is essential for the progression of the G1-phase of the cell cycle (Sekiguchi et al., 1991, supra), most likely by modulating the activity of a subset of genes required for entry into S-phase (Wang and Tjian, 1994, Science 263:811–814). Since proteins containing bromodomains have to collaborate with multiple components of the transcription machinery, it is assumed that the bromodomain acts as a surface for protein-protein interactions.

Besides the bromodomain, it is also noteworthy that cysteine/histidine-rich motifs occur in a number of other known or suspected coactivator proteins. Among these are the yeast ADA2 protein (Berger et al., 1992, Cell 70:251–265), the human CREB binding protein, CBP (Chrivia et al., 1993, Nature 365:855–859), Drosophila and human trithorax polypeptides (Mazo et al., 1990, Proc. Natl. Acad. Sci. U.S.A. 87:2112–2116; Gu et al., 1992, Cell 71:701–708; Tkachuk et al., 1992, Cell 71:691–700), and the 13S E1A RNA product. Each of these proteins displays a unique spacing of cysteines which are thought to coordinate divalent metal ions. The cysteine rich motif might serve to provide to these transcription factors an extended and exposed surface, thereby enabling them to interact with multiple proteins at the same time. Our observation that the third cysteine and histidine rich domain of p300 interacts with at least one protein, namely E1A, lends support to this notion.

How may p300 stimulate enhancer-controlled transcription? Extensive deletion analyses of the SV40 enhancer have shown that the silencing effect of E1A is not dependent on specific sequences (Rochette-Egly et al., 1990, supra). Hence, it appears that p300 does not activate the enhancer as a classical transcription factor by binding to a specific sequence element and triggering transactivation. Taking the results of Rochette-Egly et al. (1990, supra) and the above noted structural features of p300 into account, it is more likely that p300 functions in a more indirect way, for example as an adaptor or bridging molecule communicating the activation potential of the enhancer-bound transcription factors to the promoter and to the basal transcription machinery. Given the large number of transcription factors binding to enhancers, steric interference probably precludes that all of them can directly interact with the basal transcription apparatus, especially when one considers that the promoter-bound transcription factors (e.g. Sp1 in the case of SV40) also need to contact the basic transcription factors. Molecules that sense the activation potential of enhancer-bound transcription factors and help in transmitting it to the transcription machinery are therefore probably essential. The large size of p300 and its multiple potential domains for protein-protein interactions are certainly compatible with such a model.

It has been reported that p300 has the ability to recognize sequences that resemble NFK-B/H2TF1-like sites (Rikitake and Moran, 1992, Mol. Cell. Biol. 12:2826–2836). Such a sequence element is present in the SV40 enhancer. However, other enhancers that are also sensitive to repression by E1A do not contain this motif (e.g. the polyomavirus enhancer (Borelli et al., 1984, supra; Velcich et al., 1985, supra) or the insulin enhancer (Stein et al., 1987, supra). Furthermore, as pointed out before, various Subfragments of the SV40 enhancer that do not encompass the H2TF1-like motif can still be repressed by E1A (Rochette-Egly et al., 1990, supra). Based on these considerations, it appears unlikely that p300 acts solely via the H2TF1-like site in stimulating transcription directed either by the SV40 enhancer or by other viral and cellular enhancers that are also the target of E1A imposed repression. In preliminary experiments using full length p300 produced in a baculovirus expression system, we have not detected a specific interaction between radiolabelled SV40 enhancer DNA sequences and p300.

An intriguing correlation between the sensitivity of certain enhancers towards silencing by E1A and the inactivity of the same enhancers in undifferentiated embryonal carcinoma (EC) cells has been noted previously (Borelli et al., 1984, supra; Gorman et al., 1985, Cell 42:519–526; Sleigh and Lockett, 1985, Embo J. 4:3831– 3837). It has been proposed that a cellular E1A-like activity, present only in undifferentiated EC cells (Imperiale et al., 1984, Mol. Cell. Biol. 4:867–874) is responsible for the lack of activity of these enhancers in EC cells. An attractive hypothesis is that this cellular E1A-like activity interacts directly with p300 and negatively regulates its role as transcriptional adaptor protein, perhaps in a manner similar to E1A.

Binding of E1A to p300 is sufficient to induce S-phase entry of quiescent cells. E1A can perform this function without binding to the CR2 associated proteins, albeit less efficiently (reviewed in Moran, 1993, supra). This finding may mean that p300 is a negative regulator of cell growth which is inactivated by E1A. In addition, E1A represses, via p300 binding, tissue specific genes associated with the terminal differentiation state of cells (Hen et al., 1985, supra; Stein et al., 1987, supra; Webster et al., 1988, supra; Braun et al., 1992, Genes & Der. 6:888–902; Caruso et al., 1993, Oncogene 8:267–278; Boulukos and Ziff, 1993, Oncogene 8:237–248). In light of our results suggesting a role for p300 as a transcriptional adaptor protein, we propose that one part of the cell cycle inhibitory function of p300 is to activate (together with cell type-specific transcription factors) enhancers of genes required for arrest in G0/G1 and terminal differentiation. One of the natural targets of adenovirus infections are differentiated epithelial cells lining the respiratory tract. In order to induce S-phase and to replicate its own DNA in these infected cells, it is probably essential for adenovirus to interfere with this growth repressive role of p300.

OTHER EMBODIMENTS

Other embodiments will be evident to those of skill in the art. It should be understood that the foregoing detailed description is provided for clarity only and is merely exemplary. The spirit and scope of the present invention are not limited thereto, being defined by the claims set forth below.

We claim:

1. An isolated nucleic acid encoding a human p300 polypeptide having the amino acid sequence of SEQ ID NO:2.

2. A nucleic acid probe comprising 1 nucleotides that hybridizes under stringent conditions with a region of the nucleotide sequence of SEQ ID NO:1.

3. A vector comprising the isolated nucleic acid of claim 1 or the nucleic acid probe of claim 2.

4. The vector of claim 3, wherein said vector is a baculovirus vector.

5. A host cell transfected with the vector of claim 3.

6. The host cell of claim 5, wherein said cell is a mammalian cell.

7. A kit for detecting p300 nucleic acids, comprising the isolated nucleic acid of claim 1 or the nucleic acid probe of claim 2.

8. The nucleic acid probe of claim 2, comprising 50–80 nucleotides.

9. The nucleic acid probe of claim 2, comprising 100–300 nucleotides.

10. An isolated nucleic acid encoding amino acids 346–415 of SEQ ID NO:2.

11. An isolated nucleic acid encoding amino acids 1070–1134 of SEQ ID NO:2.

12. An isolated nucleic acid encoding amino acids 1162–1452 of SEQ ID NO:2.

13. An isolated nucleic acid encoding amino acids 1638–1807 of SEQ ID NO:2.

14. An isolated nucleic acid encoding amino acids 1572–1818 of SEQ ID NO:2.

15. An isolated acid encoding amino acids 1868–1921 of SEQ ID NO:2.

16. An isolated nucleic acid encoding amino acids 1921–2023 of SEQ ID NO:2.

17. An isolated nucleic acid encoding amino acids 2023–2107 of SEQ ID NO:2.

18. An isolated nucleic acid encoding amino acids 2107–2283 of SEQ ID NO:2.

19. An isolated nucleic acid encoding a polypeptide having the amino acid sequence of SEQ ID NO:2, except that amino acids 346–415 are deleted.

20. An isolated nucleic acid encoding a polypeptide having the amino acid sequence of SEQ ID NO:2, except that amino acids 1070–1134 are deleted.

21. An isolated nucleic acid encoding a polypeptide having the amino acid sequence of SEQ ID NO:2, except that amino acids 1162–1452 are deleted.

22. An isolated nucleic acid encoding a polypeptide having the amino acid sequence of SEQ ID NO:2, except that amino acids 1638–1807 are deleted.

23. An isolated nucleic acid encoding a polypeptide having the amino acid sequence of SEQ ID NO:2, except that amino acids 1572–1818 are deleted.

24. An isolated nucleic acid encoding a polypeptide having the amino acid sequence of SEQ ID NO:2, except that amino acids 1737–1809 are deleted.

25. An isolated nucleic acid encoding a polypeptide having the amino acid sequence of SEQ ID NO:2, except that amino acids 1737–1836 are deleted.

26. An isolated nucleic acid encoding a fusion protein consisting of the nucleic acid of any one of claims 10–18 joined to a nucleic acid encoding a non-p300 polypeptide.

* * * * *

UNITED STATES PATENT AND TRADEMARK OFFICE
CERTIFICATE OF CORRECTION

PATENT NO. : 5,658,784  
DATED : August 19, 1997  
INVENTOR(S) : Richard Eckner, et al.

Page 1 of 3

It is certified that error appears in the above-indentified patent and that said Letters Patent is hereby corrected as shown below:

Column 4, line 39, "SEQ ID NO:1 cDNA and its..." should read --cDNA (SEQ ID NO:1) and its...--.

Column 4, line 40, "SEQ ID NO:2" should read --(SEQ ID NO:2)--.

Column 4, line 55, "hBRM see SEW ID NO:7 is a" should read --hBRM (see SEQ ID NO:7) is a--.

Column 4, line 67, "PEREGRIN-M91585 see SEQ. ID. NO:8." should read --PEREGRIN-M91585 (sec SEQ ID NO:8).--.

Column 6, line 8, "del⌢30 and del⌢33)6 were" should read --del⌢30 and del⌢33) were--.

Column 7, line 51, "human p300 a SEQ ID NO:1 nd mapped" should read --human p300 (SEQ ID No:1) and mapped--.

Column 7, line 53, "p300 SEQ ID NO:2" should read --p300 (SEQ ID NO:2)--.

Column 8, line 36, "lambda-gtil" should read --lambda-gt11--.

Colunm 10, line 6, "Genes & Der." should read --Genes & Dev.--.

UNITED STATES PATENT AND TRADEMARK OFFICE
CERTIFICATE OF CORRECTION

PATENT NO. : 5,658,784
DATED : August 19, 1997
INVENTOR(S) : Richard Eckner, et al.

It is certified that error appears in the above-indentified patent and that said Letters Patent is hereby corrected as shown below:

Column 12, line 14, "-3' SEQ ID NO:9" should read ---3'(SEQ ID NO:9)--.

Column 12 lines 22 and 23, "-3' SEQ ID NO:10" should read ---3'(SEQ ID NO:10)--.

Column 12, line 24, "-3' SEQ ID NO:11" should read ---3'(SEQ ID NO:11)--.

Column 12, line 32, "-3' SEQ ID NO:12" should read ---3'(SEQ ID NO:12)--.

Column 12, lines 36 and 37, "-3'SEQ ID NO:13" should read ---3'(SEQ ID NO:13)--.

UNITED STATES PATENT AND TRADEMARK OFFICE
CERTIFICATE OF CORRECTION

PATENT NO. : 5,658,784
DATED : August 19, 1997
INVENTOR(S) : Richard Eckner, et al.

It is certified that error appears in the above-identified patent and that said Letters Patent is hereby corrected as shown below:

Column 16, line 42, "corresponding to mR/qA" should read --corresponding to mRNA--.

Column 22, line 32, "Genes & Der." should read --Genes & Dev.--.

Column 24, line 35, "Genes & Der." should read --Genes & Dev.--.

Column 61, claim 2, "comprising 1 nucleotides" should read --comprising 30 nucleotides--.

Signed and Sealed this

Tenth Day of November 1998

Attest:

BRUCE LEHMAN

Attesting Officer

Commissioner of Patents and Trademarks